US008789736B2

(12) United States Patent
    Dudai

(10) Patent No.: US 8,789,736 B2
(45) Date of Patent: Jul. 29, 2014

(54) STAPLES, STAPLERS, ANASTOMOSIS DEVICES, AND METHODS FOR THEIR APPLICATIONS

(76) Inventor: Moshe Dudai, Zikhron-Yaakov (IL)

( * ) Notice: Subject to any disclaimer, the term of this patent is extended or adjusted under 35 U.S.C. 154(b) by 621 days.

(21) Appl. No.: 11/883,490

(22) PCT Filed: Feb. 5, 2006

(86) PCT No.: PCT/IL2006/000142
§ 371 (c)(1),
(2), (4) Date: Aug. 1, 2007

(87) PCT Pub. No.: WO2006/082586
PCT Pub. Date: Aug. 10, 2006

(65) Prior Publication Data
US 2008/0277450 A1   Nov. 13, 2008

Related U.S. Application Data

(60) Provisional application No. 60/649,542, filed on Feb. 4, 2005.

(51) Int. Cl.
    *A61B 17/04* (2006.01)
(52) U.S. Cl.
    CPC .............. *A61B 17/04* (2013.01); *Y10S 227/901* (2013.01); *Y10S 227/902* (2013.01)
    USPC ...................... 227/175.1; 227/179.1; 227/901; 227/902; 227/120; 227/19; 606/219; 606/139
(58) Field of Classification Search
    USPC ........ 227/175.1, 19, 901, 902, 109, 120, 119, 227/135, 136, 179.1; 606/219, 139–142
    See application file for complete search history.

(56) References Cited

U.S. PATENT DOCUMENTS

| 5,002,563 | A | | 3/1991 | Pyka et al. |
| 5,499,990 | A | * | 3/1996 | Schulken et al. ............. 606/144 |
| 5,601,572 | A | | 2/1997 | Middleman et al. |
| 5,758,814 | A | | 6/1998 | Gallagher et al. |

(Continued)

FOREIGN PATENT DOCUMENTS

| WO | WO 00/57796 | 10/2000 |
| WO | WO 02/34121 | 5/2002 |

OTHER PUBLICATIONS

International Search Report Dated Mar. 20, 2008 From the International Searching Authority Re.: Application No. PCT/IL06/00142.

(Continued)

*Primary Examiner* — Michelle Lopez

(57) ABSTRACT

A stapling element is provided, operative to pierce and penetrate a tissue by a first end, and close around the tissue. Three factors help prevent local necrosis: 1. The self-closing feature of the staple does not lead to tissue crushing. 2. Edge seams are applied generally perpendicular to the tissue edge, allowing for blood supply to the tissue edge. 3. Excess tissue is cut off at the seam, minimizing the amount of tissue that may undergo local necrosis. A physical feature prevents the staple from rotating, when in an application shaft, to maintain a predetermined closing direction. The stapling element may be formed of an alloy, a pure metal, a polymer, or a composite of at least two materials. Additionally, staplers, anastomosis devices, and methods for their applications are described.

45 Claims, 38 Drawing Sheets

(56) References Cited

U.S. PATENT DOCUMENTS

| | | | |
|---|---|---|---|
| 5,810,851 A * | 9/1998 | Yoon | 606/148 |
| 5,830,221 A * | 11/1998 | Stein et al. | 606/157 |
| 6,113,611 A | 9/2000 | Allen et al. | |
| 6,120,526 A | 9/2000 | Daley | |
| 6,517,584 B1 | 2/2003 | Lecalve | |
| 6,835,199 B2 * | 12/2004 | McGuckin et al. | 606/142 |
| 6,981,983 B1 * | 1/2006 | Rosenblatt et al. | 606/216 |
| 7,112,208 B2 * | 9/2006 | Morris et al. | 606/144 |
| 7,285,087 B2 * | 10/2007 | Moaddeb et al. | 600/37 |
| 7,517,356 B2 * | 4/2009 | Heinrich | 606/219 |
| 2001/0021858 A1 | 9/2001 | Bolduc et al. | |
| 2003/0135226 A1 | 7/2003 | Bolduc et al. | |
| 2003/0225420 A1 | 12/2003 | Wardle | |
| 2003/0236550 A1 | 12/2003 | Peterson et al. | |
| 2004/0050393 A1 | 3/2004 | Golden et al. | |

OTHER PUBLICATIONS

Written Opinion Dated Mar. 20, 2008 From the International Searching Authority Re.: Application No. PCT/IL06/00142.

Communication Pursuant to Rules 70(2) and 70a(2) EPC Dated Jan. 24, 2014 From the European Patent Office Re. Application No. 06701836.6.

Supplementary European Search Report and the European Search Opinion Dated Dec. 18, 2013 From the European Patent Office Re. Application No. 06701836.6.

* cited by examiner

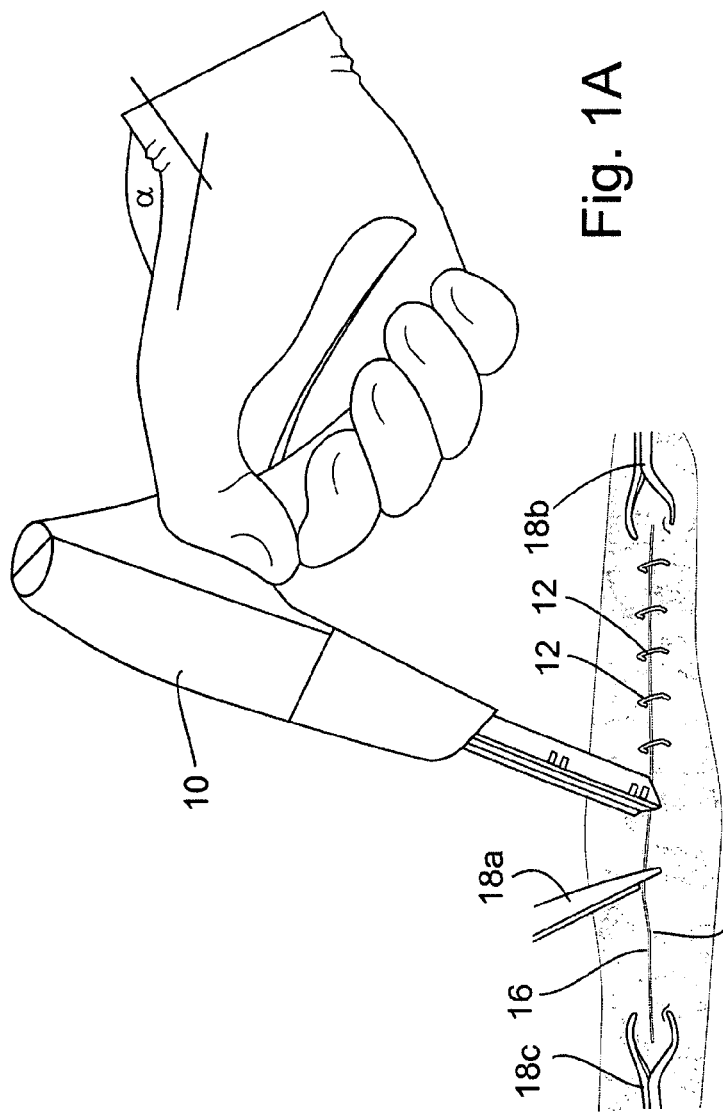
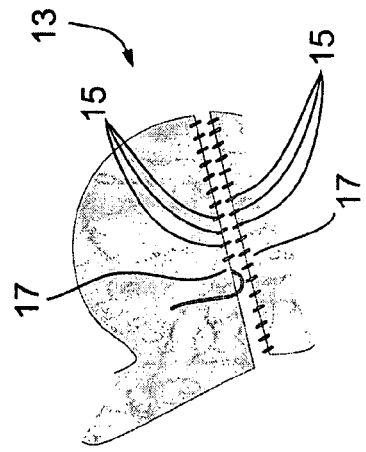
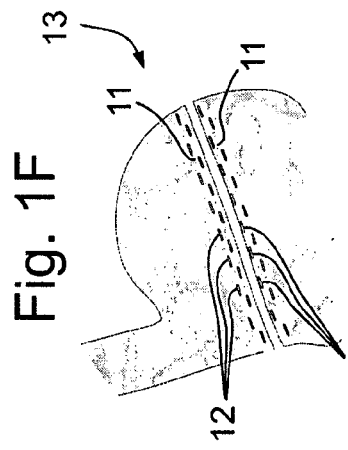
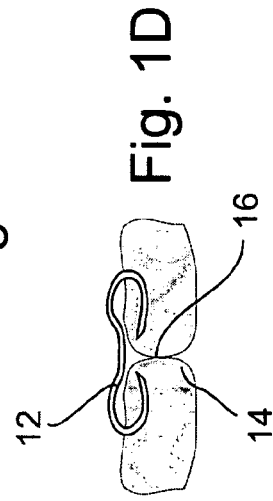
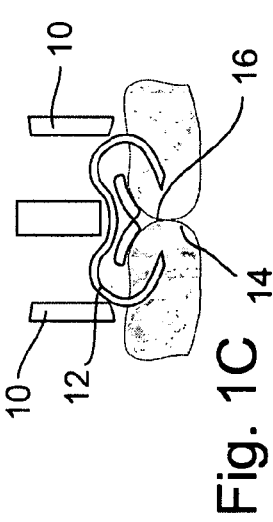
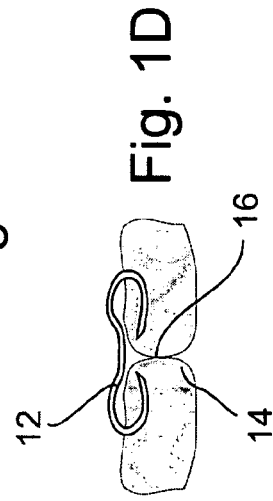

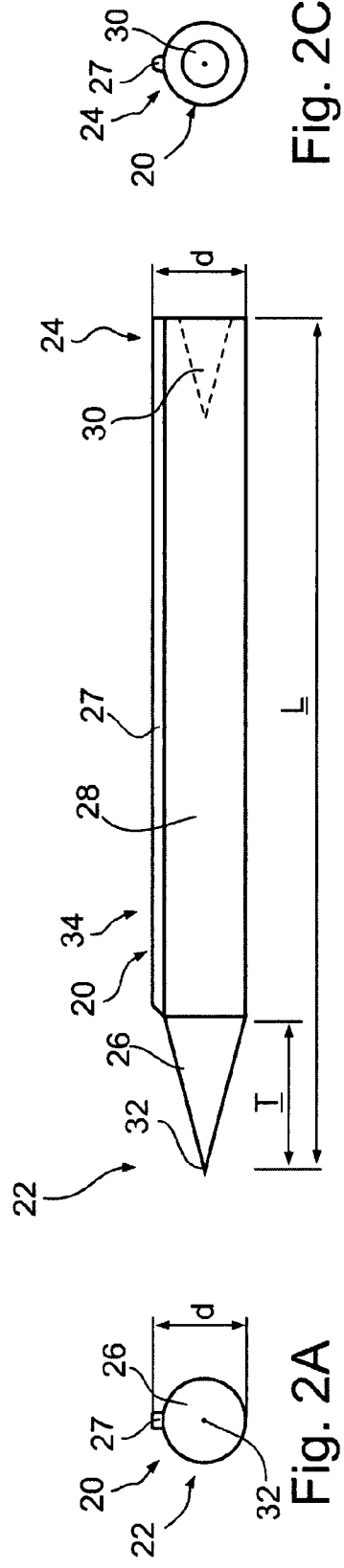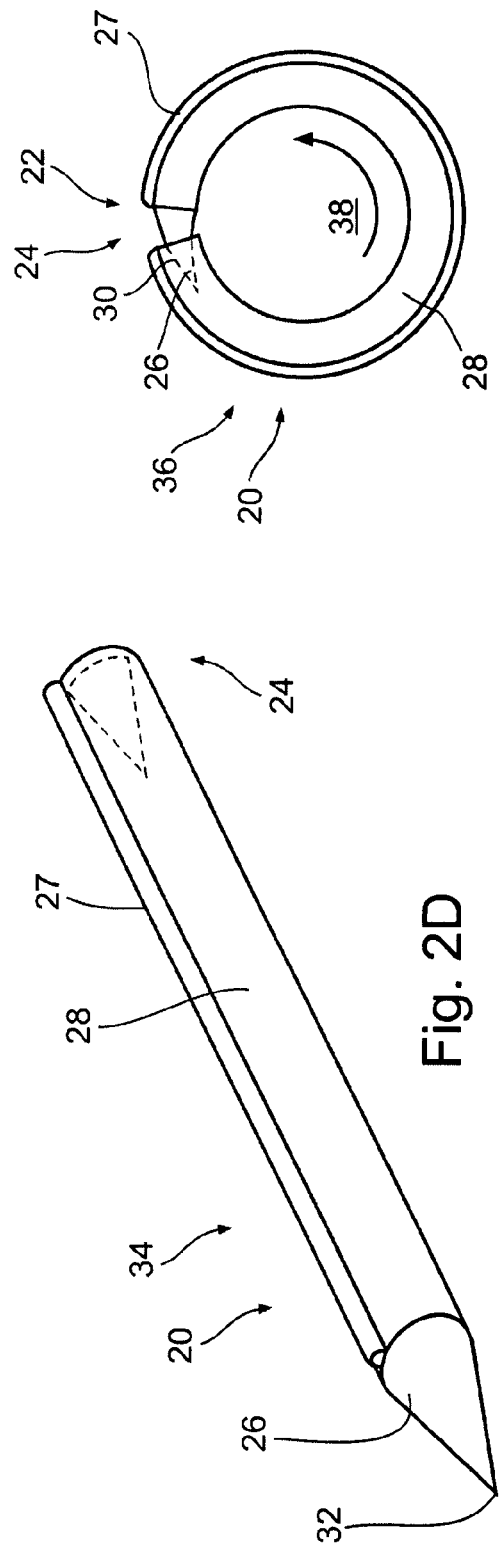

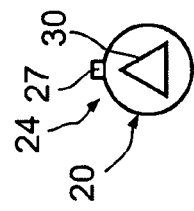
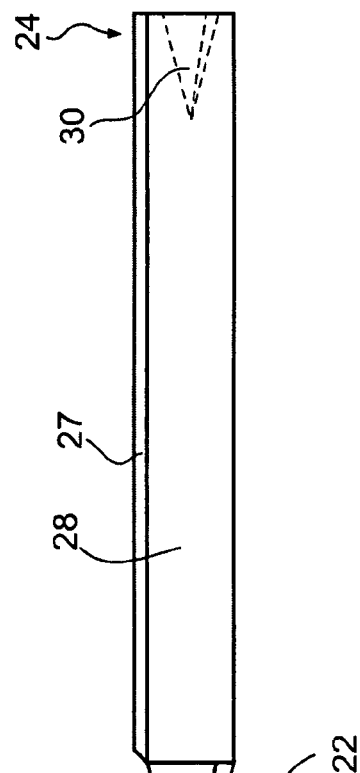
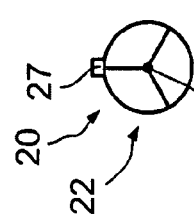
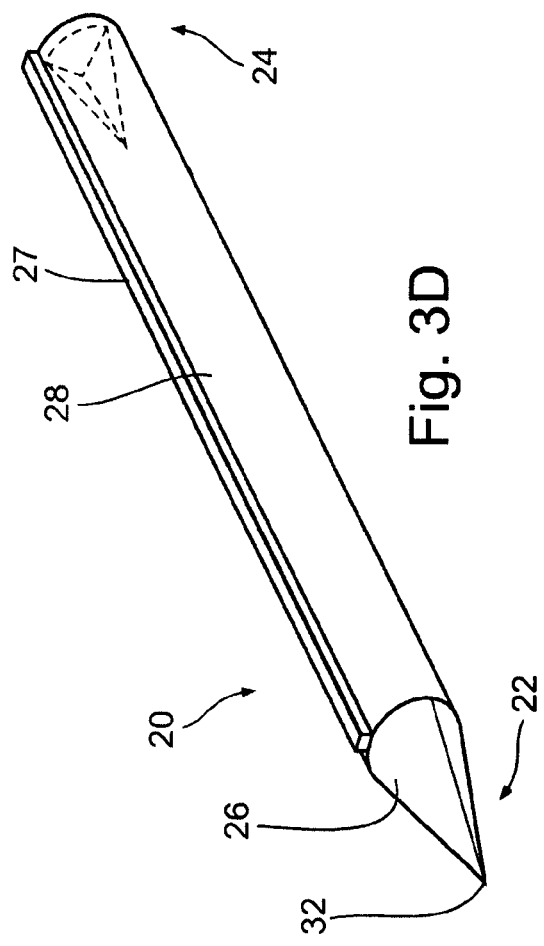

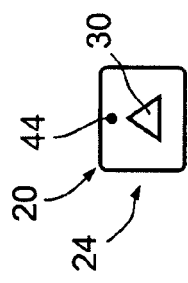
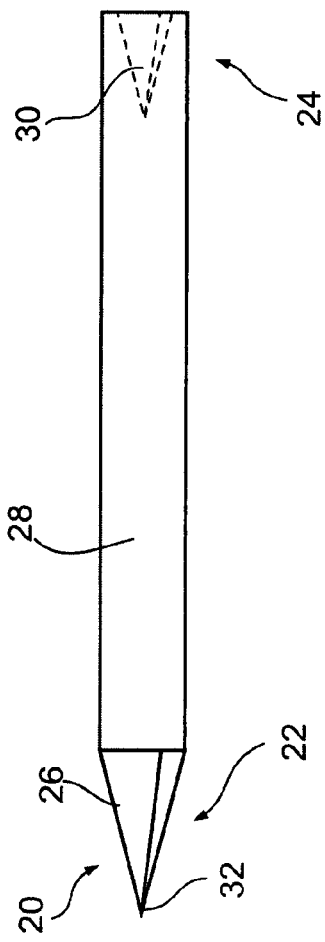
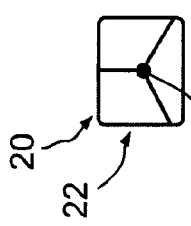
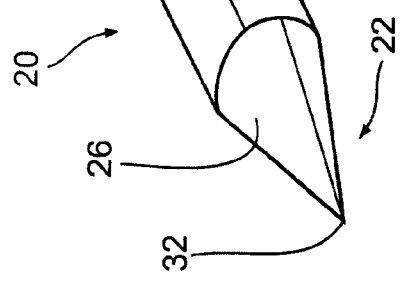

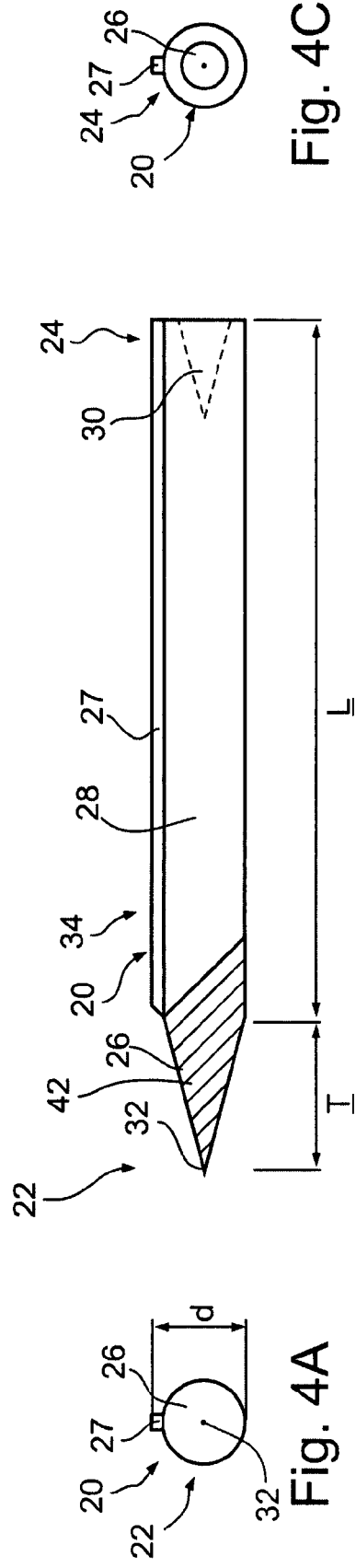

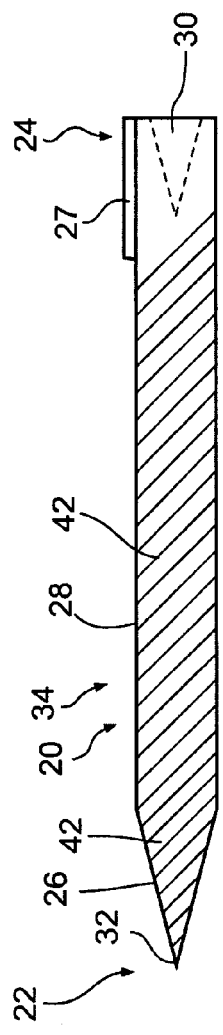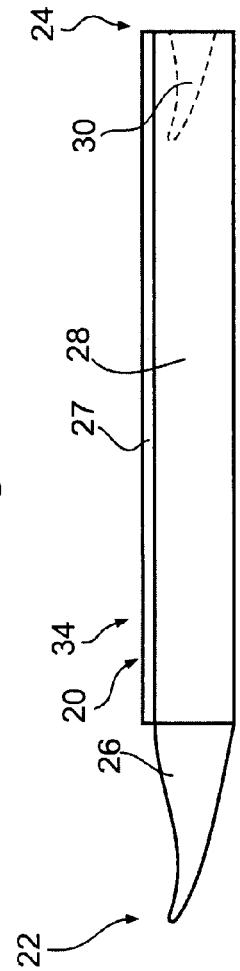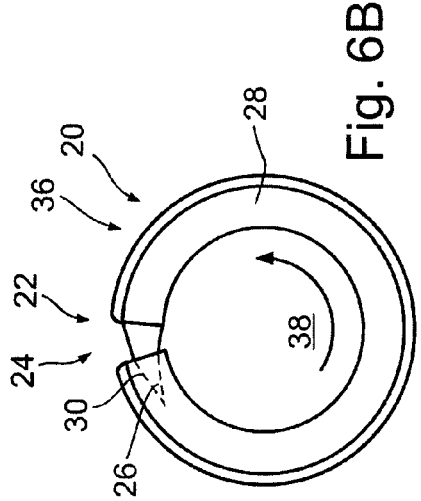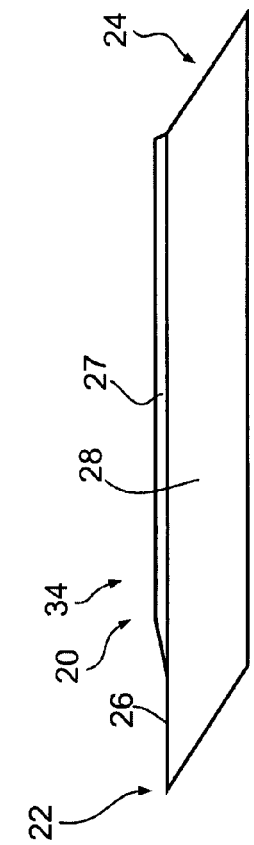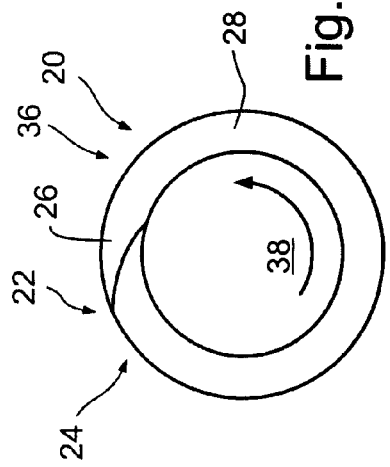

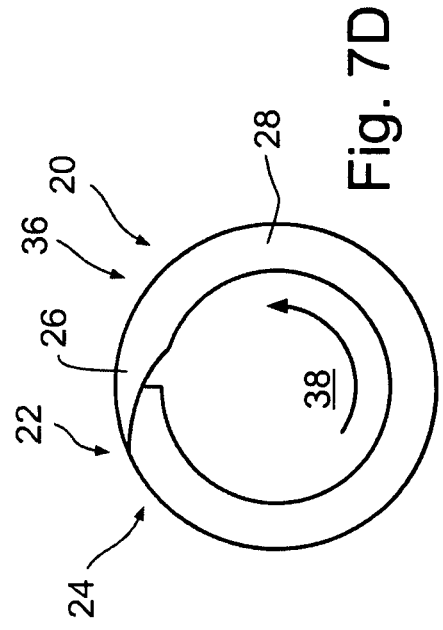
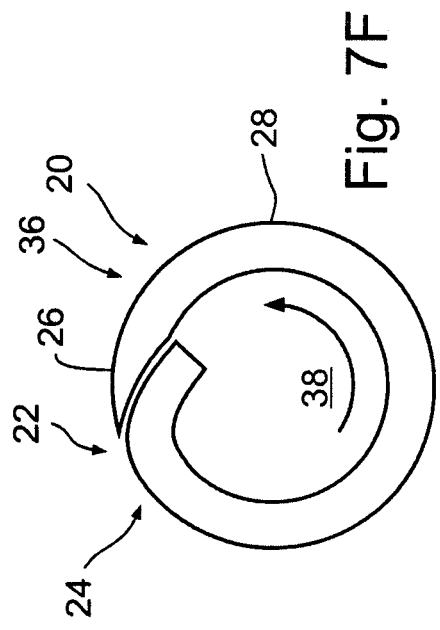
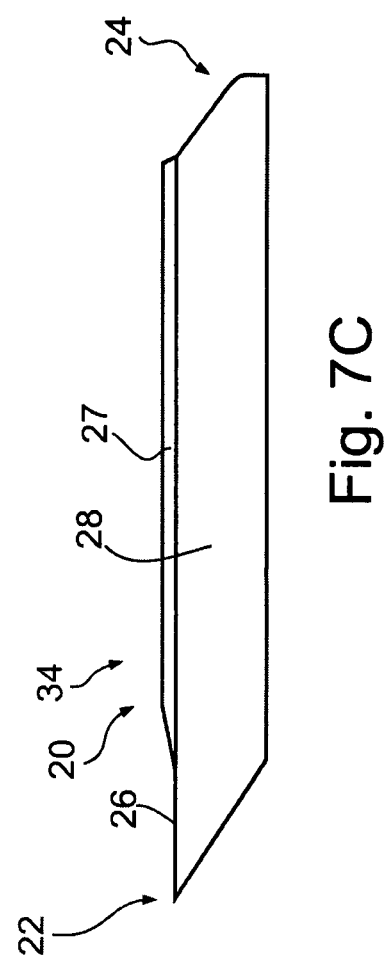
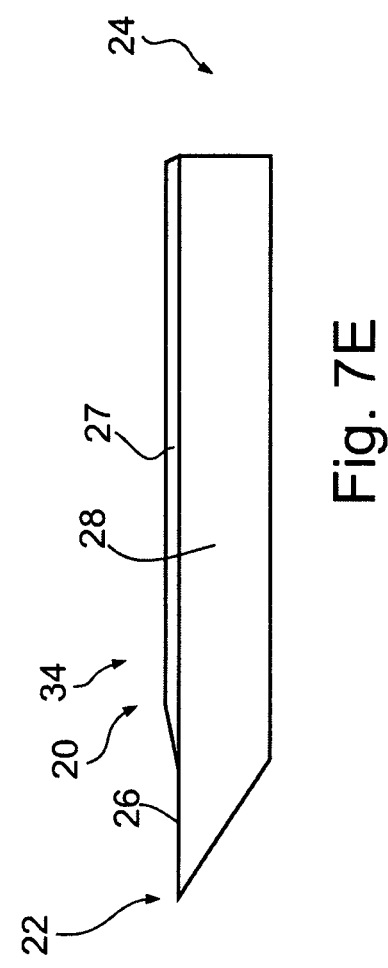

Fig. 16A 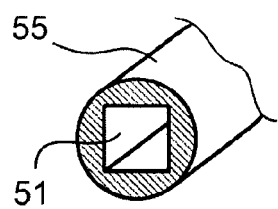 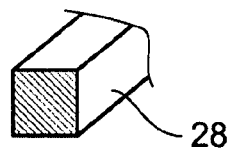 Fig. 15A
Fig. 16B 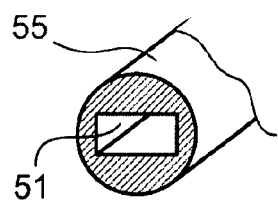 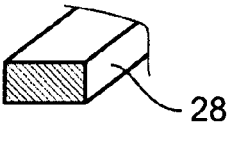 Fig. 15B
Fig. 16C 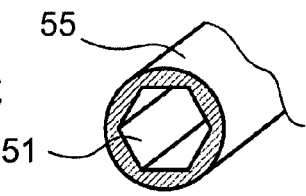 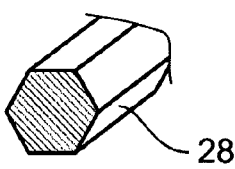 Fig. 15C
Fig. 16D 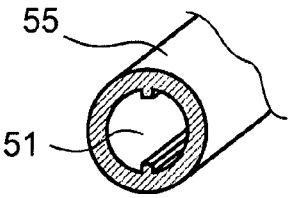 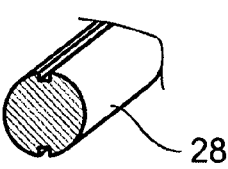 Fig. 15D
Fig. 16E 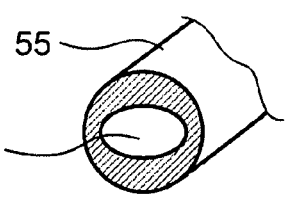 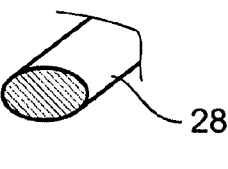 Fig. 15E
Fig. 16F 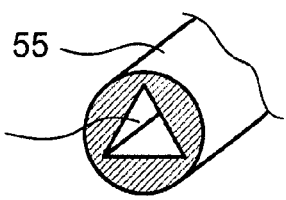 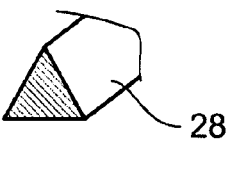 Fig. 15F
Fig. 16G 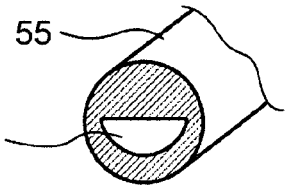 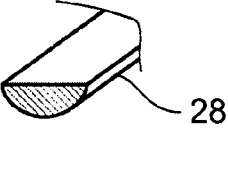 Fig. 15G
Fig. 16H 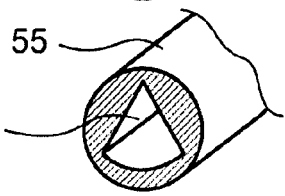 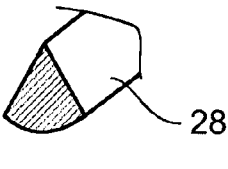 Fig. 15H

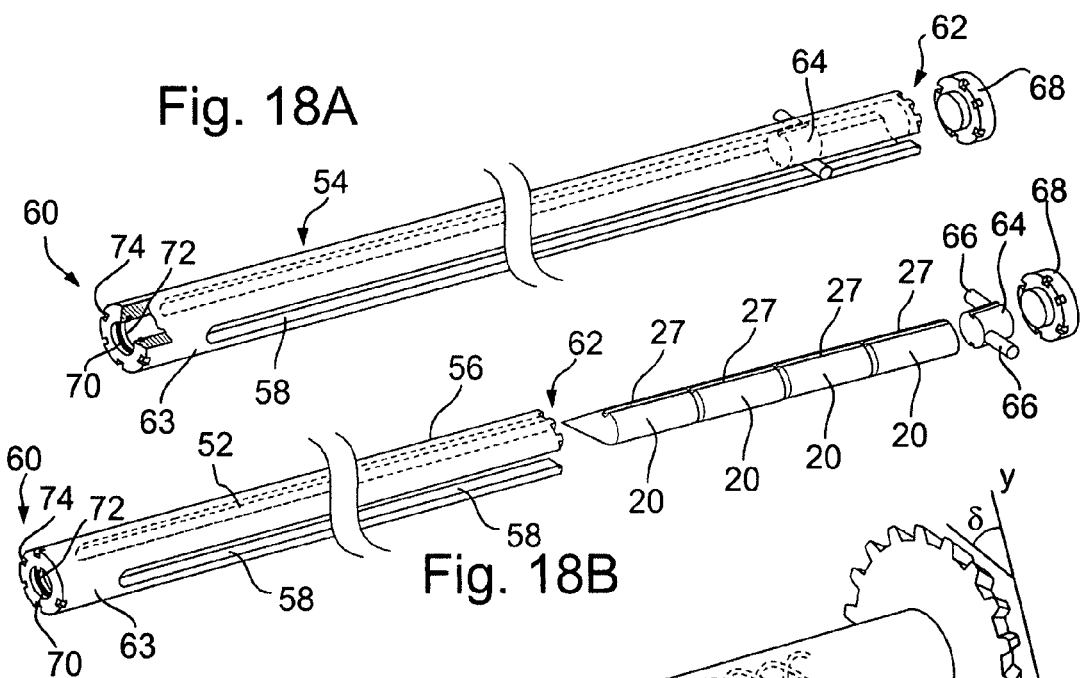
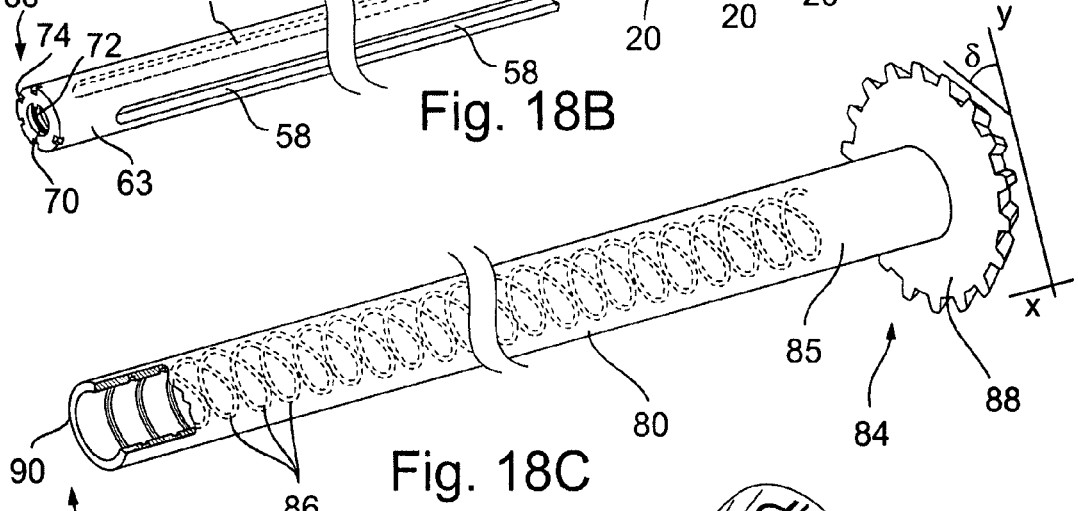
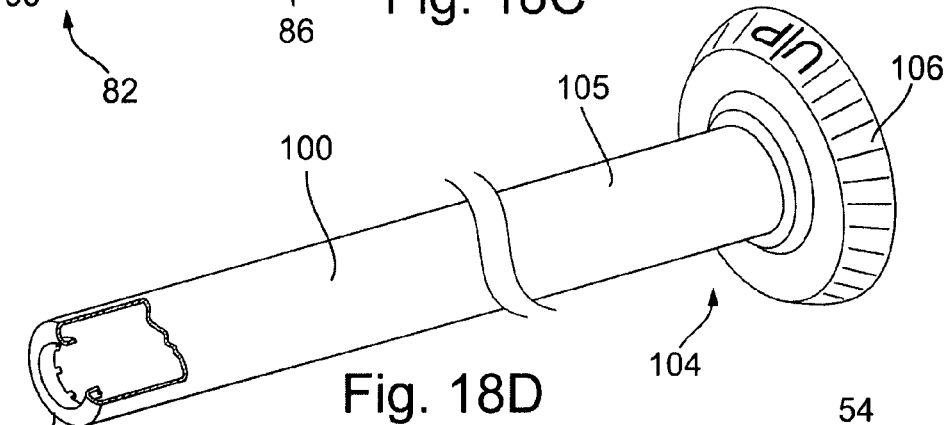
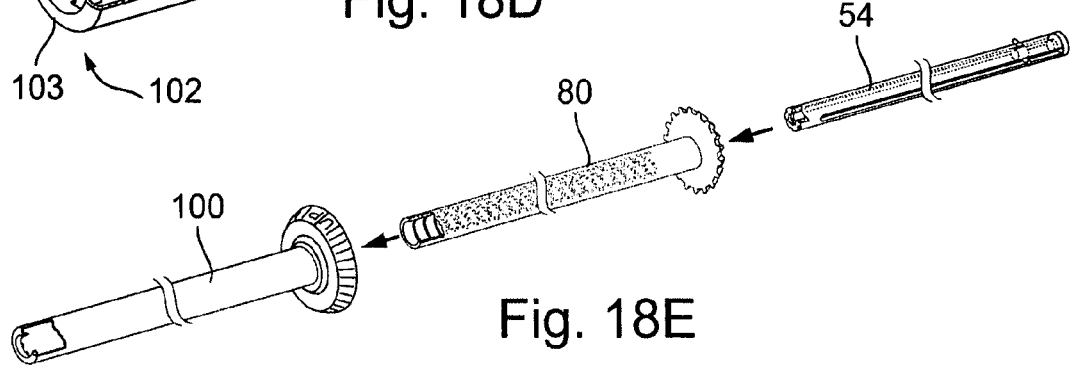

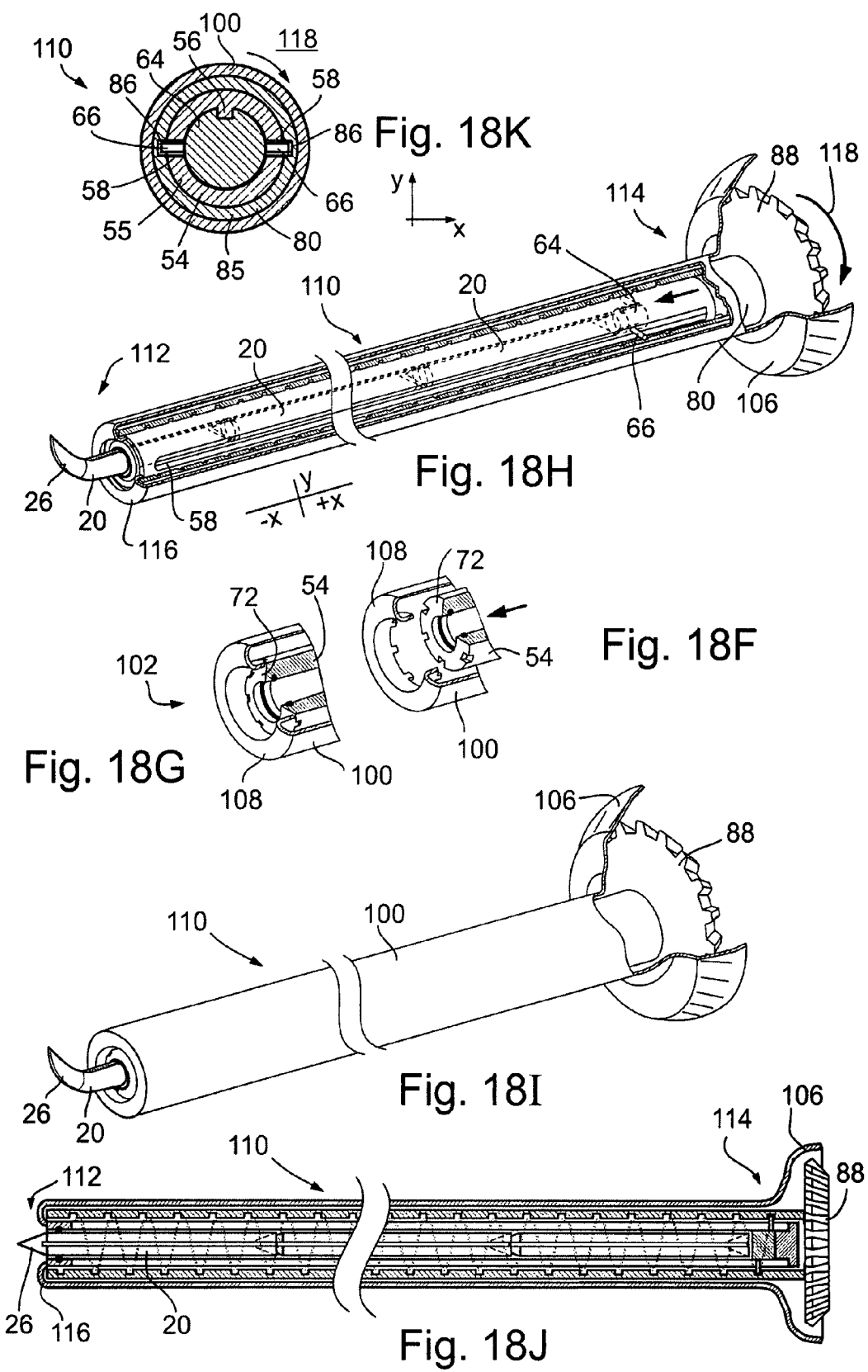

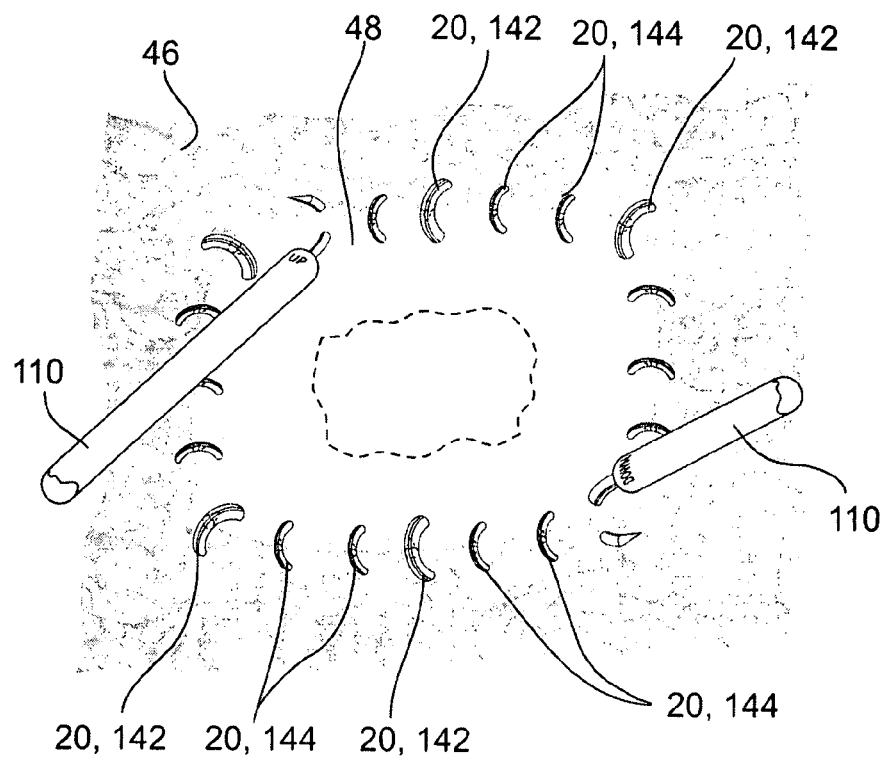
Fig. 20A
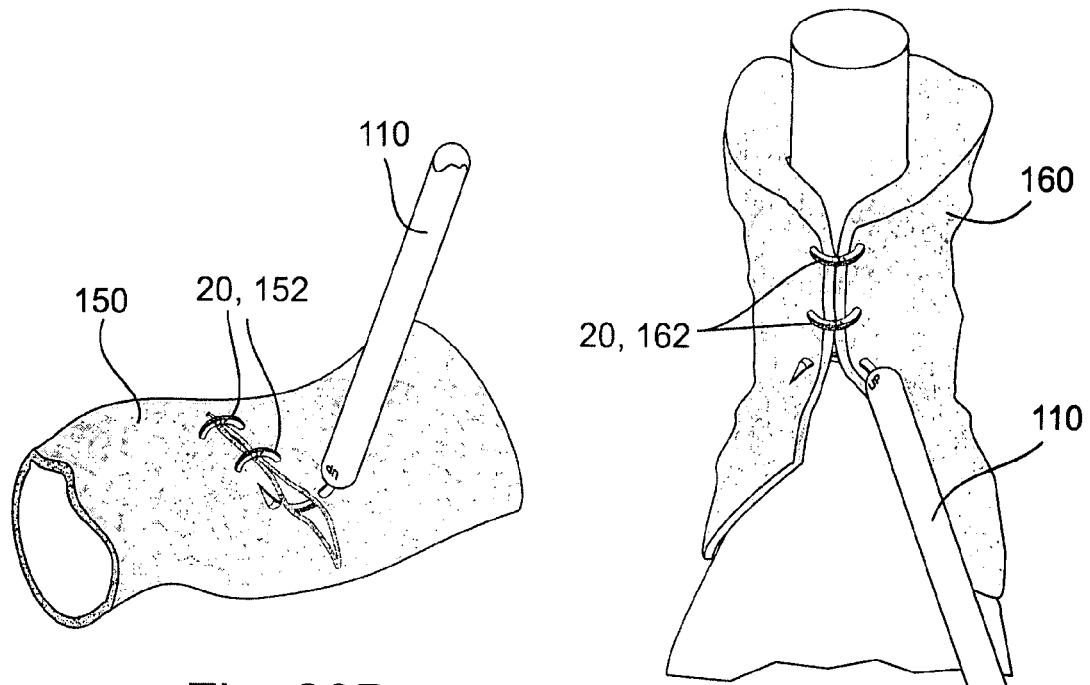
Fig. 20B
Fig. 20C

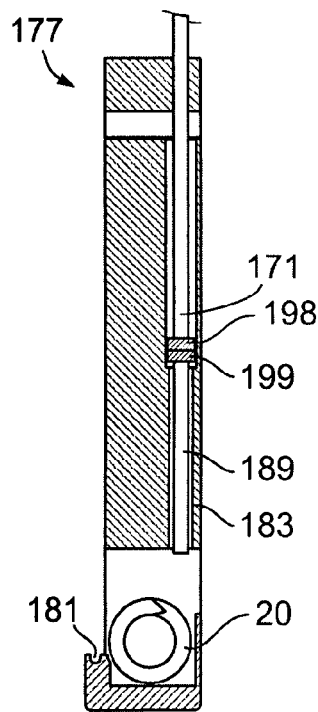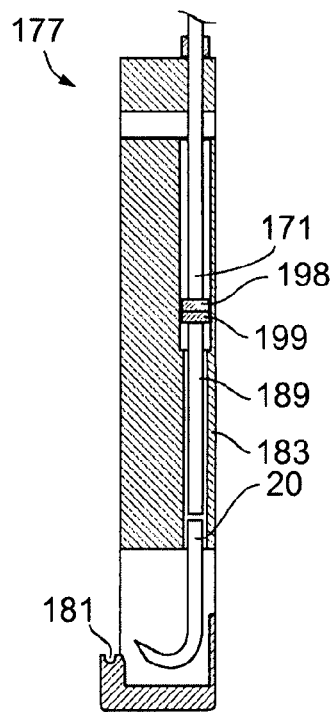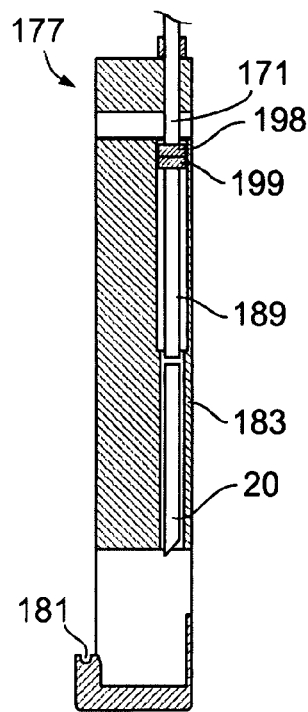
Fig. 22F  Fig. 22E  Fig. 22D
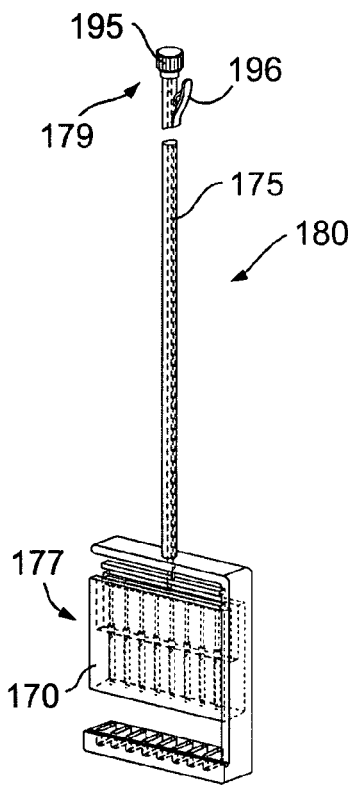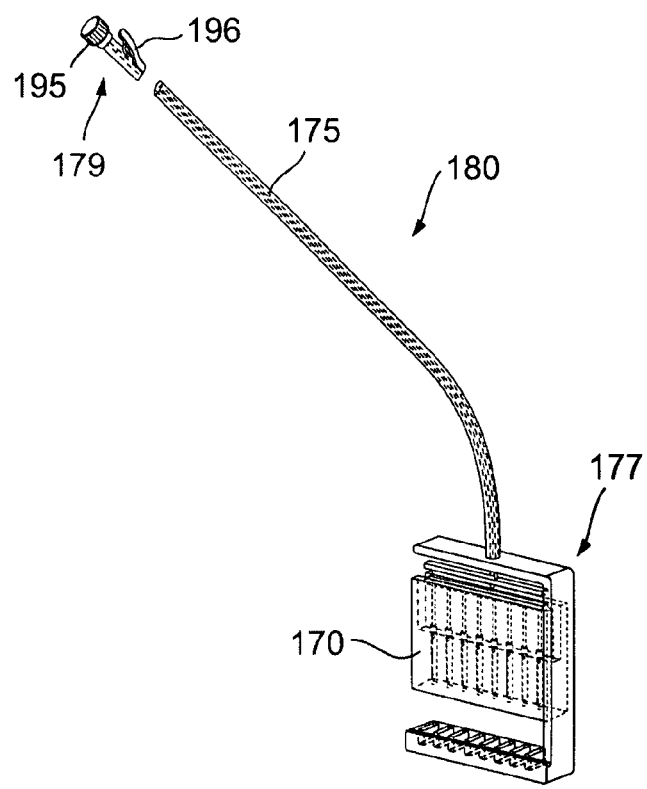
Fig. 22G  Fig. 22H

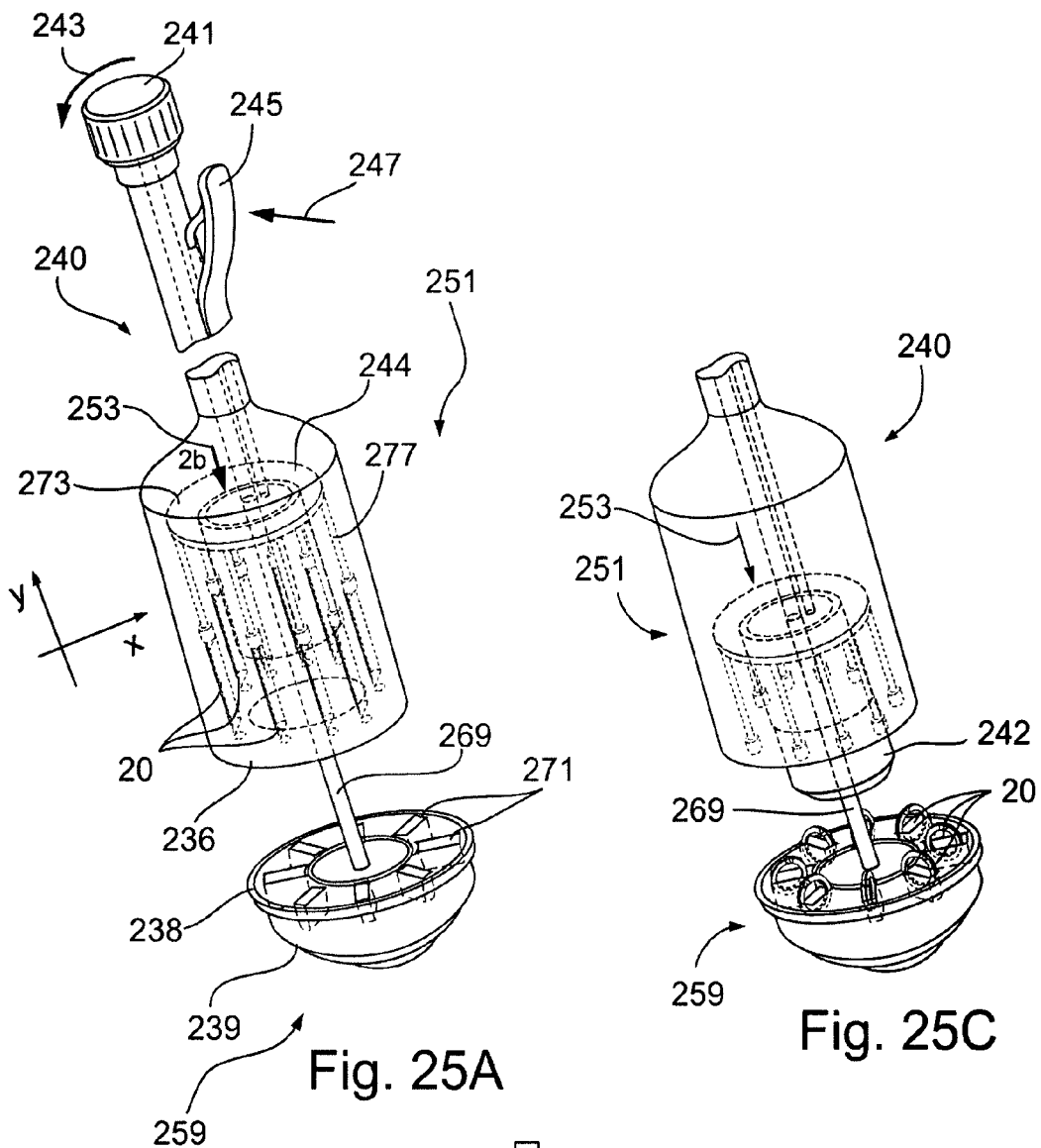
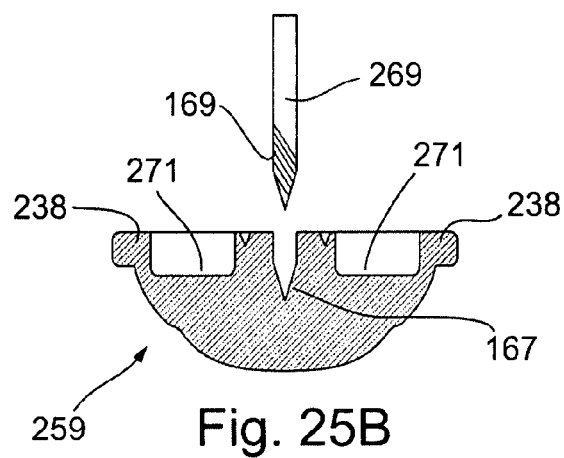
Fig. 25A
Fig. 25B
Fig. 25C

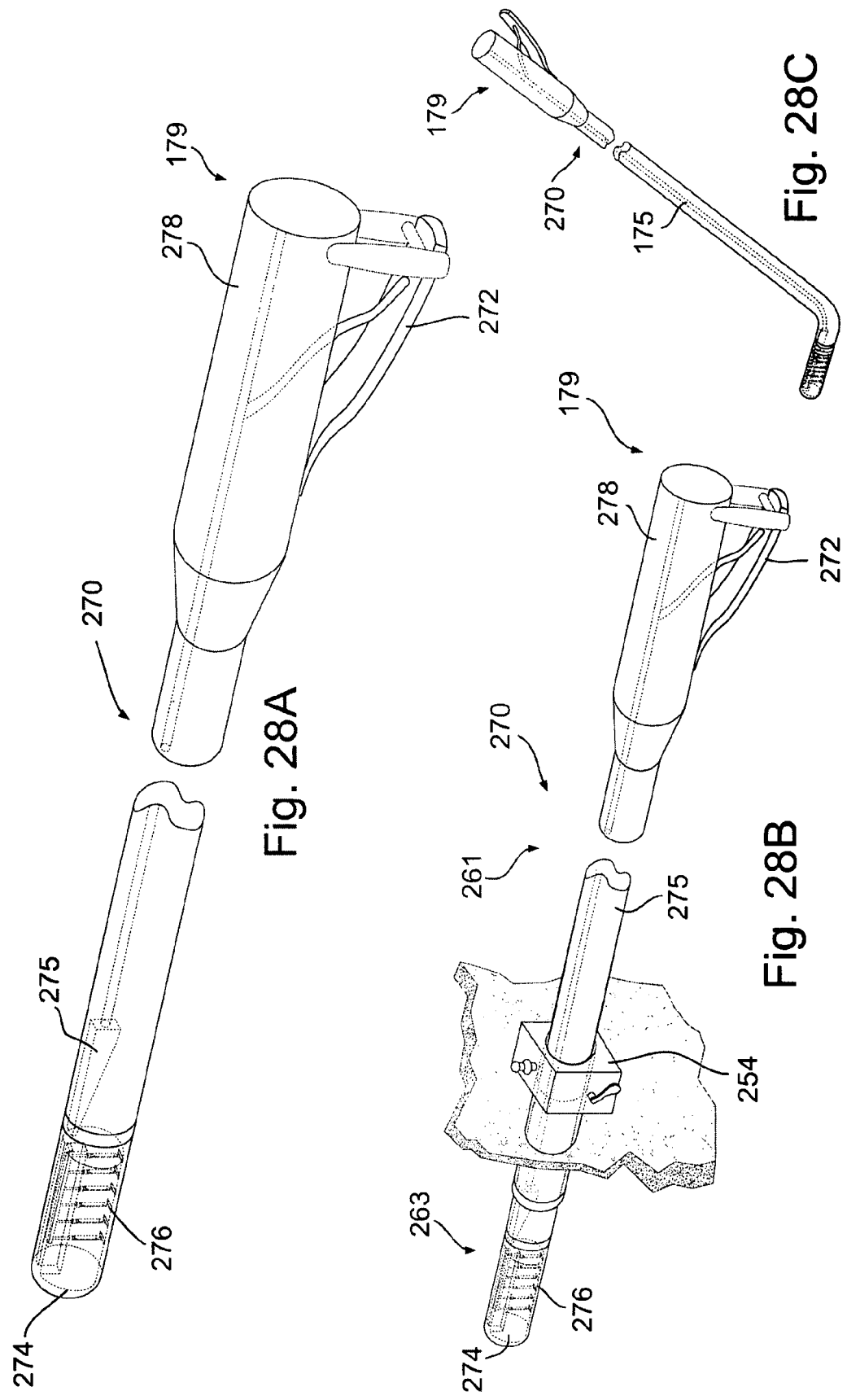

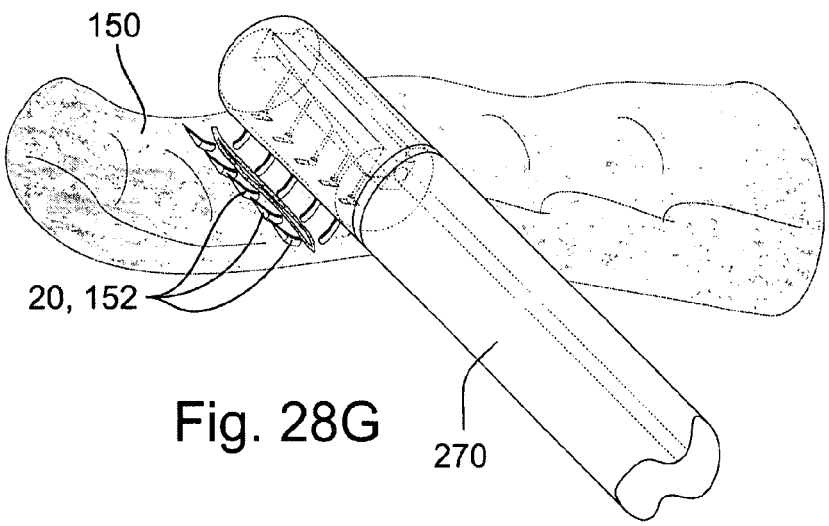
Fig. 28G
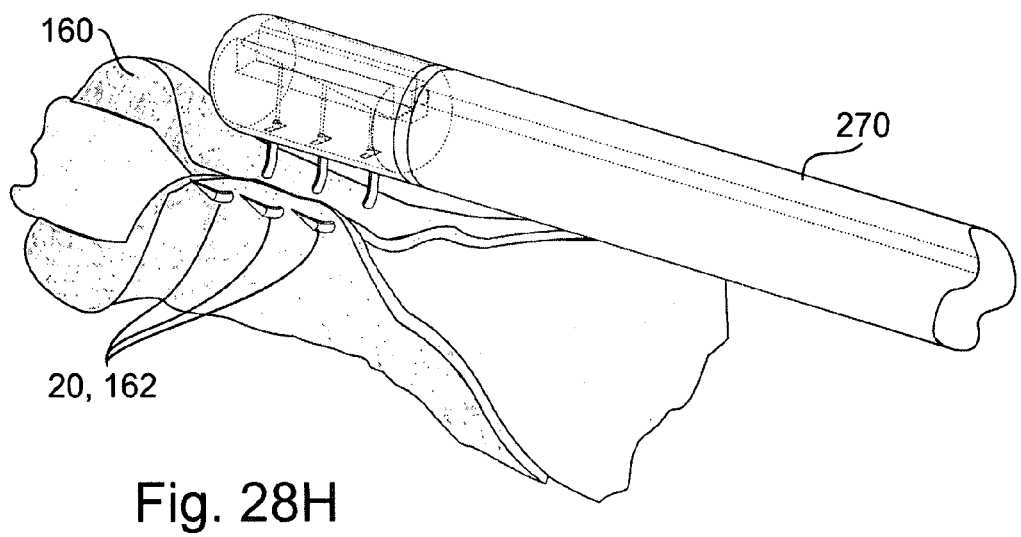
Fig. 28H
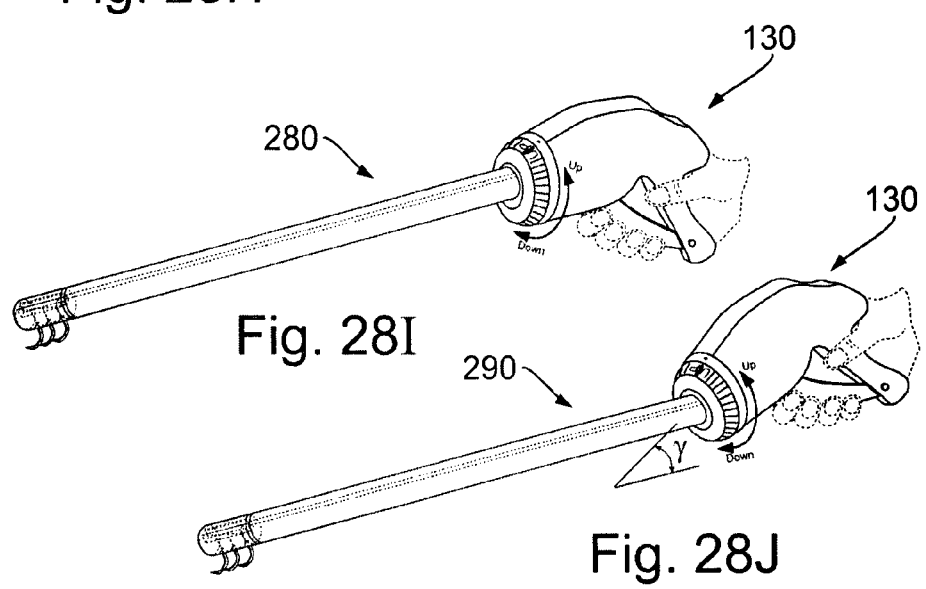
Fig. 28I
Fig. 28J

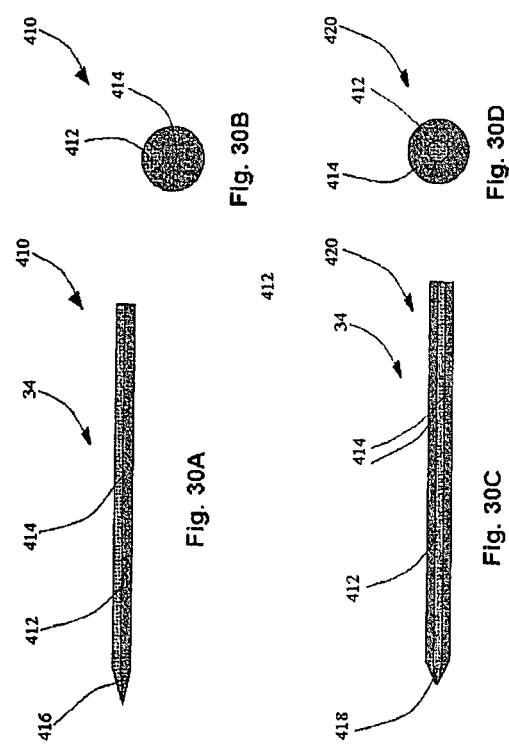

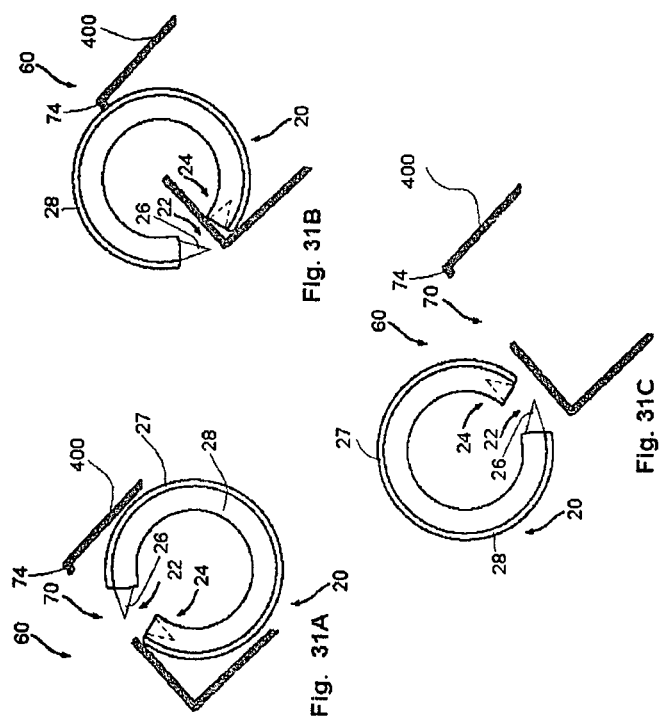

STAPLES, STAPLERS, ANASTOMOSIS DEVICES, AND METHODS FOR THEIR APPLICATIONS

RELATED APPLICATIONS

This Application is a National Phase of PCT Patent Application No. PCT/IL2006/000142 having International Filing Date of Feb. 5, 2006, which claims the benefit of U.S. Provisional Patent Application No. 60/649,542 filed on Feb. 4, 2005. The contents of the above Applications are all incorporated herein by reference.

FIELD AND BACKGROUND OF THE INVENTION

The present invention relates generally to surgical staples, staplers, anastomosis devices, and methods for their applications.

The surgical uniting of tissues or tendons with sutures is a demanding skill, requiring dexterous ease in performance. Post operation healing is best facilitated by as short as possible operation time, minimal blood loss, and least tissue manipulation and trauma. Yet, often, sutures are to be placed in difficult to reach places, and their specific location, size, and tautness must be carefully controlled and delicately manipulated. In addition, fatigue and loss of patience may have an effect on the quality of the sutures. Furthermore, there is great variance in the quality of sutures between highly skilled and lesser skilled surgeons.

Generally, fine threads are used to surgically close a wound or join tissues. Alternatively, surgical staples, for example, Auto Suture of U.S. Surgical, 150 Glover Avenue, Norwalk, Conn. 06856, may be employed.

FIGS. 1A-1D schematically illustrate skin closure by an Auto-Suture instrument 10 and shape-memory-alloy staples 12, which form figure-eight staples after insertion. For operation, the surgeon must maintain first and second fascia edges 14 and 16 taut, abut against each other, and hold instrument 10 substantially at a right angle to the fascia surface.

There are several disadvantages to the Auto-Suture system:

maintaining fascia edges 14 and 16 taut and abut against each other requires at least two additional tools, such as tools 18A, 18B and 18C of FIG. 1A. It would be advantageous, if the surgeon could grip first fascia edge 14, as if by needle, and bring it to second fascia edge 16, so that the overall number of tools be reduced;

Staple ejection by Auto Suture device 10 may be crushing to the tissue, possibly leading to local necrosis;

additionally, the figure eight that is formed by staples 12 may further crush the tissue, as seen in FIG. 1D, and may interfere with blood and nutrient flow, possibly leading to local necrosis; and when the Auto-Suture device is held at 90° to the fascia, as recommended, the surgeon's elbow makes an angle α of about 120° with the his arm; the hand is thus near the end of its rotational travel in that orientation, and its maneuverability is limited.

While the present example is based on skin staples, which are later removed, the principles of operation are similar for internal Auto-Sutures.

Additionally, FIGS. 1E-1F schematically compare internal body seams made by Auto-Suture staples 12 and those made by hand, with a surgical thread, for example, for transverse anastomosis for a stomach 13. As seen in FIG. 1E, sutures 12, made by Auto-Suture staples and forming seams 11, are parallel with the surgical cut. In contrast, as seen in FIG. 1F, sutures 15, made by hand, using a surgical thread and forming seams 17, are generally perpendicular to the cut. The situation of FIG. 1F of sutures that are perpendicular to the cut is preferred, since in FIG. 1E, the sutures may block blood flow across to tissue on the far side f the seam.

U.S. Pat. No. 6,113,611 to Allen et al., "Surgical fastener and delivery system," whose disclosure is incorporated herein by reference, describes a surgical fastener preferably made from a shape memory alloy, which can access internal tissue or other synthetic material through a small surgical access port or incision. After the fastener is deployed through layers of tissue, it assumes a shape of a plurality of closes, that automatically applies to the layers of tissue an appropriate haemostatic compression which is relatively independent of tissue thickness. A delivery instrument for deploying the fastener is also provided. In essence, the surgical fastener, according to U.S. Pat. No. 6,113,611, is a staple-like device, and the delivery instrument for deploying the fastener operates as a stapler, having a rigid bottom plate. The staple pierces the tissue and then encounters the rigid bottom plate, which forces it to close over the tissue.

Yet, because it is designed to apply a haemostatic compression to the layers of tissue, the surgical fastener of U.S. Pat. No. 6,113,611 may cause tissue trauma, by interfering with blood and nutrient flow. In consequence, local necrosis can occur. Furthermore, in some embodiments, one or two sharp leading edges may be exposed, and may cause internal injury.

U.S. Pat. No. 6,517,584, to Lecalve, "Flexible prosthesis in particular for curing hernias by colioscopy," whose disclosure is incorporated herein by reference, describes a flexible prosthesis, in particular for curing hernias by colioscopy. The prosthesis includes at least one anchor device, made of a shape memory material, designed to be deformed merely under temperature control from a storage position into a fixing position, in which the anchor device interferes with the surrounding tissue. The device pierces the tissue at two ends, and forms a loop.

U.S. Pat. No. 5,002,563, to Pyka, et al., "Sutures utilizing shape memory alloys," whose disclosure is incorporated herein by reference, describes a suture and a method for suturing a wound in the tissue. In the preferred embodiment, Pyka, et al. use a needle, of a greater stiffness then the suture, to pierce the tissue. The needle is then cut off, and the suture may be tied, for example, by hand. In consequence, it requires considerable handling, and does not offer a solution to applying sutures in hard-to-reach places, taughtness control, fatigue, and less-skilled surgeons. Furthermore, it does not teach the simultaneous application of multiple sutures. Additionally, the preferred embodiment utilizes a needle, which is generally coarser than the suture, and in consequence, may be traumatic to the tissue.

Endoanchor™, of Johnson and Johnson Co. is a shape memory anchor having a delivery device. However, its application is limited to fixing a mesh or a patch to the tissue.

A shortcoming of the entire available prior art systems are that in order to change the direction of closing, one must change the orientation of application device.

There is thus a widely recognized need for, and it would be highly advantageous to have staplers, staplers, anastomosis devices, and methods for their applications devoid of the above limitations.

SUMMARY OF THE INVENTION

According to one aspect of the present invention, there is provided a stapling element, comprising:

a first shape, adapted for insertion into a tissue, and comprising:
- a tapered portion, forming a sharp, pointed edge, at a proximal end, with respect to the tissue, for piercing the tissue;
- an elongated body, distal to and integral with the tapered portion; and
- a physical feature of the elongated body, for preventing the stapling element from rotating, when in an application shaft, thus maintaining a predetermined closing direction; and a second shape, assumed when the stapling element issues from the application shaft and is inserted into the tissue, the second shape being designed to close into a loop, for forming a staple in the tissue According to an additional aspect of the present invention, the stapling element further comprises a phase of moreover closing the loop, after forming a staple in the tissue.

According to an additional aspect of the present invention, the stapling element has a blunt distal end.

According to an additional aspect of the present invention, the stapling element is adapted for piercing the tissue with minimal tissue crushing.

According to an additional aspect of the present invention, the stapling element is adapted for forming the staple between at least two layers of the tissue.

According to an additional aspect of the present invention, the stapling element is adapted for forming an edge seam.

According to an additional aspect of the present invention, the stapling element is adapted for joining at least two tissue edges, arranged end to end.

According to an additional aspect of the present invention, the stapling element is adapted for joining a tissue and an artificial material, selected from the group consisting of a mesh, a patch, or another material.

According to an additional aspect of the present invention, the stapling element is between about 4 mm and about 140 mm in length.

According to an additional aspect of the present invention, the second shape, designed to close into the loop, forms substantially a closed loop, with the tapered portion, at the proximal end, fitting into a cavity of the distal end.

According to an alternative aspect of the present invention, the second shape, designed to close into the loop, forms substantially a closed loop, with the tapered portion, at the proximal end, arranged against the distal end.

According to an additional aspect of the present invention, the second shape, designed to close into the loop, forms substantially a closed loop, with the tapered portion, at the proximal end, arranged against the distal end, while maintaining the cross sectional diameter of the elongated body.

According to an alternative aspect of the present invention, the second shape, designed to close into the loop, forms an open loop.

According to an alternative aspect of the present invention, the second shape, designed to close into the loop, forms a spiral.

According to an additional aspect of the present invention, the elongated body has a circular cross section, and the physical feature of the elongated body is selected from the group consisting of a rim and a notch, located at least along a distal portion of the elongated body.

According to an alternative aspect of the present invention, the elongated body has a cross section selected from the group consisting of an elliptical cross section and a polygonal cross section, and wherein the cross section is operative as the physical feature of the elongated body, for preventing the stapling element from rotating, when in the application shaft.

According to an additional aspect of the present invention, the tapered portion, forming the sharp, pointed edge is curved in the direction of closing, in the first shape, for piercing the tissue at the angle of closing.

According to an alternative aspect of the present invention, the tapered portion, forming the sharp, pointed edge, has a triangular cross section, adapted for piercing hard tissue.

According to an alternative aspect of the present invention, the tapered portion, forming the sharp, pointed edge, has a circular cross section and a screw thread.

According to an additional aspect of the present invention, the second shape is further designed to close around its longitudinal axis, for piercing the tissue, essentially by self-threading into it.

According to an additional aspect of the present invention, the stapling element is formed of a shape memory alloy.

According to an additional aspect of the present invention, the first shape, adapted for insertion into the tissue, is constrained in a stress-induced martensite phase.

According to an additional aspect of the present invention, the stapling element is formed of a resilient material, wherein the first shape, adapted for insertion into the tissue, is constrained in the first shape.

According to an additional aspect of the present invention, the resilient material is a pure metal.

According to an additional aspect of the present invention, the resilient material is a polymer.

According to an alternative aspect of the present invention, the stapling element is formed as a composite of at least two materials.

According to another aspect of the present invention, there is provided a device for applying staples to a tissue, comprising:

a cartridge, adapted for receiving at least one stapling element, the stapling element comprising:
- a first shape, adapted for insertion into a tissue, and comprising:
  - a tapered portion, forming a sharp, pointed edge, at a proximal end, with respect to the tissue, for piercing the tissue;
  - an elongated body, distal to and integral with the tapered portion; and
  - a physical feature of the elongated body, for preventing the stapling element from rotating, when in an application shaft, thus maintaining a predetermined closing direction; and
- a second shape, assumed when the stapling element issues from the application shaft and is inserted into the tissue, the second shape being designed to close into a loop, for forming a staple in the tissue,
wherein the cartridge is adapted for maintaining the at least one stapling element at a fixed orientation, with respect to a direction of closing of the stapling element;

a mechanism, in mechanical communication with the cartridge, for issuing the at least one stapling element from the cartridge; and a proximal end, with respect to the tissue, having a rigid, proximal-end frame, which defines an opening from which the at least one stapling elements issues.

According to an additional aspect of the present invention, the stapling element further comprises a phase of moreover closing the loop, after forming a staple in the tissue.

According to an additional aspect of the present invention, the device includes a handle, with a finger lever, for controlling the mechanism, wherein the handle is arranged at an angle to the application shaft, to allow a surgeon maximum maneuverability, with a full range of elbow bending.

According to an additional aspect of the present invention, the finger lever is connected to a gripping portion of the handle with a swivel pin, for optimal ease of finger-lever maneuverability.

According to an additional aspect of the present invention, the mechanism for issuing the at least one stapling element from the device is further adapted to issue the at least one stapling element gradually.

According to an additional aspect of the present invention, the rigid, proximal-end frame, which defines the opening from which the at least one stapling element issues, is at angle, which is smaller than 90° to the at least one stapling element.

According to an additional aspect of the present invention, the device includes a counter frame, on a proximal side of the rigid, proximal-end frame, for holding the tissue between the application and counter frames.

According to an additional aspect of the present invention, the counter frame further includes a casing, which defines an inner space, within which the at least one stapling element is designed to close.

According to an additional aspect of the present invention, the device is adapted for endoscopy.

According to an additional aspect of the present invention, the cartridge, adapted for receiving at least one stapling element, is further adapted for receiving a plurality of stapling elements, arranged in a file, and issued one by one, each forming a staple, so that the device is operative as a Self-Closing Stapling, Intermittent-Firing (SCS-IF™) device.

According to an additional aspect of the present invention, the device is adapted for endoscopy, operative as a Self-Closing Stapling, Intermittent-Firing (SCS-IF-ENDO™) device.

According to an alternative aspect of the present invention, the cartridge, adapted for receiving at least one stapling element, is further adapted for receiving a plurality of stapling elements, arranged parallel to each other, as a row, and issued simultaneously, for forming a single seam of a plurality of staples, so that the device is operative as a Self-Closing Stapling-Transverse Anastomosis (SCS-TA™) device.

According to an additional aspect of the present invention, the device is adapted for endoscopy, operative as a Self-Closing Stapling-Transverse Anastomosis Endoscopy (SCS-TA-ENDO™) device.

According to an additional aspect of the present invention, the device includes a knife, for cutting excess tissue along the seam.

According to an alternative aspect of the present invention, the cartridge, adapted for receiving at least one stapling element, is further adapted for receiving a plurality of stapling elements, arranged parallel to each other, as two rows, and issued simultaneously, for forming two parallel seams, each of a plurality of staples, so that the device is operative as a Self-Closing Stapling-Gastro-Intestinal Anastomosis (SCS-GIA™) device.

According to an additional aspect of the present invention, the device is adapted for endoscopy, operative as a Self-Closing Stapling-Gastro-Intestinal Anastomosis Endoscopy (SCS-GIA-ENDO™) device.

According to an additional aspect of the present invention, the device includes a knife, arranged between the two parallel seams, for separating the two parallel seams.

According to an alternative aspect of the present invention, the device is adapted for receiving at least one stapling element, is round, adapted for receiving a plurality of stapling elements, arranged in a circle, parallel to each other, and issued simultaneously, for forming a circular seam of a plurality of staples, so that the device is operative as a Self-Closing Stapling-End-to-End Anastomosis (SCS-EEA™), adapted for endoscopy.

According to an additional aspect of the present invention, the device includes a circular knife, internal to the circular seam.

According to an alternative aspect of the present invention, the cartridge, adapted for receiving at least one staple element, comprises a plurality of staples, and the mechanism is adapted to issue the plurality of staples in parallel, for applying a row of staples simultaneously and gradually, so that device is operative as a Self-Closing Stapling, Simultaneous-Gradual-Firing (SCS-SGF™) device.

According to an additional aspect of the present invention, the device is operative as a Self-Closing Stapling, Simultaneous-Gradual-Firing-Endoscopy (SCS-SGF-ENDO™) device, for applying a row of staples simultaneously and gradually.

According to an additional aspect of the present invention, the device is adapted for the application of a single staple.

According to an alternative aspect of the present invention, the device is operative as a Self-Closing Stapling, Single-Shot (SCS-SS™) device.

According to an additional aspect of the present invention, the device is operative as a Self-Closing Stapling, Single-Shot Endoscopy (SCS-SS-ENDO™) device.

According to an alternative aspect of the present invention, the device has a gripping position and is adapted for changing the predetermined closing direction without changing the gripping position.

According to one aspect of the present invention, there is provided a method of staple application, comprising:
providing at least one stapling element having:
a first shape, adapted for insertion into a tissue, and comprising:
a tapered portion, forming a sharp, pointed edge, at a proximal end, with respect to the tissue, for piercing the tissue;
an elongated body, distal to and integral with the tapered portion; and
a physical feature of the elongated body, for preventing the stapling element from rotating, when in an application shaft, thus maintaining a predetermined closing direction; and
a second shape, assumed when the stapling element issues from the application shaft and is inserted into the tissue, the second shape being designed to close into a loop, for forming a staple in the tissue;
inserting the stapling element into the tissue, via the pointed edge; and allowing the stapling element to close and form the staple According to an additional aspect of the present invention, the stapling element further comprises a phase of moreover closing the loop, after forming a staple in the tissue.

According to an additional aspect of the present invention, the inserting further includes inserting gradually, hence, with minimal tissue crushing.

According to an additional aspect of the present invention, the inserting further includes inserting at angle, which is smaller than 90° to the stapling element.

According to an additional aspect of the present invention, the inserting further includes inserting while maintaining the closing direction of the at least one stapling element.

According to another aspect of the present invention, there is provided a device for applying staples to a tissue, comprising:

a cartridge, adapted for storing at least one stapling element, in a coiled position, the stapling element having a tapered portion, forming a sharp, pointed edge, at a proximal end, with respect to the tissue, for piercing the tissue;

a mechanism, in mechanical communication with the at least one stapling element, for issuing the at least one stapling element from the cartridge; and a proximal end, with respect to the tissue, having a rigid, proximal-end frame, which defines an opening from which the at least one stapling elements issues.

According to an additional aspect of the present invention, the at least one staple comprises a plurality of staples, and the mechanism is adapted to issue the plurality of staples in parallel.

According to an alternative aspect of the present invention, the at least one staple comprises a plurality of staples, and the mechanism is adapted to issue the plurality of staples in series.

According to another aspect of the present invention, there is provided a stapling element, comprising:

a coiled shape, adapted for coiling in a tissue, so as to form a loop; and a tapered portion, forming a sharp, pointed edge, at a proximal end, with respect to the tissue, for piercing the tissue, the staple being formed of a resilient material.

According to another aspect of the present invention, there is provided a method of applying a stapling element into a tissue, comprising:

providing a stapling element, formed of a resilient material and having:
a coiled shape, adapted for coiling in a tissue, so as to form a loop; and
a tapered portion, forming a sharp, pointed edge, at a proximal end, with respect to the tissue, for piercing the tissue; and applying the stapling element into the tissue, while the stapling element remains in a coiled shape.

The present invention successfully addresses the shortcomings of the presently known configurations by providing a stapling element, operative to pierce and penetrate a tissue by a first end, and close around the tissue. The staple is adapted for joining tissue of diverse geometries, for example, joining edge to edge, joining two or more layers together, and joining a mesh, or a patch to the tissue. Three factors help prevent local necrosis: 1. The self-closing feature of the staple does not lead to tissue crushing. 2. Edge seams are applied generally perpendicular to the tissue edge, allowing for blood supply to the tissue edge. 3. Excess tissue is cut off at the seam, minimizing the amount of tissue that may undergo local necrosis. A physical feature prevents the staple from rotating, when in an application shaft, to maintain a predetermined closing direction. The application devices provide ergonomic means for staple application in difficult-to-reach places. In addition, they provide standardization, so that the skilled and the less so may reach results of comparable quality, and the effects of fatigue and loss of patience will be minimized. The wide variety of stapling elements, which come in different sizes and shapes, and the wide variety of devices that are disclosed provide solutions to many surgical problems, for open and minimally invasive surgeries. The stapling element may be formed of an alloy, a pure metal, a polymer, or a composite of at least two materials. Additionally, staples, staplers, anastomosis devices, and methods for their applications are described.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1F are schematic illustrations of the Auto Staple Instrument and staples, as known;

FIGS. 2A-2E schematically illustrate a stapling element, in accordance with a preferred embodiment of the present invention;

FIGS. 3A-3H schematically illustrate stapling elements of other cross sections, in accordance with other embodiments of the present invention;

FIGS. 4A-4E schematically illustrate a stapling element, of circular cross sections, whose tapered portion has a screw thread, in accordance with an embodiment of the present invention;

FIG. 5 schematically illustrates a stapling element, of circular cross sections, with a screw thread along most of its length, for self-threading into a tissue, in accordance with an embodiment of the present invention;

FIGS. 6A-6B schematically illustrate a stapling element, whose tapered portion is curved in the direction of closing, in accordance with an embodiment of the present invention;

FIGS. 7A-7F schematically illustrate stapling elements, wherein cavities are not provided at the distal ends, in accordance with other embodiments of the present invention;

FIGS. 15A-15H schematically illustrate stapling elements of various cross sections, in accordance with embodiments of the present invention;

FIGS. 16A-16H schematically illustrate application shafts of various cross sections, suitable for the embodiments of FIGS. 15A-15H;

FIGS. 18A-18K schematically illustrate the components of an application shaft, in accordance with an embodiment of the present invention;

FIGS. 20A-20C schematically illustrate example applications of stapling elements, by the SCS-IF™ device of FIGS. 19A-19F, in accordance with embodiments of the present invention;

FIGS. 22A-22H schematically illustrate a Self-Coiling Staple-Transverse Anastomosis (SCS-TA™) device, for using stapling elements, in accordance with an embodiment of the present invention;

FIGS. 25A-25F schematically illustrate a Self-Coiling Staple-End to End Anastomosis (SCS-EEA™) device, for using stapling elements, in accordance with an embodiment of the present invention;

FIGS. 28A-28J schematically illustrate a Self-Closing Stapling, Simultaneous-Firing (SCS-SF™) device, using stapling elements, in accordance with an embodiment of the present invention;

FIGS. 30A-30D schematically illustrate a stapling element, formed as a composite of at least two materials, in accordance with another embodiment of the present invention; and FIGS. 31A-31C schematically illustrate an application shaft for inserting staples while in a coiled shape, in accordance with still another embodiment of the present invention.

DESCRIPTION OF THE PREFERRED EMBODIMENTS

Figure 8A:
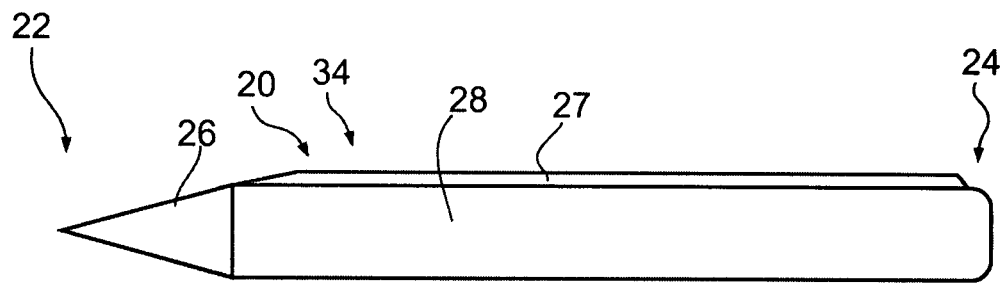
FIGS. 8A-8C schematically illustrate a stapling element, wherein a cavity is not provided at its distal end, in accordance with still other embodiments of the present invention.

The present invention is a stapling element, operative to pierce and penetrate a tissue by a first end, and close around the tissue. The staple is adapted for joining tissue of diverse geometries, for example, joining edge to edge, joining two or more layers together, and joining a mesh, or a patch to the tissue. Three factors help prevent local necrosis: 1. The self-closing feature of the staple does not lead to tissue crushing. 2. Edge seams are applied generally perpendicular to the tissue edge, allowing for blood supply to the tissue edge. 3. Excess tissue is cut off at the seam, minimizing the amount of tissue that may undergo local necrosis. A physical feature prevents the staple from rotating, when in an application shaft, to maintain a predetermined closing direction. The application devices provide ergonomic means for staple application in difficult-to-reach places. In addition, they provide standardization, so that the skilled and the less so may reach results of comparable quality, and the effects of fatigue and loss of patience will be minimized. The wide variety of stapling elements, which come in different sizes and shapes, and the wide variety of devices that are disclosed provide solutions to many surgical problems, for open and minimally invasive surgeries. The stapling element may be formed of an alloy, a pure metal, a polymer, or a composite of at least two materials. Additionally, staples, staplers, anastomosis devices, and methods for their applications are described.

The principles and operation of the device and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 2A-2E schematically illustrate a stapling element 20, in accordance with a preferred embodiment of the present invention. Stapling element 20 includes an elongated body 28 and proximal and distal ends 22 and 24, respectively, with respect to the tissue (not shown). FIGS. 2A-2D illustrate proximal, side, distal, and pictorial views, respectively, of stapling element 20, when in a first shape 34, while FIG. 2E illustrates a side view, when in a second shape 36. Stapling element 20 is adapted to close, in the direction of an arrow 38 (FIG. 2E), from first shape 34 into second shape 36, upon release.

As seen in FIGS. 2B and 2D, stapling element 20 includes a tapered portion 26 at proximal end 22, forming a sharp, pointed edge 32, operative as a needle, for piercing a tissue. Generally, stapling element 20 is blunt at distal end 24. However, in accordance with the present invention, this condition is not necessary, as will be illustrated hereinbelow, for example, in conjunction with FIG. 7A.

As seen in FIGS. 2B and 2C, stapling element 20 may further include a cavity 30, at distal end 24, adapted for receiving tapered portion 26, so as to form a closed loop.

As seen in FIG. 2E, as proximal and distal ends 22 and 24 come together, in second shape 36, tapered portion 26 may fit into cavity 30, forming a closed loop, with no exposed sharp edges.

A physical feature, such as a rim 27, which appears as a protrusion on cross sectional views 2A and 2C, and which may extend the length of elongated body 28, as seen in FIGS. 2B and 2D, or cover a portion of its distal end, ensures that stapling element 20 is inserted into the tissue at a specific, predetermined orientation with respect to its memorized closing. For example, as seen in FIG. 2E, rim 27 may form an outer ring over closed second shape 36. Rim 27 may fulfill two purposes:

i. it serves as a visible indicator of the direction of closing; and
  ii. it prevents stapling element 20 from rotating away from its predetermined orientation, within an application shaft.

It will be appreciated that a notch or any other means for ensuring a specific, orientation-dependent insertion, by fulfilling purposes (i) and (ii), may similarly be used. It will be further appreciated that stapling element 20 may include two or more physical features, such as two rims 27 or two notches (for example, as shown in conjunction with FIG. 15D, hereinbelow. It will be appreciated that the application shaft compliments the at least one physical feature of stapling element 20, as will be described hereinbelow, for example, in conjunction with FIG. 16D, hereinbelow.

A total length L of stapling element 20 depends on the required application, and may vary, for example, between about 4 mm and about 200 mm. A length T of tapered portion 26 may be, for example, between about 0.5 mm and about 5 mm. A diameter d similarly depends on the application, and may vary, for example, between about 0.1 and about 3 mm, and preferably between about 0.5 and about 2 mm. It will be appreciated that other values, which may be smaller or larger, are similarly possible.

It will be appreciated that generally in the art, for blood vessels, stapling elements of 4 mm are used, and they are color coded white. For the gastrointestinal tract, stapling elements of 5 mm are used, and they are color coded blue. For the stomach, stapling elements of 6 mm are used, and they are color coded green. It will be appreciated that the stapling elements of the present invention may follow the color code that is used in the art. Additionally, stapling elements of other sizes may be used, and may be color coded by other colors.

Stapling element 20 may be formed of a shape memory alloy, wherein first shape 34 is its martensitic shape, either in the martensitic phase, in the fully martensitic temperature range, or in a constrained state, as stress-induced martensite, in the fully austenitic temperature range.

In accordance with a preferred embodiment of the present invention, stapling element 20 is fully austenitic at room temperature, and is maintained at a constrained state, as stress-induced martensite, for insertion into the body, so that adjustment from first shape 34 to second shape 36 may be substantially instantaneous.

Preferably, second shape 36 is in the fully austenitic phase and temperature range.

In accordance with an alternative embodiment of the present invention, stapling element 20 is designed as a resilient spring, formed of a biologically compatible material, such as titanium, tantalum, or stainless steel, a tough, resilient polymer, or another suitable material, which may be constrained into first shape 34, and which is adapted to close into second shape 36, upon release.

While the present embodiment illustrates both elongated body 28 and tapered portion 26 of circular cross sections, it will be appreciated that many other cross sections are possible.

Referring further to the drawings, FIGS. 3A-3H schematically illustrate stapling elements 20 of other cross sections, in accordance with other embodiments of the present invention.

As seen in FIGS. 3A-3D, elongated body 28 has a circular cross section, and tapered portion 26 has a triangular cross section. Cavity 30 is thus also triangular, for receiving triangular tapered portion 26. The triangular cross section of tapered portion 26 is operative to cut into a hard tissue, such as a tendon or a bone.

As seen in FIGS. 3E-3H, elongated body 28 may have a rectangular cross section, and tapered portion 26 may have a triangular cross section. It will be appreciated that the geometry of the present embodiment inherently ensures that stapling element 20 is inserted into the tissue at a specific, predetermined orientation with respect to its memorized closing, since the rectangular cross section prevents stapling element 20 from rotating away from its predetermined orientation, within an application shaft. Additionally, triangular cavity 30, shaped as an arrow head (FIG. 3G), may serve as a visible indicator of the direction of closing. Additionally or alternatively, a visible marking 44 may be applied to distal end 24, as an indicator of the direction of closing. Thus rim 27 (FIGS. 2A-2E) need not be used. It will be appreciated that visible marking 44 need not be applied, since in general, stapling elements 20 are loaded onto the cartridge or application shaft at the factory.

It will be appreciated that elongated body 28 may have other cross sections, for example, elliptical, triangular, or of other polygons, and generally, these cross sections will prevent stapling element 20 from rotating away from its predetermined orientation, within an application shaft. Similarly, tapered portion 26 may have other cross sections, for example, elliptical, triangular, or of other polygons. Furthermore, elongated body 28 and tapered portion 26 may have similar cross sections or different cross sections.

In general, the different cross sections are adapted for different applications. For example, a circular cross section causes minimal trauma, but an elliptical cross section has greater strength, and a triangular cross section is operable for penetrating hard tissue, such as tendon or bone.

Referring further to the drawings, FIGS. 4A-4E schematically illustrate stapling element 20, of circular cross sections, wherein tapered portion 26 has a screw thread 42, in accordance with an embodiment of the present invention.

Accordingly, the release from first shape 34 into second shape 36 involves both a closing motion, in the direction of arrow 38 (FIG. 4E) and a threading motion, around the longitudinal axis, in the direction of an arrow 40. Screw-thread 42, when rotating in the direction of arrow 40, facilitates piercing the tissue with greater ease, both for hard and soft tissue, essentially by self-threading into it.

Referring further to the drawings, FIG. 5 schematically illustrates stapling element 20, of circular cross sections, with screw thread 42 along most of its length, for self-threading into a tissue, in accordance with an embodiment of the present invention. To accommodate thread 42, rim 27 is provided only at the distal portion of elongated body 28. The present embodiments may be applicable to a hard tissue, such as tendon and bone.

Referring further to the drawings, FIGS. 6A-6B schematically illustrate stapling element 20, wherein tapered portion 26, forming the sharp, pointed edge, is curved in the direction of closing, in first shape 34, in accordance with an embodiment of the present invention. The advantage of this design is that proximal end 22 pierces the tissue at the angle of closing, even when only partially, and perhaps only slightly issued from the application shaft. Additionally, tapered portion 26, which is pointed in the direction of closing, may also be used as a visible indication of the direction of closing.

Referring further to the drawings, FIGS. 7A-7F schematically illustrate stapling element 20, wherein cavity 30 (FIGS. 6A-6B) is not provided at distal end 24. Rather, tapered portion 26 and distal end 24 are arranged to overlap, in accordance with other embodiments of the present invention.

As seen in FIGS. 7A-7B, proximal and distal ends 22 and 24 come together, while substantially maintaining the cross sectional size of elongated body 28. It will be appreciated that the line of overlap between proximal and distal ends 22 and 24 may be perpendicular to the plane of the closed staple, as shown in FIG. 7B, or at any angle thereof.

Thus, in accordance with the embodiment of FIGS. 7A and 7B, stapling element 20 is symmetrical with respect to its proximal and distal ends, and may be inserted from either.

As seen in FIGS. 7C-7D, distal end 24 may be somewhat blunt.

As seen in FIGS. 7E-7F, distal end 24 may be blunt.

Figures 8B, 8C:
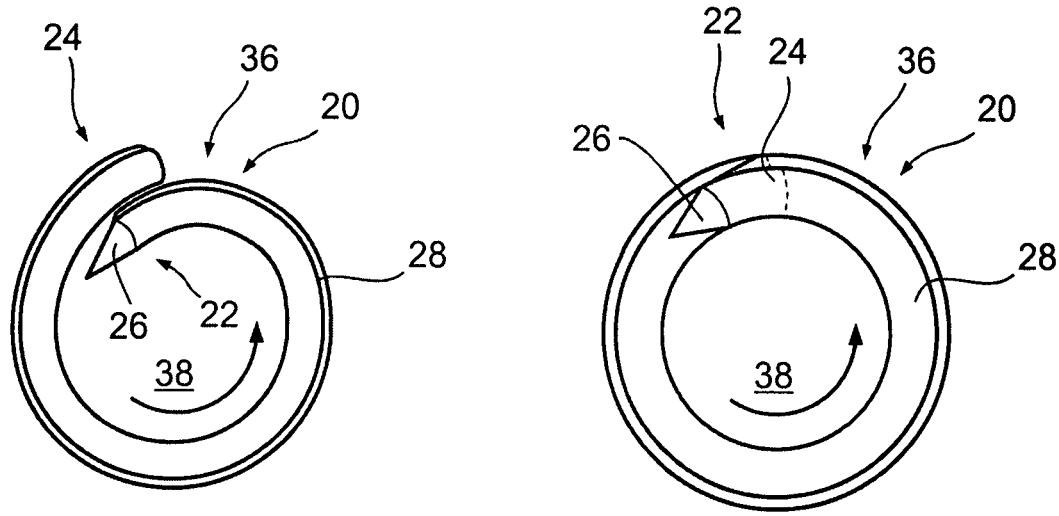

Referring further to the drawings, FIGS. 8A-8C schematically illustrate stapling element 20, wherein again, cavity 30 (FIGS. 6A-6B) is not provided at distal end 24, and tapered portion 26 and distal end 24 are arranged to overlap, in accordance with another embodiment of the present invention. As seen in FIG. 8B, tapered portion 26 is internal to the loop. Alternatively, it may be external to the loop. As seen in FIG. 8C, tapered portion 26 is alongside distal portion 24. Alternatively, stapling element 20 may form an open loop or an open spiral.

Referring further to the drawings, FIGS. 9A-9I schematically illustrate various manners of closure of stapling elements 20 when in second shape 36, in accordance with the present invention.

Figure 9A:
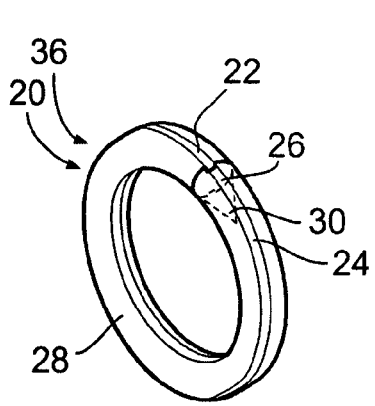
FIGS. 9A-9I schematically illustrate various manners by which the proximal and distal ends may come together, for stapling elements in the second shape, in accordance with the present invention.

As seen in FIG. 9A, tapered portion 26 fits into cavity 30 of distal end 24.

Figure 9B:
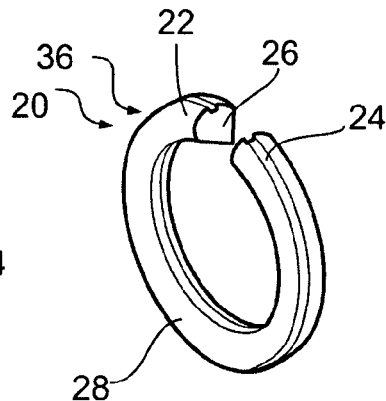

As seen in FIG. 9B, cavity 30 is not provided, and tapered portion 26 touches distal end 24.

Figure 9C:
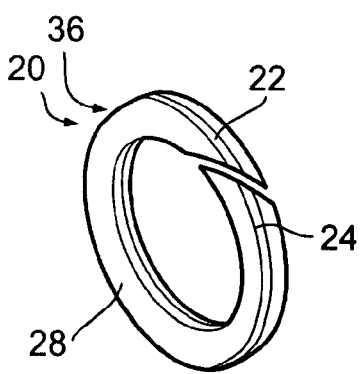

As seen in FIG. 9C, proximal and distal ends 22 and 24 are symmetric. They overlap, while substantially maintaining the cross section of elongated body 28.

Figure 9D:
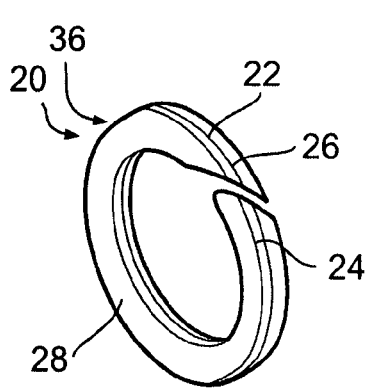

As seen in FIG. 9D, distal end 24 is slightly blunt, and proximal and distal ends 22 and 24 overlap, while substantially maintaining the cross section of elongated body 28.

Figure 9E:
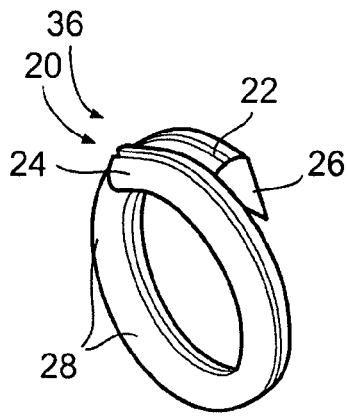

As seen in FIG. 9E, proximal and distal ends 22 and 24 overlap to form a closed loop, and are arranged end to end. This embodiment is applicable regardless of whether cavity 30 is provided.

Figure 9F:
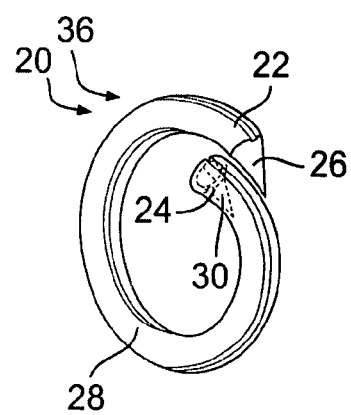

As seen in FIG. 9F, proximal and distal ends 22 and 24 overlap to form a closed loop, with distal end 24 being internal to the loop. Again, this embodiment is applicable regardless of whether cavity 30 is provided.

Figure 9G:
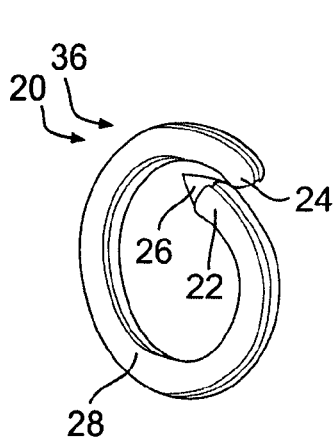

As seen in FIG. 9G, proximal and distal ends 22 and 24 overlap to form a closed loop, with distal end 24 being external to the loop. As before, this embodiment is applicable regardless of whether cavity 30 is provided.

Figure 9H:
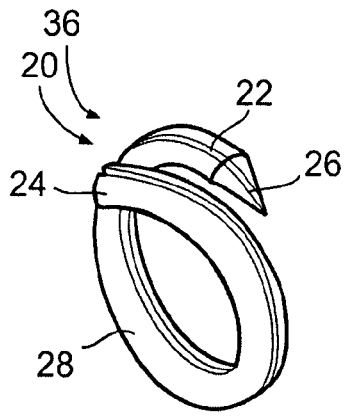

As seen in FIG. 9H, proximal and distal ends 22 and 24 overlap to form an open spiral. This embodiment is applicable regardless of whether cavity 30 is provided.

Figure 9I:
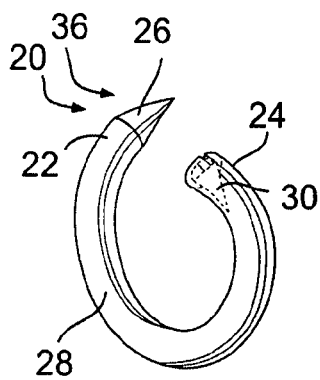
Figure 11A:
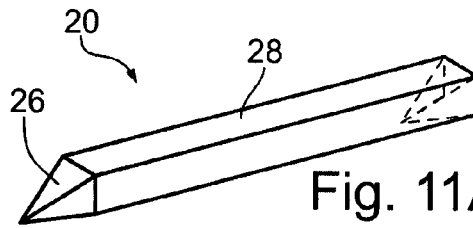
FIGS. 11A-11G schematically illustrate stapling elements, in the first shape, with various geometrical cross sections, in accordance with other embodiments of the present invention.
Figure 10A:
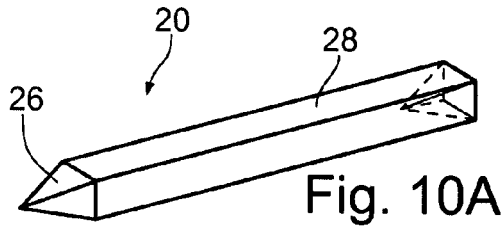
FIGS. 10A-10G schematically illustrate stapling elements, in the first shape, with various geometrical cross sections, in accordance with other embodiments of the present invention.
Figure 11B:
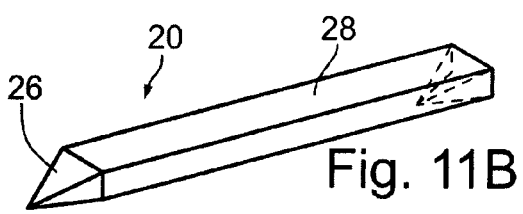
Figure 10B:
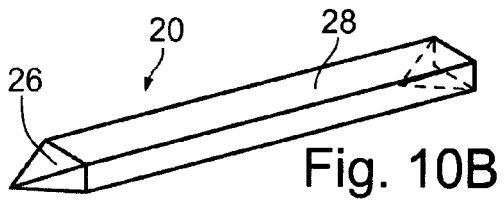
Figure 11C:
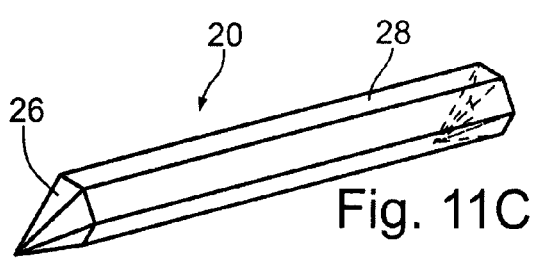
Figure 10C:
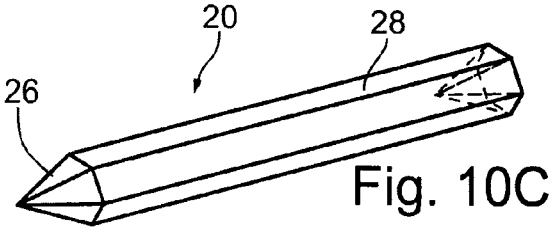
Figure 11D:
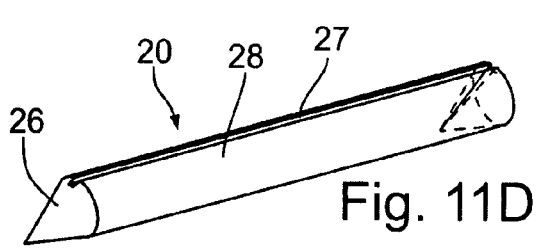
Figure 10D:
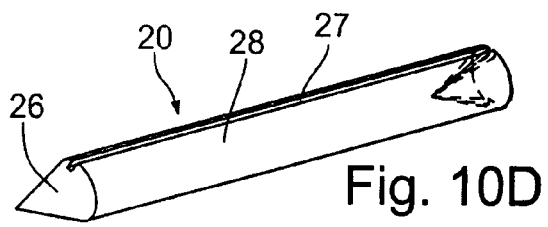
Figure 11E:
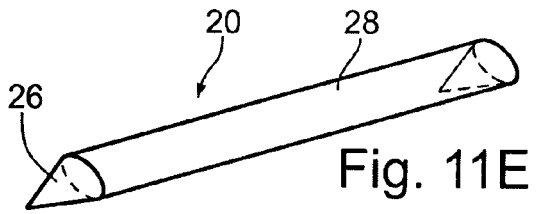
Figure 10E:
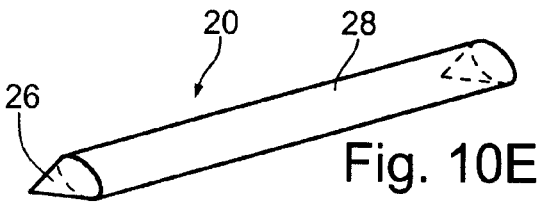
Figure 11F:
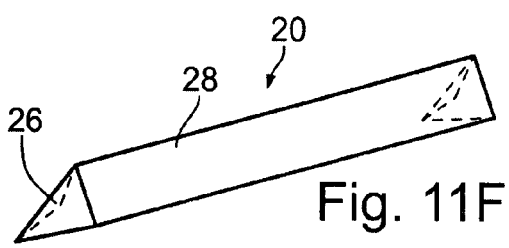
Figure 10F:
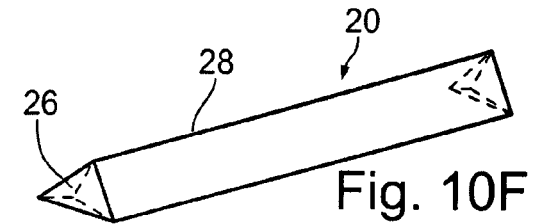
Figure 11G:
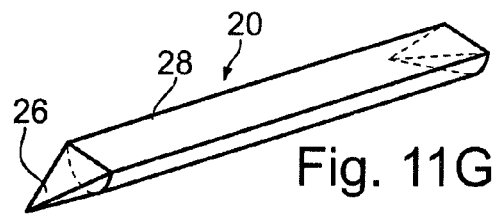
Figure 10G:
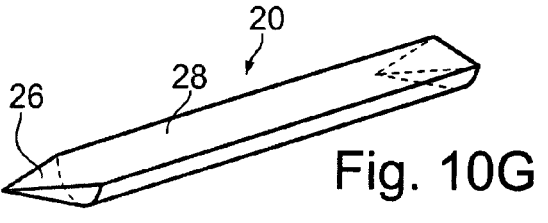

As seen in FIG. 9I, stapling element 20 forms an open loop. This embodiment is applicable regardless of whether cavity 30 is provided.

It will be appreciated that the embodiments of FIGS. 9A-9I relate to any cross section, such as circular, square, triangular, elliptical or any other may be used.

Referring further to the drawings, FIGS. 10A-10G schematically illustrate stapling elements 20, with elongated bodies 28 and tapered portions 26 of various geometrical cross sections, such as square, rectangular, tetrahedron, circular with a rim, elliptical, and triangular, in accordance with other embodiments of the present invention. In accordance with the present embodiments, the cross sections of elongated bodies 28 and tapered portions 26 are similar, for example, both may be triangular, or square. In accordance with other embodiments of the present invention, they may be different.

It will be appreciated that these geometrical cross sections inherently prevent stapling element 20 from rotating within an application shaft. In some cases, for example, with regard to any triangle, especially one that is not isogonic, the pointed edge may be further used as a visible indicator of the direction of closing. Additionally or alternatively, a visible marking 44 (FIG. 3G) may be applied to distal end 24 as an indicator of the direction of closing.

Referring further to the drawings, FIGS. 11A-11G schematically illustrate stapling elements 20 of various geometrical cross sections, as in FIGS. 10A-10G, wherein tapered portions 26 are as was taught hereinabove, by FIG. 7A, in accordance with embodiments of the present invention.

Figure 12A:
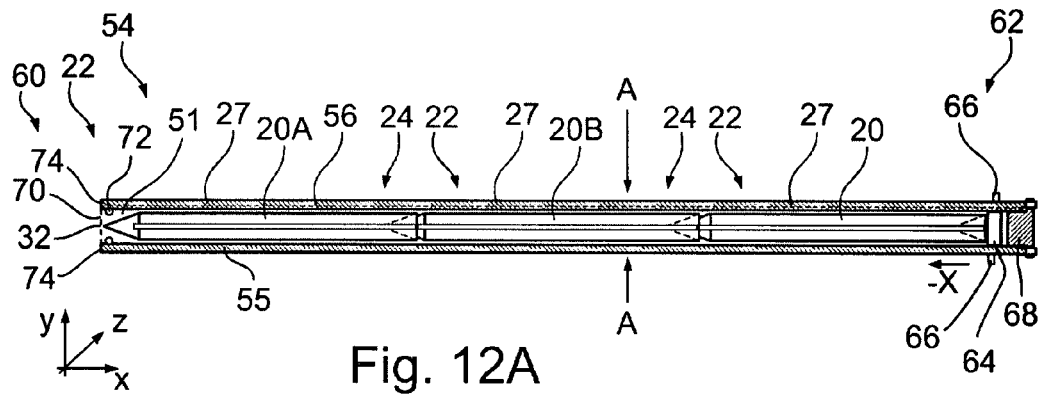
FIGS. 12A-12C schematically illustrate a first shaft of a staple device, in accordance with an embodiment of the present invention.
Figures 12B, 12C:
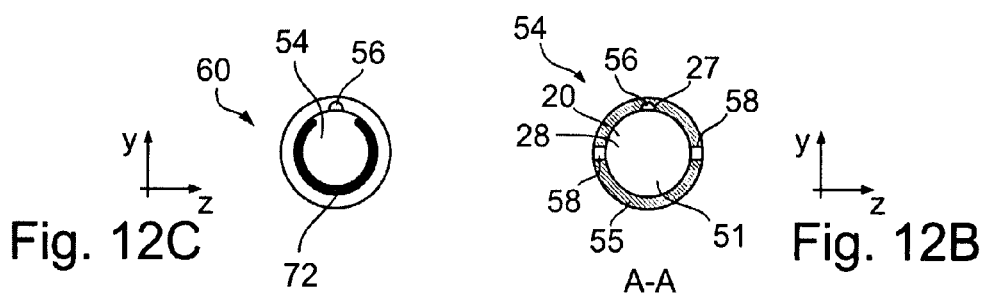

Referring further to the drawings, FIGS. 12A-12C schematically illustrate a first shaft 54 of a staple device, in accordance with embodiments of the present invention. In essence, first shaft 54 is operative as a cartridge for stapling elements 20.

As seen in FIG. 12A, illustrating a side view, in an x;y plane, first shaft 54 has a cladding 55, which defines a lumen 51 and proximal and distal ends 60 and 62, with respect to the tissue (not shown). First shaft 54 further defines an opening 70, encased within a first frame 74, at proximal end 60. First frame 74 includes a preferably spring-operated gate 72, for preventing stapling elements 20 from issuing, unintentionally.

First shaft 54 is adapted to receive at least one, and preferably, several stapling elements 20, arranged in file, so that distal end 24 of a first stapling element 20A is abut against proximal end 22 of a second stapling element 20B.

Furthermore, first shaft 54 is adapted to receive a driving component 64, distal to the file of stapling elements 20, and having two pegs 66, arranged 180° apart. A cap 68 closes or locks first shaft 54, at distal end 62, to prevent an accidental exist of stapling elements 20 and driving component 64.

Pegs 66 of driving component 64 are adapted for transferring a motion, in the −x direction (from distal end 62 to proximal end 60) to stapling elements 20, thus forcing them to issue. It will be appreciated that many alternative mechanical means are known for producing such a motion, and these are also within the scope of the present invention.

As seen in FIG. 12B, illustrating a cross-sectional view A-A, in a y;z plane, first shaft 54 defines lumen 51 whose cross section substantially complements that of elongated body 28 of stapling element 20. Thus, first shaft 54 maintains the specific, predetermined, orientation-dependent insertion of stapling element 20. FIG. 12B further illustrates two slits 58, arranged 180° apart, along the length of first shaft 54, for pegs 66 (FIG. 12A).

As seen in FIG. 12C, illustrating a view from proximal end 60, first shaft 54 includes spring-operated gate 72 at proximal end 60. Preferably, spring-operated gate 72 is formed as an arc, that may open under pressure, as stapling element 20 is forced towards proximal end 60. When closed, spring-operated gate 72 prevents the exit of stapling elements 20.

In accordance with the embodiment of FIGS. 12A-12C, elongated body 28 of stapling element 20 has a circular cross section and includes a feature, formed as rim 27, and first shaft 54 has a complementary circular lumen and includes a complementary shaft feature 56, such as a notch 56, adapted to receive rim 27. It will be appreciated that other cross sections and complementary lumens of first shaft 54 are possible.

It will be appreciated that a feature of stapling element 20 may be formed as a notch, and complementary shaft feature 56, may be formed as protrusion 56, adapted to fit into a notch. It will be appreciated that other complementary systems may similarly be used.

Figures 13A, 13B, 13C:
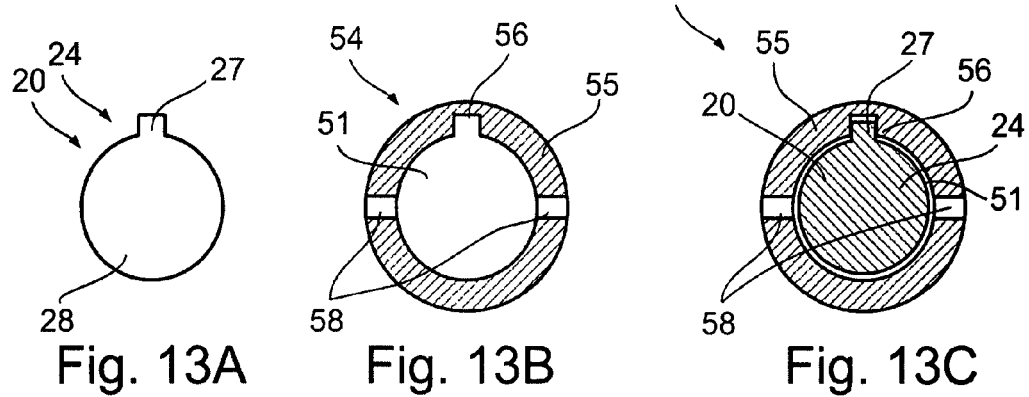
FIGS. 13A-13C and FIGS. 14A-14C schematically compare circular and rectangular cross sections, of stapling elements and of application shafts, according to two embodiments of the present invention.
Figures 14A, 14B, 14C:
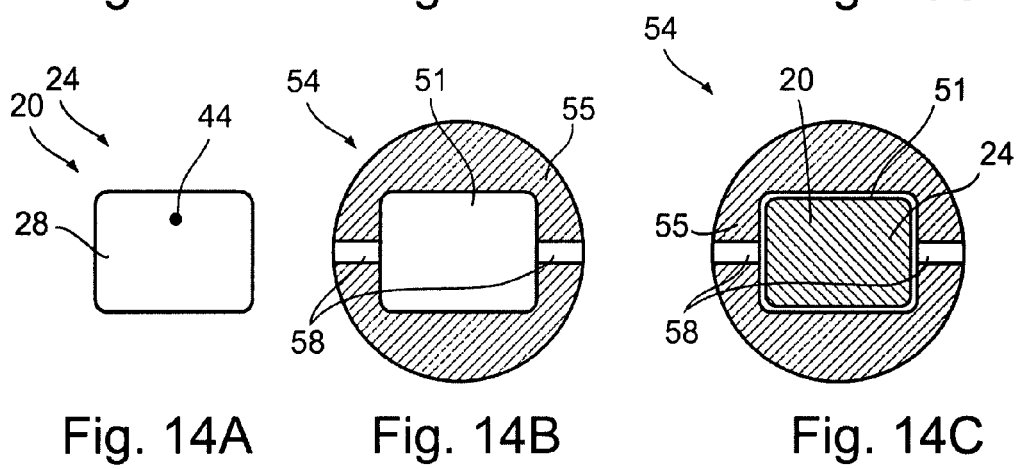

Referring further to the drawings, FIGS. 13A-13C and 14A-14C schematically compare circular and rectangular cross-sections, in accordance with embodiments of the present invention. As seen in FIGS. 13A-13C, elongated body 28 is circular, and includes rim 27, while cladding 55 of first shaft 54 defines circular lumen 51, and includes notch 56 for receiving rim 27. As seen in FIGS. 14A-14C, elongated body 28 is rectangular, and cladding 55 of first shaft 54 defines rectangular lumen 51, adapted to receive it. Additionally, distal end 24 of rectangular stapling element 20 (FIG. 14A) may include visible marking 44, to indicate the direction of closing.

Referring further to the drawings, FIGS. 15A-15H schematically illustrate stapling elements 20 of various cross sections for elongated bodies 28, in accordance with embodiments of the present invention, while FIGS. 16A-16H schematically to illustrate application shafts 54 of matching cross sections of lumens 51.

Figure 17A:
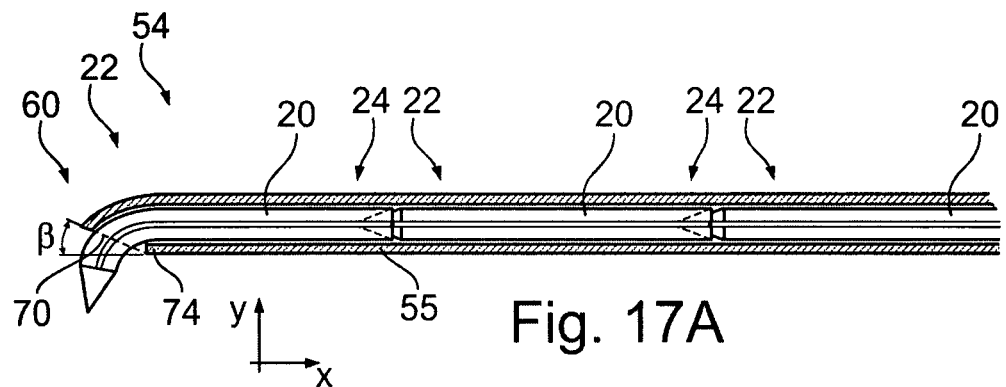
FIGS. 17A-17D illustrate a first shaft having an opening at an angle different than 90°, to the stapling elements, in accordance with embodiments of the present invention.
Figure 17B:
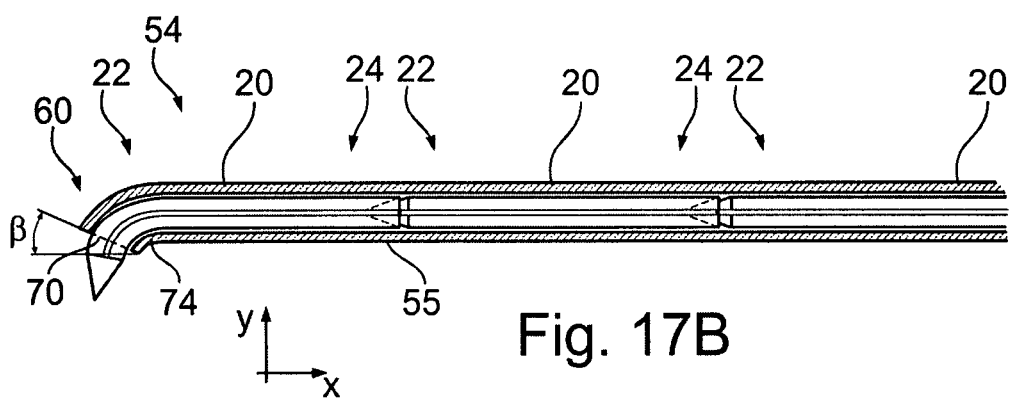
Figure 17C:
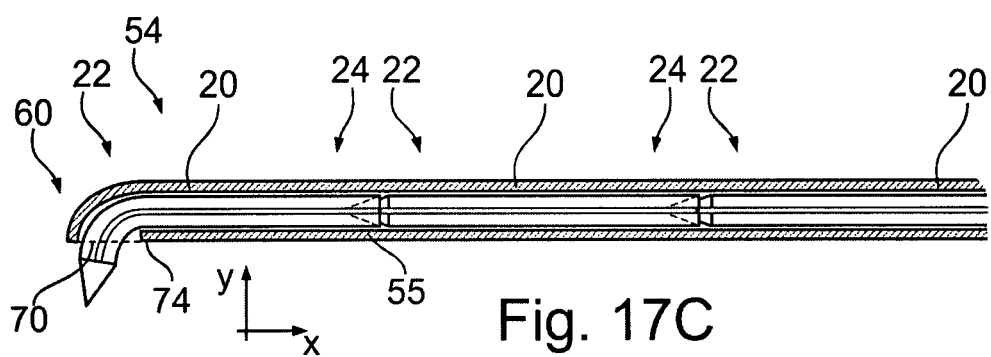
Figure 17D:
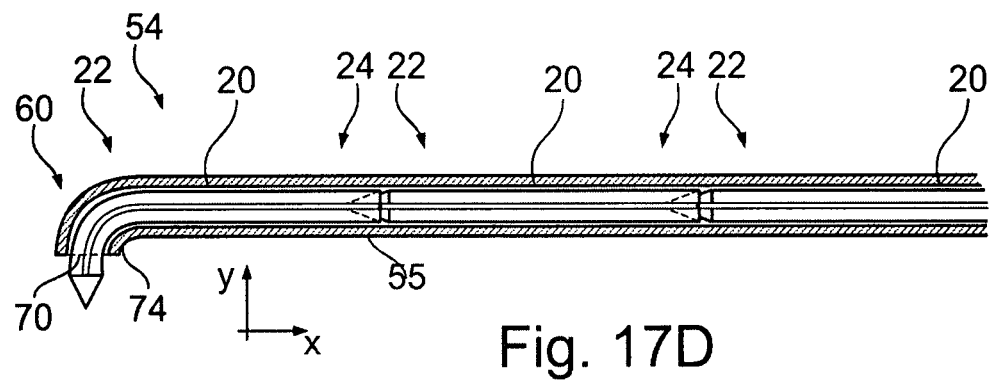

Referring further to the drawings, FIGS. 17A and 17D illustrate first shaft 54 with first frame 74 arranged so that opening 70 forms an angle β, different than 90°, with stapling element 20. Angle β may be, for example, 75°, 45°, or 15°, or any other angle. As seen in FIGS. 17C-17D, angle β may be 0. It will be appreciated that gate 72 (FIG. 12A) is adapted to the angle of frame 74.

The present embodiments are applicable to situations where the tissue is not at a right angle to the application shaft.

Referring further to the drawings, FIGS. 18A-18K schematically illustrate the components of an application shaft 110, in accordance with an embodiment of the present invention.

FIGS. 18A and 18B are pictorial views of first shaft 54, illustrating its components:

at proximal end 60, opening 70 is encased within first frame 74, which includes gate 72, preferably spring-operated;

along the body of first shaft 54, a plurality of stapling elements 20 are arranged in a single file, for issuing in series, one after the other, each being engaged with first shaft 54 by a staple feature and complementary shaft feature 56;

more distal to plurality of stapling elements 20, and abut against them, driving component 64 is engaged with first shaft 54, via pegs 66, which are inserted into slits 58; and at distal end 62, cap 68 which may include a locking mechanism, locks the components within.

Note that a proximal portion 63 does not include slits 58, thus maintaining the integrity of first shaft 54 as a tube.

As seen in FIG. 18C, a second shaft 80, having a cladding 85 with an internal threaded groove 86, defines proximal and distal ends 82 and 84 and a lumen. Second shaft 80 is adapted to receive first shaft 54 within, so that pegs 66 of driving component 64 engage with internal threaded groove 86. Second shaft 80 has a second frame 90, defining an opening at proximal end 82. It will be appreciated that second frame 90 is arranged so as to accommodate the angle of first frame 74 in the embodiments of FIGS. 12A and 17A-17D.

Additionally, second shaft 80 includes a gear 88, at distal end 84. Preferably, the teeth of gear 88 are at an acute angle δ to the y-axis. Gear 88 is fixed onto second shaft 80. As gear 88 rotates, second shaft 80 rotates with it.

As seen in FIG. 18D, a third shaft 100 has a cladding 105 and defines proximal and distal ends 102 and 104, respectively, and a lumen, adapted to receive second shaft 80. A third frame 103 defines an opening at distal end 102. It will be appreciated that both third frame 103 and second frame 90, are arranged so as to accommodate the angle of first frame 74 in any one of the embodiments of FIGS. 12A and 17A-17D.

As seen in FIG. 18E, first shaft 54 is adapted for insertion into second shaft 80, which in turn is adapted for insertion into third shaft 100.

As seen in FIGS. 18F and 18G, third shaft 100 includes a locking device 108, at proximal end 102, which locks third shaft 100 with first shaft 54, to prevent first shaft 54 from rotation, as gear 88 (FIG. 18C) rotates second shaft 80. It will be appreciated that any locking mechanism, as known, may be used.

As seen in FIGS. 18I, 18J and 18D, a dial 106, rigidly connected to third shaft 100, has an indication, for example "UP," which is designed to show the direction of closing of stapling element 20. As stapling element 20 issues from third shaft 100, it will close in the direction of the indication, such as, "UP." Since third shaft 100 and first shaft 54 are rigidly connected by closure device 108, rotating dial 106 will rotate first shaft 54 with third shaft 100, so as to maintain the correspondence between the direction of the indication, such as, "UP" and the direction of closing.

As seen in FIGS. 18H-18I, gear 88 of second shaft 80 is not engaged with dial 106 of third shaft 100, and its rotation does not affect the orientation of dial 106.

FIGS. 18H-18J schematically illustrate application shaft 110, formed of first, second and third shafts 54, 80 and 100. Application shaft 110 defines proximal and distal ends 112 and 114 with respect to the tissue, and a rigid, proximal-end frame 116, which defines an opening, from which stapling elements 20 issue. FIGS. 18H-18J illustrate tapered portion 26 of a first stapling element 20, as it issues from application shaft 110. It will be appreciated that rigid, proximal-end frame 116 is arranged so as to accommodate the angle of first frame 74 in any one of the embodiments of FIGS. 12A, 17A, and 17B.

FIG. 18K schematically illustrates a cross-sectional view of application shaft 110, formed of first, second and third shafts 54, 80 and 100, and driving component 64, with pegs 66 inserted into slits 58. Note that in the present embodiment, driving component 64, like stapling elements 20, includes a notch into which protrusion 56 is inserted.

In accordance with the present invention, the design of first, second and third shafts 54, 80 and 100 is adapted for transferring a motion in the x direction to pegs 66, as illustrated by FIG. 18H. As gear 88 is made to rotate, as shown by an arrow 118, second shaft 80 rotates with it. Pegs 66 are engaged with internal threaded groove 86 of second shaft 80 (FIG. 18C), but are prevented from rotating with second shaft 80, since they are inserted into through, longitudinal slits 58 of first shaft 54 (FIG. 18A), which is fixed by locking device 108 (FIGS. 18F-18G). Hence, pegs 66 must travel along rotating threaded groove 86, sliding in longitudinal slits 58 of first shaft 54, and pushing stapling elements 20, in the −x direction, with them.

It will be appreciated that many alternative mechanical means are known for producing such a motion, and these are also within the scope of the present invention. For example, a piston-cylinder arrangement, or a belt arrangement, which may be a time belt arrangement, or any other known mechanism for producing a linear motion, may be used.

Referring further to the drawings, FIGS. 19A-19F schematically illustrate a Self-Closing Stapling, Intermittent-Firing (SCS-IF™) device 120, formed of application shaft 110 and a gripping handle 130, in accordance with an embodiment of the present invention.

Figure 19A:
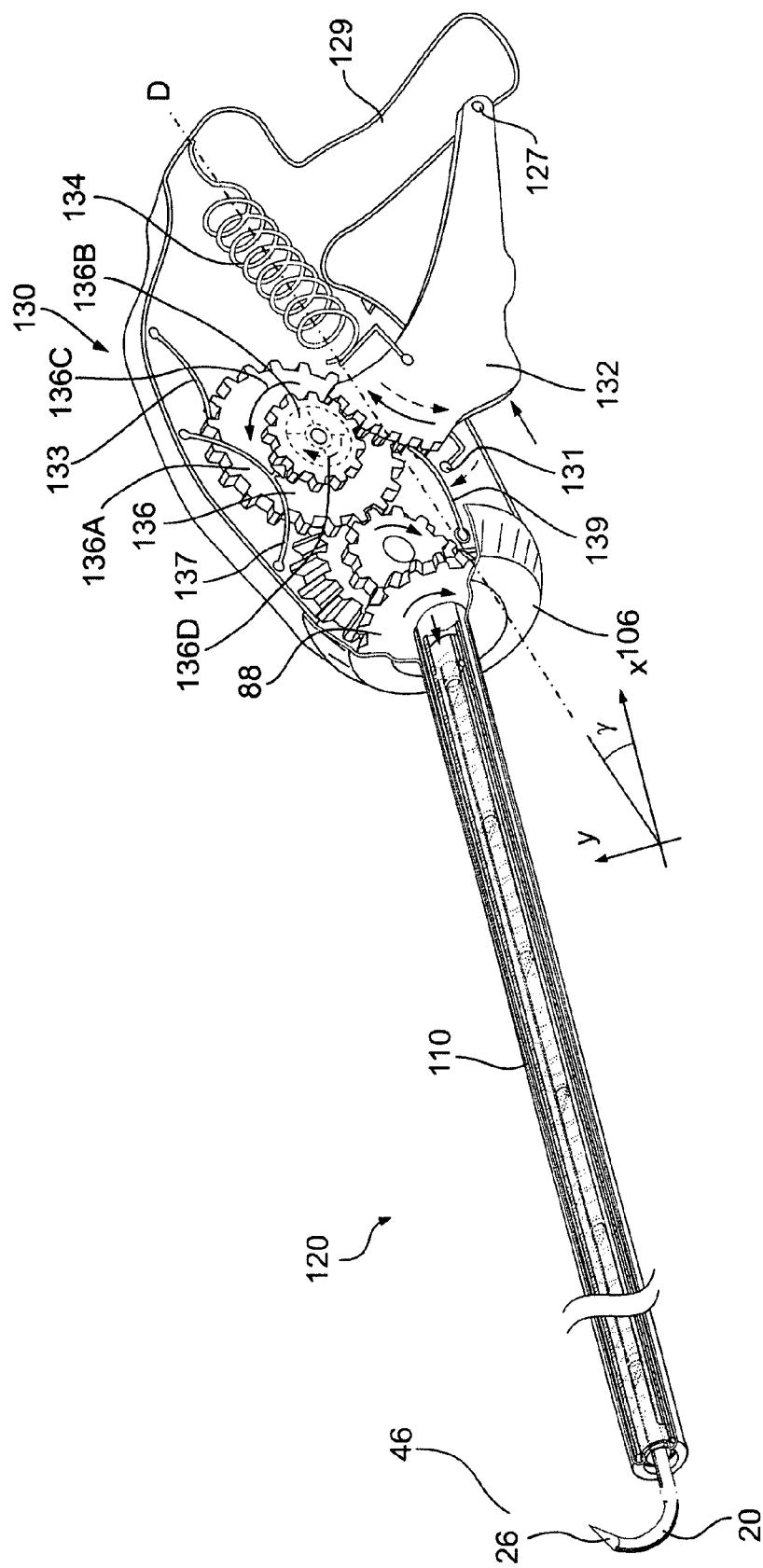
FIGS. 19A-19F schematically illustrate a Self-Closing Stapling, Intermittent-Firing (SCS-IF™) device, in accordance with an embodiment of the present invention.
Figure 19B:
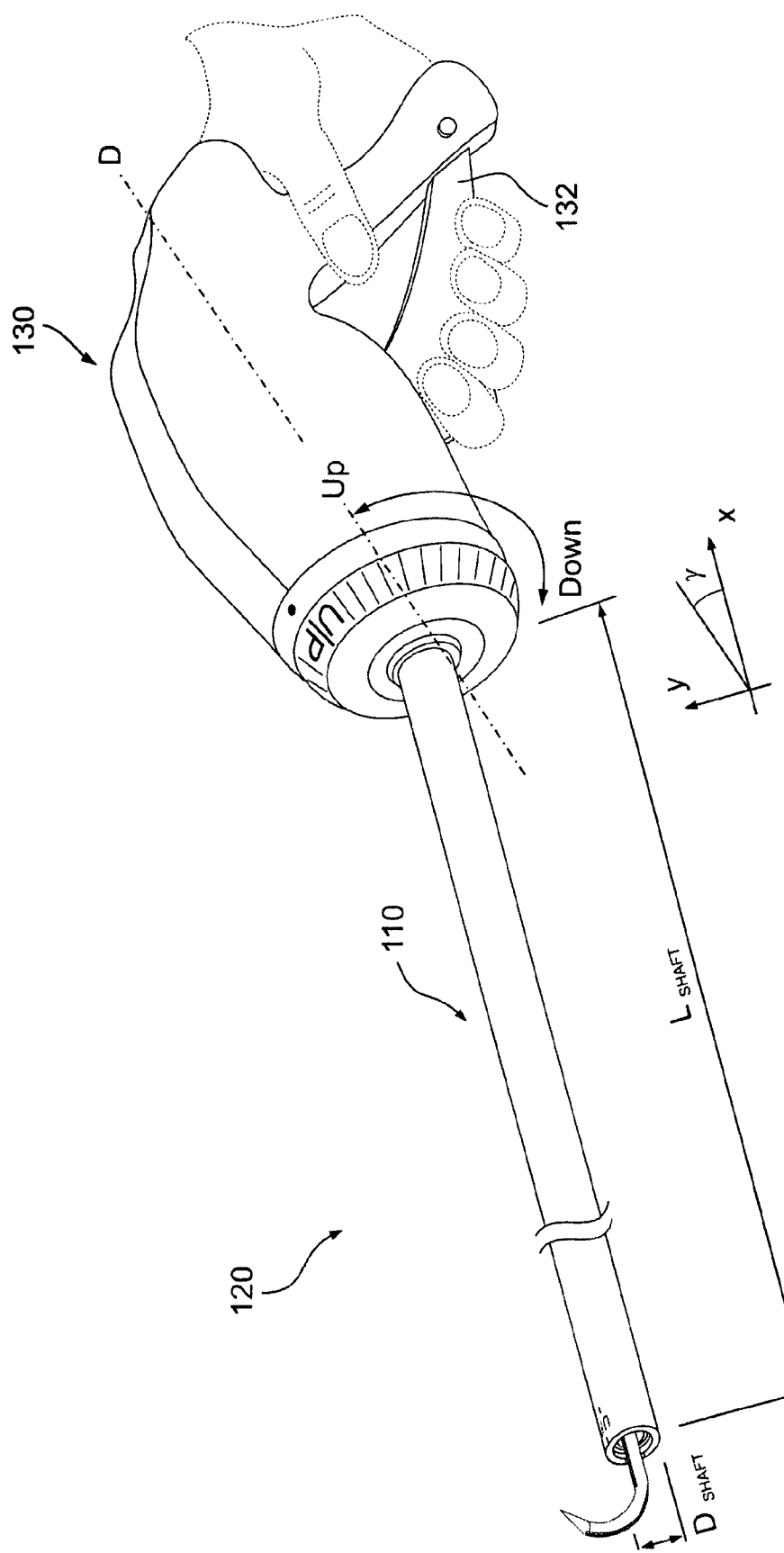
Figure 19C:
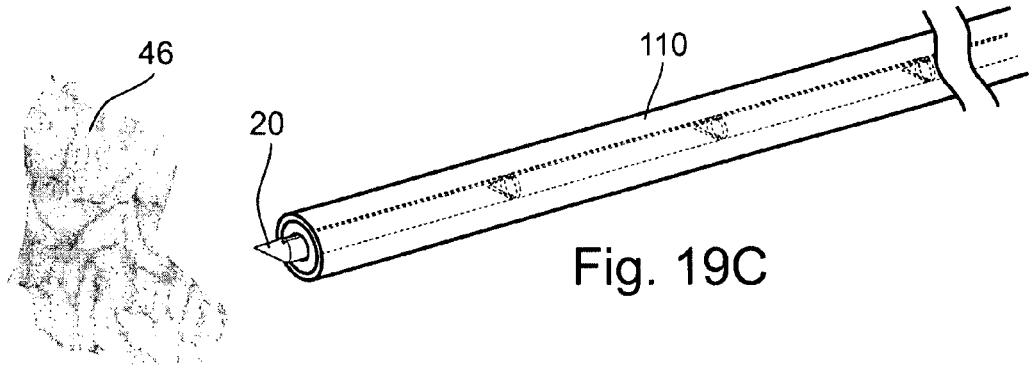
Figure 19D:
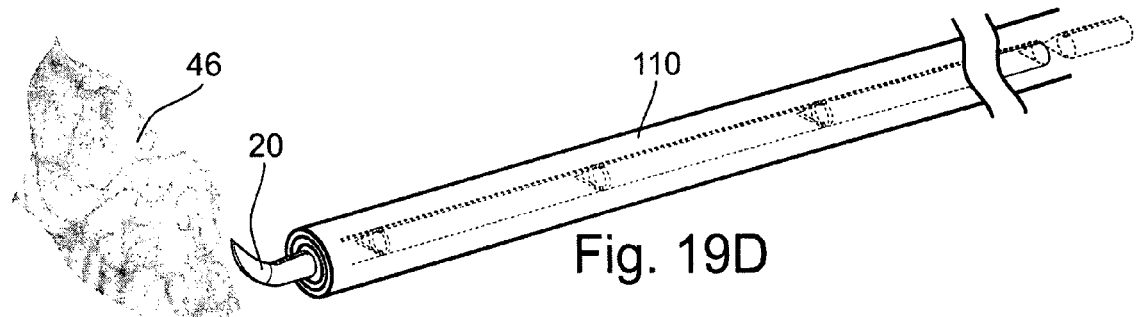

As seen in FIGS. 19A and 19B, while application shaft 110 is parallel to the x-axis, a length axis D of handle 130 is designed at an angle γ to the x-axis. Recalling from FIG. 1A that when the Auto-Staple device of the prior art is held at 90° to the fascia, as recommended, the surgeon's elbow makes an angle α of about 120° with the his arm. The hand is thus near the end of its rotational travel in that orientation, and its maneuverability is limited. The present design is intended to correct this.

In accordance with a preferred embodiment of the present invention, an angle γ is designed between length axis D and application shaft 110, so that when application shaft 110 is held at 90° to the surface of tissue 46, the surgeon's hand is outstretched, with substantially no bending at the elbow. This allows the surgeon maximum maneuverability, since the full range of elbow bending is available to him.

Preferably, angle γ is about 60°. Alternatively, another angle, for example, 300, 450, or 750 may be used. Additionally or alternatively, a ball-bearing arrangement may be provided, for allowing a variable angle setting, wherein the desired angle will be predetermined and set specifically for each operation.

It will be appreciated that SCS-IF™ device 120, for which length axis D and application shaft 110 are aligned is also within the scope of the present invention.

As seen in FIG. 19A, gripping handle 130 includes a gripping portion 129, and a spring-operated finger lever 132, connected to gripping portion 129 by a swivel pin 127. In this manner optimal ease of maneuverability for of finger-lever 132 is achieved. Preferably, finger lever 132 is adapted for operation by four fingers, thus being ergonomically designed. Alternatively, only the index finger, or only two or three fingers may be used.

Although only a schematic construction is provided in FIG. 19A, some features are worth noting. Finger lever 132 is in communication with a spring 134, and with a gear system 136, having gears 136A and 136B, arranged to rotate in opposite directions. Leaf springs 133, 137 and 139 ensure that gears 136A and 136B rotate in their desired directions.

The pressing of finger lever 132 causes gear 136B to rotate in the direction of an arrow 136C, so as to rotate gear 88 of second housing 80 (FIG. 18C), thus rotating internal thread 86, for issuing of stapling element 20.

Additionally, spring 134 provides for a controlled gradual motion of gear 136B and for a gradual insertion of stapling element 20. The gradual control may be stepwise, correlated with the gear teeth. It will be appreciated that the gradual insertion prevents tissue crushing, characteristic to the staple ejection of the prior-art device of FIG. 1A.

A return path is made possible by a button 131. On the return path, finger lever 132 communicates with gear 136A, which rotates in the direction of arrow 136D.

FIG. 19B schematically illustrates the exterior of handle 130 of SCS-IF™ device 120. As previously noted, application shaft 110 is preferably arranged on swivel dial 106, which provides a 360° rotation. The direction of closing of stapling element 20, which issues from SCS-IF™ device 120, corresponds to the indication "UP", and may be thus controlled by rotating dial 106.

It will be appreciated that a surgeon may apply a first stapling element 20, then rotate dial 106, and apply a second stapling element 20, closed in another direction.

In accordance with the present invention, SCS-IF™ device 120 may be adapted for Endoscopy, and may be referred to as SCS-IF-ENDO™ device 120. A length $L_{SHAFT}$ may be between about 37 and 40 cm, and a diameter $D_{SHAFT}$ may be between about 3 mm and 5 mm. Alternatively, the diameter $D_{SHAFT}$ may be up to about 12 mm. It will be appreciated that other dimensions, which may be larger or smaller, may similarly be used and are also within the scope of the present invention.

Alternatively, SCS-IF™ device 120 may be adapted for open surgery, and the length $L_{SHAFT}$ may be about 10-20 cm.

In accordance with an alternate embodiment of the present invention, a miniature motor may be provided, within handle 130, activated by finger lever 132, for providing the rotational motion of gear 88, in place of gear system 136. Preferably, finger lever 132 is further adapted to control the motor speed, thus the rate at which stapling elements 20 issue from application shaft 110.

FIGS. 19C-19F schematically illustrate stages of insertion of stapling elements 20, via application shaft 110, in accordance with an embodiment of the present invention.

As stapling element 20 issues from application shaft 110, it begins to close, and when completely out, it forms the closed loop of second shape 36 (FIG. 19F), enclosing on a tissue 46. A second stapling element 20 may then issue from application shaft 110.

It will be appreciated that for piercing tissue 46, a second tool (not shown) may be used, for pressing tissue 46 against stapling element 20, thus providing a counterforce to stapling element 20.

It will be appreciated that unlike the staple ejection of prior art (FIG. 1A), which may cause tissue crushing, stapling elements 20 issues gradually, and when the second tool is used for a counterforce, it provides a gentle counterforce, so as to cause minimal tissue crushing.

It will be further appreciated that unlike the figure-eight staples of the prior art, that press on the tissue (FIG. 1D), and may cause crushing, the loop formed by stapling element 20 causes little damage, other than the piercing action.

While FIGS. 19C-19F illustrate stapling element 20 of a circular cross section and rim 27, it will be appreciated that any other cross section and embodiment described hereinabove, or a combination thereof, may be used.

It will be appreciated that application shaft 110 (FIGS. 19C-19F) may be rotated as a whole, allowing the surgeon control over the direction of closing of stapling element 20. Thus, a surgeon may apply a first stapling element 20, then rotate the application shaft, and apply a second stapling element 20, closed in another direction.

Referring further to the drawings, FIGS. 20A-20C schematically illustrate example applications of stapling elements 20, by SCS-IF™ device 120 (FIGS. 19A-19F), in accordance with embodiments of the present invention. For simplicity, only application shaft 110 is shown.

FIG. 20A illustrates an abdominal hernia repair, by joining an artificial mesh 48, for example, of PPP, as known, and tissue 46, using stapling elements 20. The surgery may be an open surgery, or a minimally invasive surgery, such as laparoscopic repair.

It will be appreciated that patches, for example, of Dacron or PTFE, as known, may be used in a similar manner.

It is important that while the prior art uses staples at key points and sutures elsewhere, stapling elements 20 may be used for the entire mesh seam. For example, stapling elements 20 of about 22 mm may be used at key locations, to form heavy-duty staples 142, and stapling elements 20 of about 15 mm may be used elsewhere along the mesh seam, to form standard staples 144. Heavy-duty staples 142 may form elliptical closes, as compared to the circular closes of standard staples 144. It will be appreciated that other dimensions and cross sections may similarly be used.

FIG. 20B illustrates a stitching of a gastric tube 150, using stapling elements 20, to join two tissue edges, arranged end to end, and to form staples 152. As before, the surgery may be an open surgery, or a minimally invasive surgery.

FIG. 20C illustrates a Nissen Fundoplication, wherein a proximal stomach 160 is wrapped around the anastomosis, using stapling elements 20, to join two tissue edges, arranged end to end, and to form staples 162. Again, the surgery may be an open surgery, or a minimally invasive surgery.

Figure 21A:
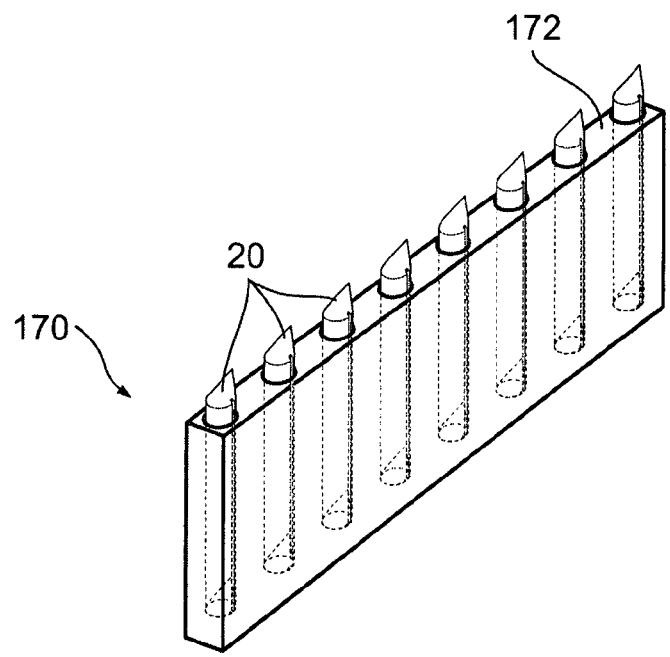
FIGS. 21A-21B schematically illustrate a cartridge, for a parallel application of a plurality of stapling elements, in accordance with an embodiment of the present invention.
Figure 21B:
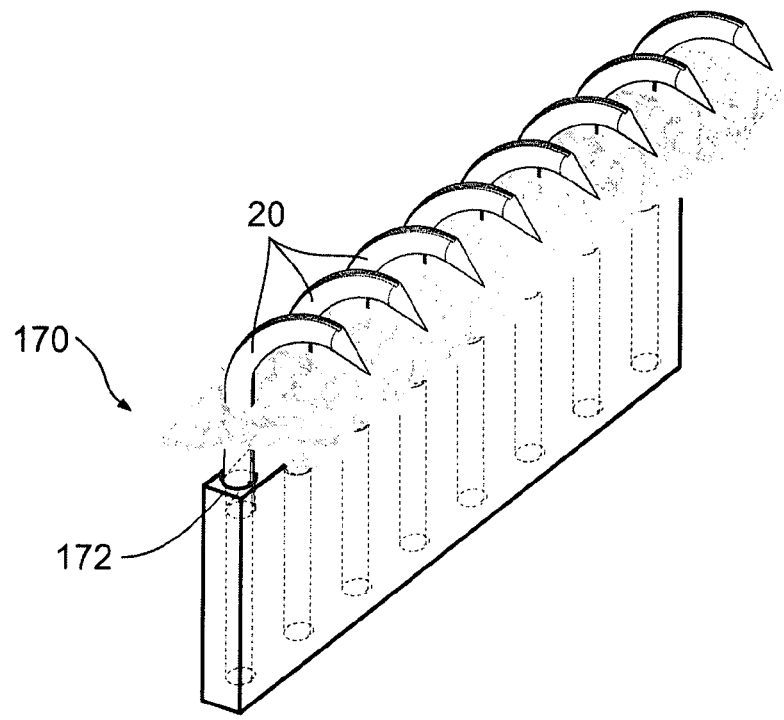

Referring further to the drawings, FIGS. 21A-21B schematically illustrate a cartridge 170, for a parallel application of a plurality of stapling elements 20, in accordance with an embodiment of the present invention. As seen in FIG. 21A, the plurality of stapling elements 20 are arranged parallel to each other, as a row, and may issue simultaneously. As seen in FIG. 21B, when issued, they are designed to close together, in a same direction. Cartridge 170 includes a rigid, proximal-end frame 172, at its proximal most end, with respect to the tissue. Rigid, proximal-end frame 172 defines the openings from which stapling elements 20 issue.

It will be appreciated that stapling elements 20 are placed within cartridge 170 at a fixed orientation, with respect to their direction of closing. Physical features prevent stapling elements 20 from rotating, in manners similar to those used in conjunction with first shaft 54, hereinabove (FIGS. 13A-13C, 14A-14C).

Referring further to the drawings, FIGS. 22A-22H schematically illustrate a Self-Coiling Staple-Transverse Anastomosis (SCS-TA™) device 180, for using stapling elements 20, in accordance with an embodiment of the present invention.

As seen in FIGS. 22G-22H, SCS-TA™ device 180 includes an gripping handle 179, a shaft 175, which may be straight, as in FIG. 22G, curved, as in FIG. 22H, or flexible, and an applicator 177, which houses cartridge 170, for a parallel application of a plurality of stapling elements 20. In general, SCS-TA™ device 180 is applicable to open surgery.

Figure 22A:
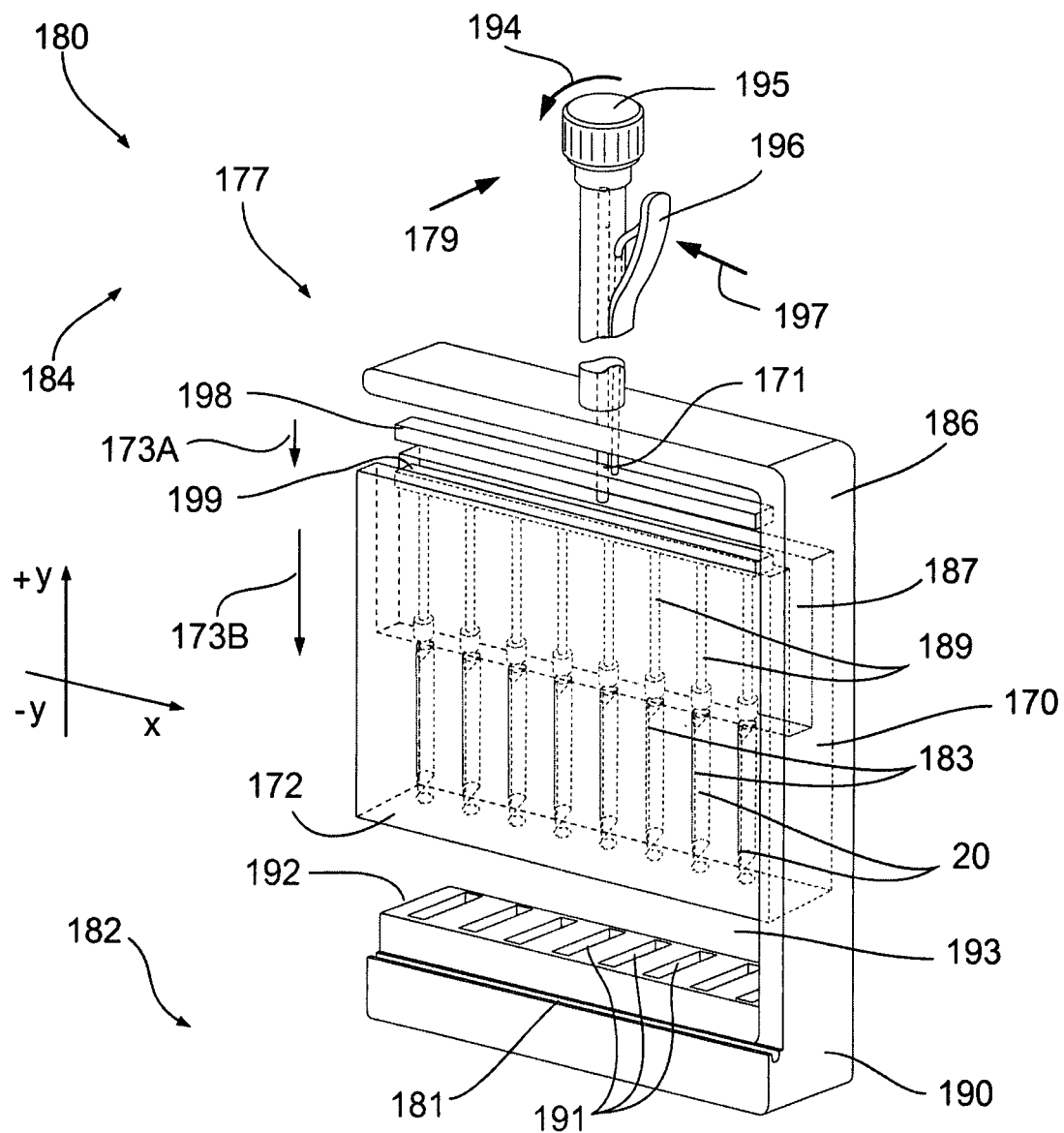

As seen in FIG. 22A, applicator 177 defines proximal and distal ends 182 and 184 with respect to the tissue, an x-axis, parallel to the line of the plurality of stapling elements 20, and a y-axis, parallel to the length axis of each stapling element 20.

Additionally, applicator 177 includes a housing 186, within which cartridge 170 is arranged, as seen in FIG. 21B. Cartridge 170 defines rigid, proximal-end frame 172, adapted to make contact with the tissue. In general, the tissue is to be placed between rigid, proximal-end frame 172 and a counter frame 192, within a space 193.

A proximal-most casing 190, defining an inner space within which stapling elements 20 may close, is provided. Proximal-most casing 190 includes counter to frame 192 which may further include rigid support slats 191. Preferably, casing 190 includes a knife track 181, for cutting excess tissue, as will be illustrated hereinbelow, in conjunction with FIGS. 23A-23D.

The operation of SCS-TA™ device 180 is controlled by gripping handle 179, as follows:

The turning of a knob 195, for example, in the direction of an arrow 194, causes a rod 171 to press down cartridge 170, bringing it to substantial contact with tissue 46 (not shown in these figures, but seen in FIGS. 23A-23D, hereinbelow), in space 193.

When substantial contact with tissue 46 is made, a lever 196 is pressed in the direction of an arrow 197, and rod 171 or another rod pushes a plate 198 in the −y direction, within a grove 187, as seen by an arrow 173A, pressing on a plate 199, which in turn pushes pistons 189 in the −y direction, in channels 183, as seen by an arrow 173B, so as to force stapling elements 20 out.

Figure 22C:
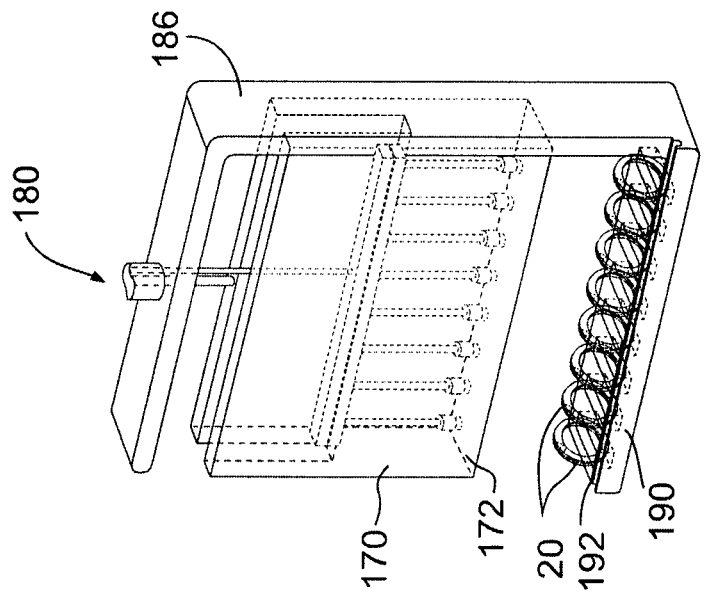
Figure 22B:
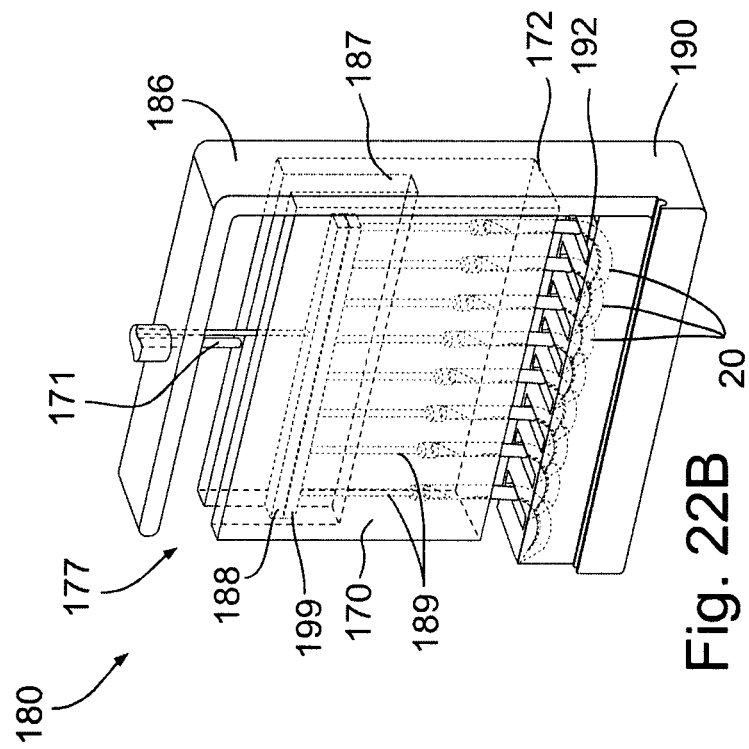

As seen in FIGS. 22B and 22C, closing takes place within casing 190.

Side views of applicator 177 are provided in FIGS. 22D-22F, illustrating the stages of ejection of stapling elements 20 by plates 198 and 199 and pistons 189. Knife tract 181 is designed for cutting the tissue after the stapling elements are inserted into the tissue.

SCS-TA™ device 180 is applicable to open surgery, for example, for gastric tube closures.

Referring further to the drawings, FIGS. 23A-23D schematically illustrate the joining of at least two layers of the tissue, 200 and 202, arranged back to back, by staples 204, to form a seam 205, for example, during an open surgery, for example, via SCS-TA™ device 180.

In some cases, it may be desired to cut off excess tissue, so that staple seam 205 is made into an edge seam 205. Preferably, a knife 207, that can be as well a part of the device, is used, as seen in FIGS. 23A-23D, for cutting along the seam of staples 204, along knife tract 181. Preferably, the cut exposes edges 206 of staples 204. By eliminating excess tissue beyond the seam, local necrosis, which may take place in the excess tissue, is prevented, and healing is promoted. It will be appreciated that the prior art has no staple, applicable as an edge seam (similar, for example, to the edge of a tablecloth or of a rug), whereas stapling elements 20 may be used for forming an edge seam.

Figure 23A:
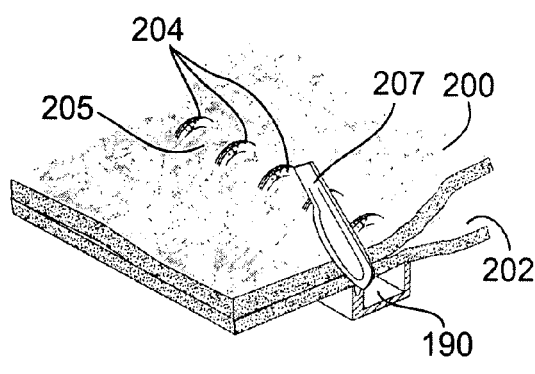
FIGS. 23A-23D schematically illustrate tissues, connected back to back, by a line of staples, to form an edge seam, during an open surgery, via an SCS-TA™ device of the present invention.
Figure 23B:
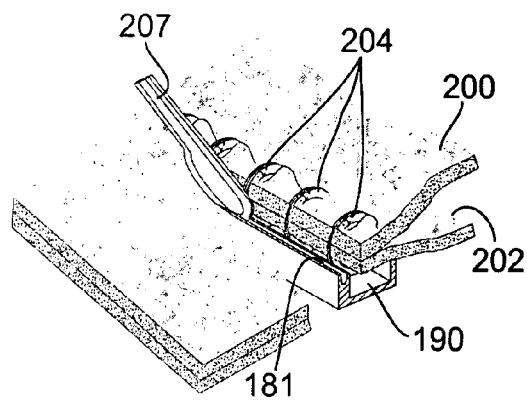
Figure 23C:
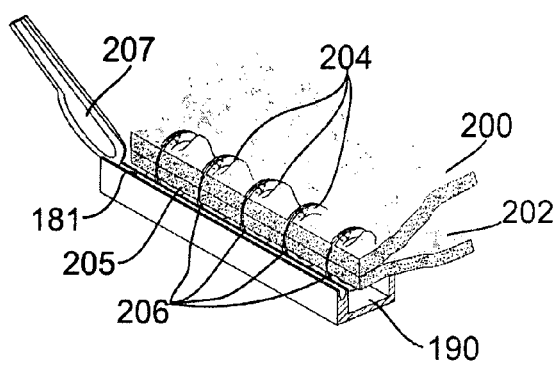
Figure 23D:
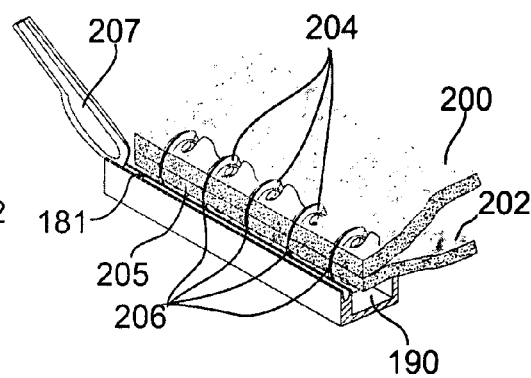

As seen in FIGS. 23A-23C, staples 204 are substantially closed. FIG. 23D illustrates another embodiment, wherein staples 204 are slightly open.

It will be appreciated that in some cases, the tissues may be left uncut.

It will be appreciated that SCS-TA™ device 180 may be used to apply more than one seam, for example, two or three seams, parallel to each other.

It will be further appreciated that in some cases, for example, in gastric fundus cases, two seams may be applied, parallel to each other, and the tissue, for example the stomach, may be cut between the parallel seams.

Figure 24A:
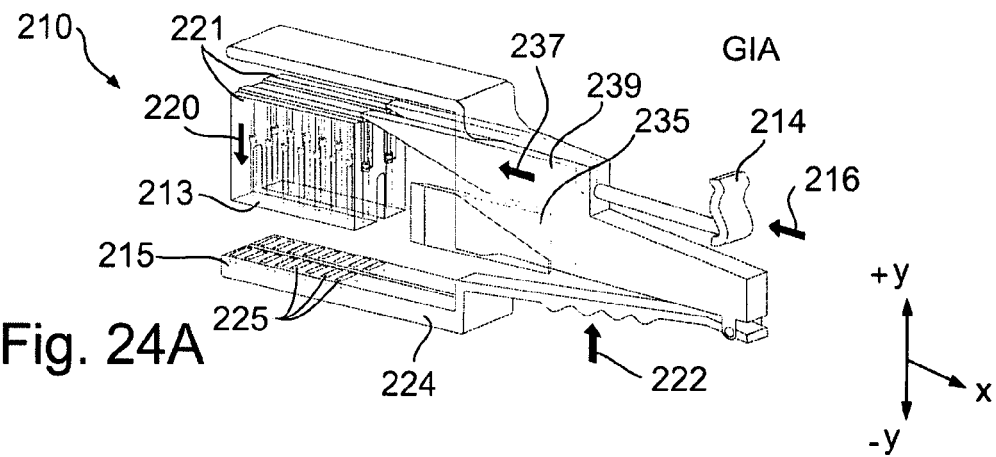
FIGS. 24A-24I schematically illustrate a Self-Coiling Staple-Gastro-Intestinal Anastomosis (SCS-GIA™) device, for using stapling elements, in accordance with an embodiment of the present invention.
Figure 24B:
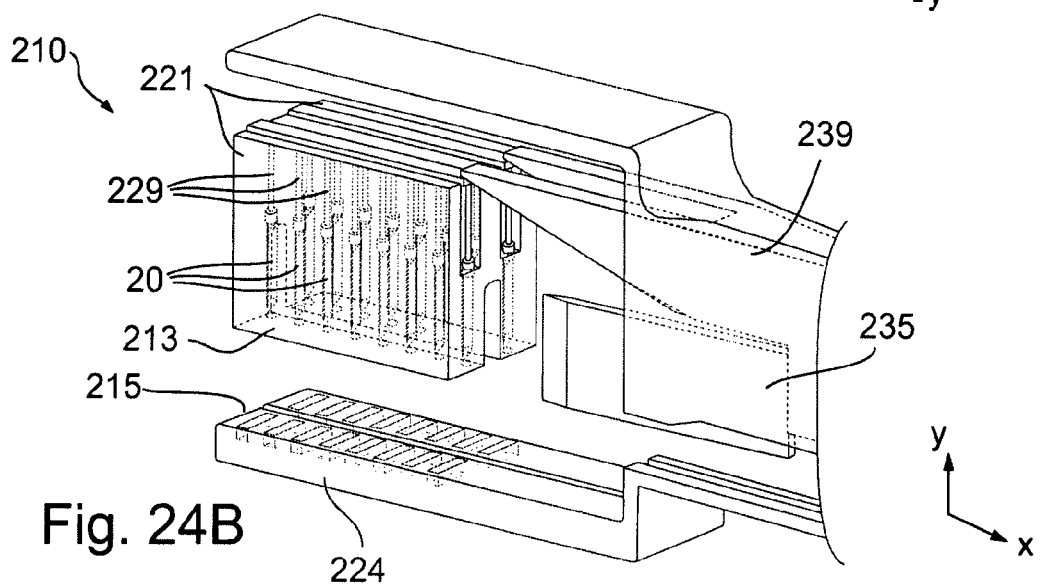
Figure 24C:
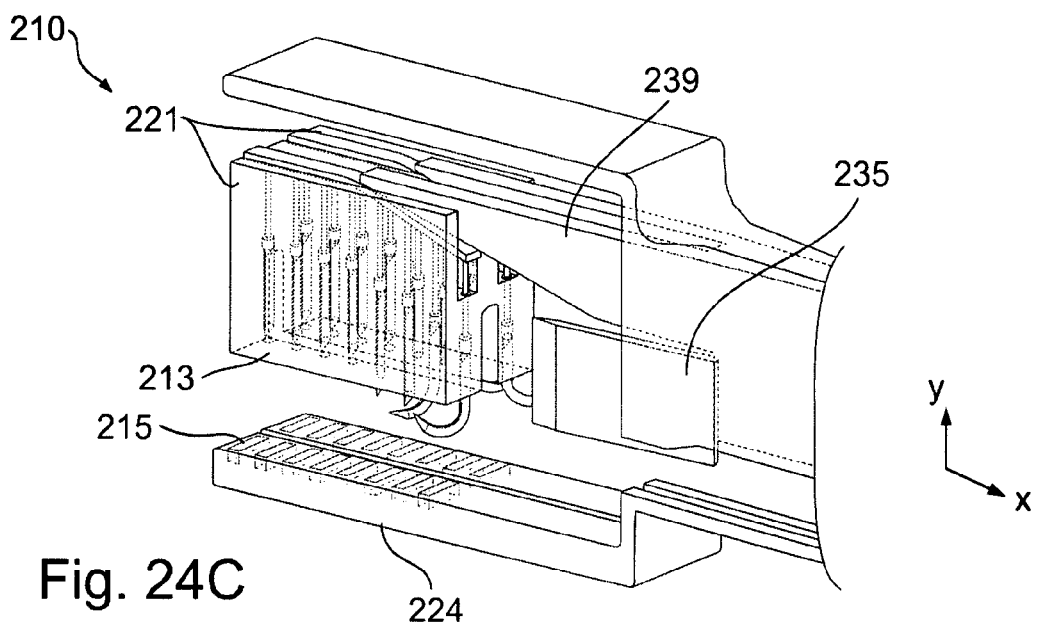

Referring further to the drawings, FIGS. 24A-24I schematically illustrate a Self-Coiling Staple-Gastro-Intestinal Anastomosis (SCS-GIA™) device 210, for using stapling elements 20, in accordance with an embodiment of the present invention. SCS-GIA™ device 210 contains two cartridges 221, for a two, parallel line application of stapling elements 20. Preferably, the two parallel lines, while applied in tandem, close at opposite directions, 180° apart (FIG. 24C).

Figure 24D:
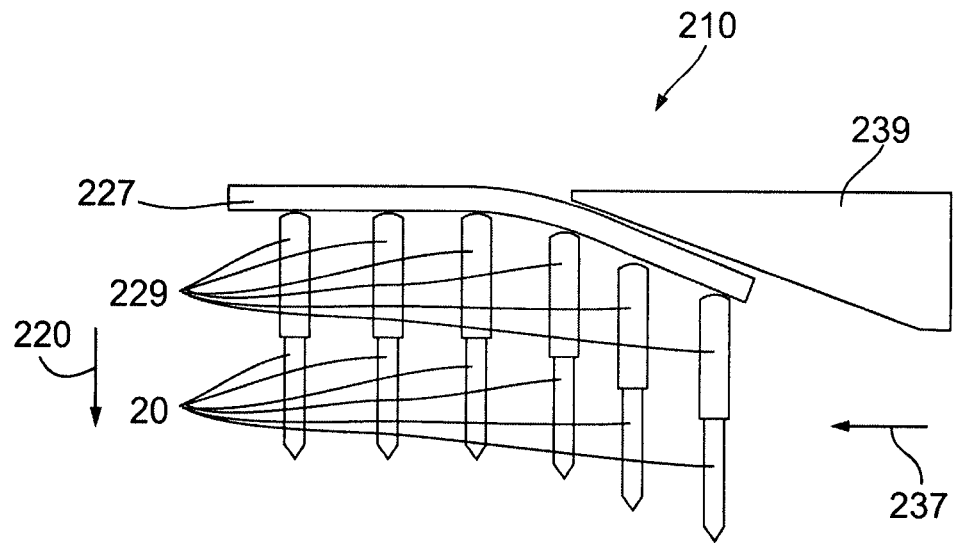
Figure 24E:
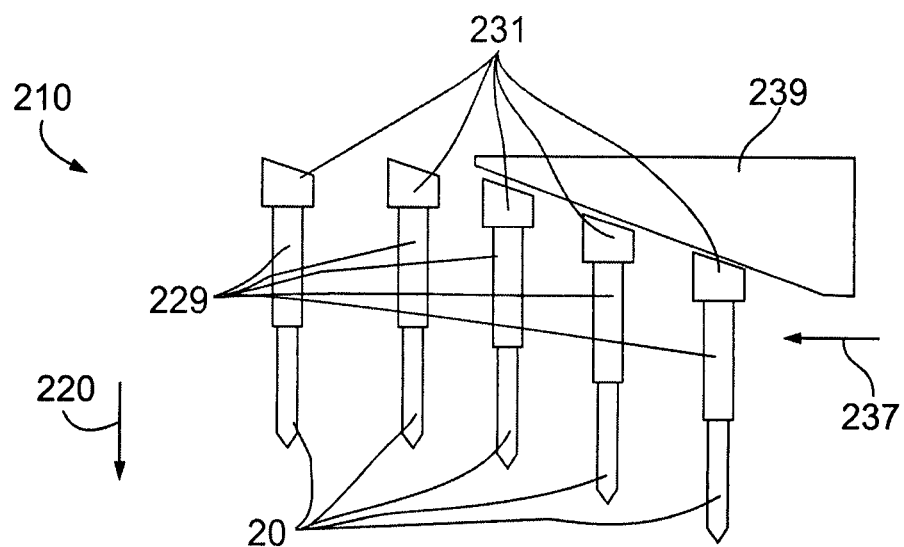
Figure 24F:
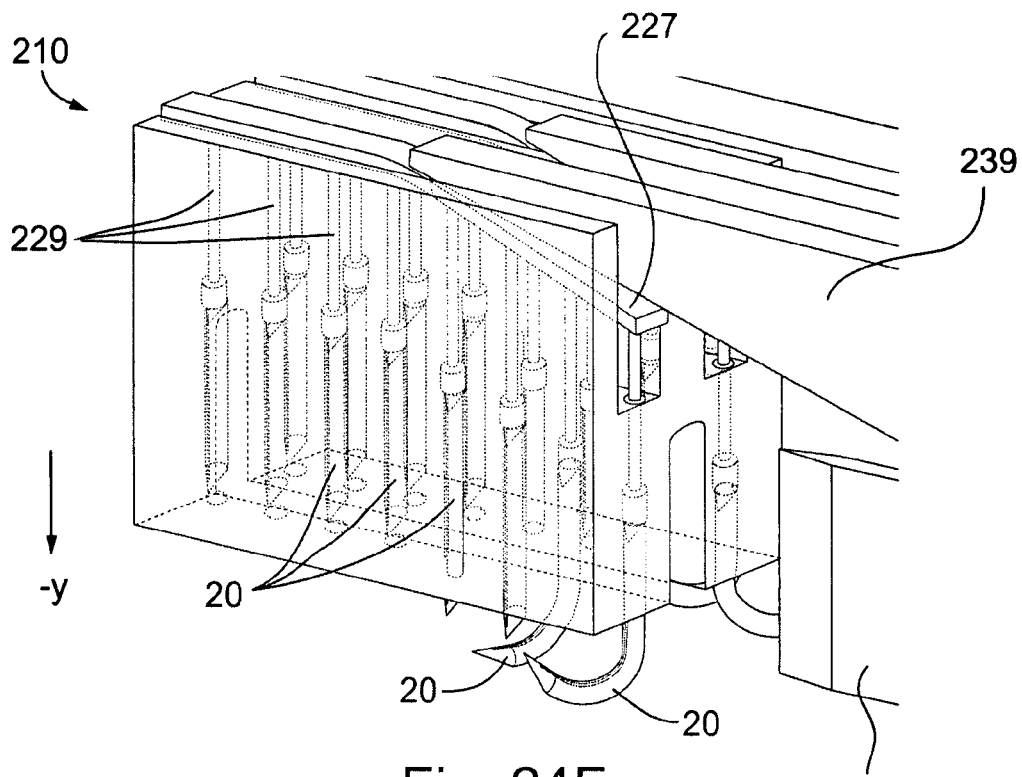
Figure 24G:
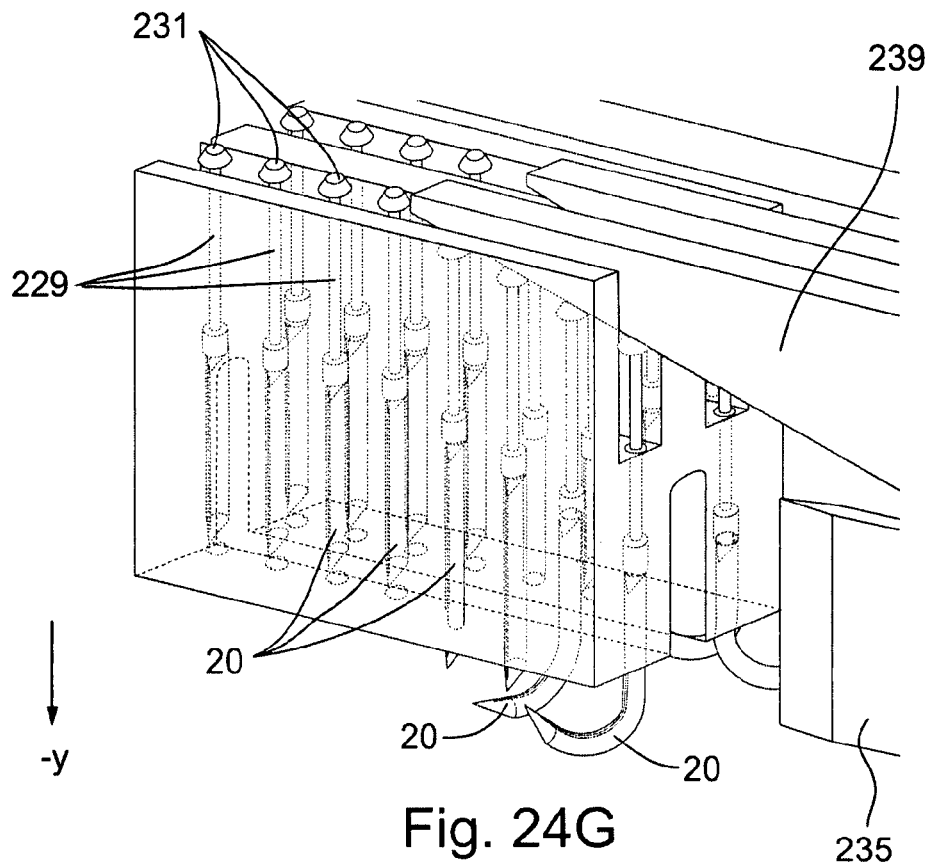
Figure 24H:
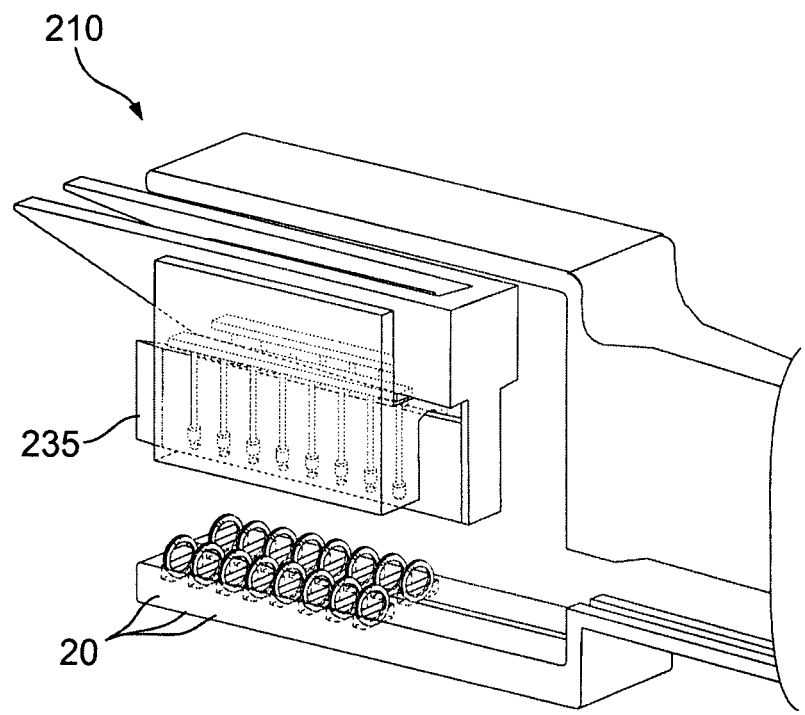
Figure 24I:
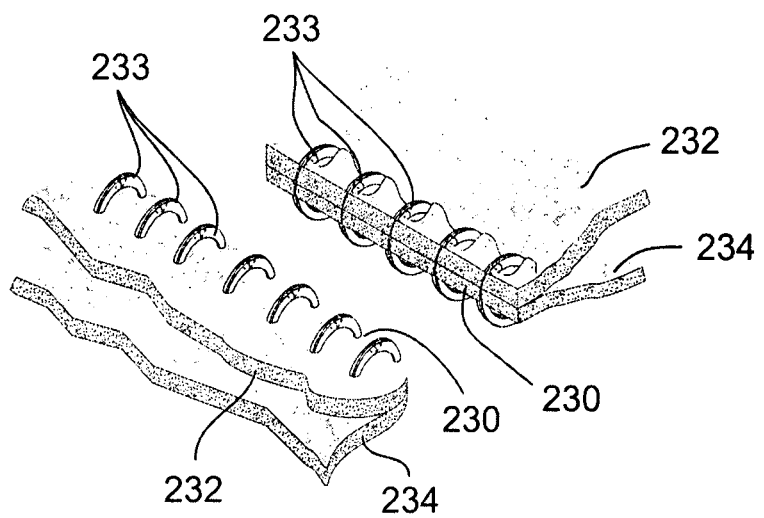

SCS-GIA™ device 210 is adapted for forming two edge seams, similar, for example, to the edges of a tablecloth or of a rug, as illustrated in FIG. 24I, wherein the two edge seams are arranged end to end. The edge seams promote heating and allow the flow of flood and nutrients to the tissue edge.

Cartridges 221 include a rigid, proximal-end frames 213. SCS-GIA™ device 210 further includes a counter frame 215 and a casing 224, defining a proximal inner space, which may be divided into compartments 225.

In accordance with the present embodiment, the tissue (not shown) is placed between rigid, proximal-end frames 213 and counter frame 215. Device 210 closes over the tissue by bringing counter frame 215 against proximal-end frame 213, in the direction of arrow 222. Preferably, closing takes place within casing 224, preferably, within compartments 225.

A lever 214 (FIG. 24A), adapted to move in the direction of an arrow 216, moves a triangular block 239, in the direction of an arrow 237, causing a plate 227 to force stapling elements 20, out, in the direction of arrow 220. Additionally, lever 214 moves a knife 235, along with triangular block 239, with a predetermined delay, so that when stapling elements 20 are inserted, knife 235 cuts the tissue between the two rows of staples that are formed (FIG. 24I).

As seen in FIGS. 24D and 24F, triangular block 239 presses on a flexible plate 227, in the y direction, which in turn applies pressure on pistons 229 and forces stapling elements 20 to issue.

Alternatively, as seen in FIGS. 24E and 24G, pistons 229 include hat-like portions 231, inclined at an angle that complements the angle of triangular block 239. Thus, triangular block 239 presses down on hat-like portions 231 of pistons 229, in the −y direction, which in turn applies pressure on pistons 229 and forces stapling elements 20 to issue.

As seen in FIGS. 24H and 24I, two seams 230 of staples 233 are formed on tissue 232 and 234. Knife 235 then slices the tissue between the parallel lines of seams 230. It will be appreciated that when desired, the tissue may remain uncut.

Referring further to the drawings, FIGS. 25A-25F schematically illustrate a Self-Coiling Staple-End to End Anastomosis (SCS-EEA™) device 240, for using stapling elements 20, in accordance with an embodiment of the present invention. SCS-EEA™ device 240 has an overall diameter of up to 35 mm, and may be used for endoscopy.

SCS-EEA™ device 240 is formed of two portions, a body 251 and an end-casing 259, which are connected via a central rod 269, of body 251. Central rod 269 has a sharp pointed edge and a screw thread 169, and is adapted to fit into screw hole 167 of end-casing 259. In general, body 251 is inserted from a first side of the tissue, and end-casing 259 is inserted from the other side. Central rod 269 is then fitted into screw hole 167, thus connecting the two portions.

SCS-EEA™ device 240 includes a release mechanism of a lever 245 and a knob 241. Additionally, SCS-EEA™ device 240 includes a round cartridge 244, wherein a plurality of stapling elements 20 are parallel to each other, in a circular arrangement. A round plate 273 and pistons 277 are adapted to push stapling elements 20 in the −y direction.

Round cartridge 244 includes a round frame 236, on its proximal side with respect to the tissue. Additionally, SCS-EEA™ device 240 includes a counter frame 238 and end-casing 259, defining an inner space, which may be divided to compartments 271.

Rotation of knob 241 in the direction of arrow 243 brings round frame 236 ageist counter frame 238, with the tissue between them.

Pressing lever 245 in the direction of an arrow 247 forces round plate 273 down in the −y direction, pushing pistons 277, in the −y direction, and forcing stapling elements 20 out.

Figures 25D, 25E:
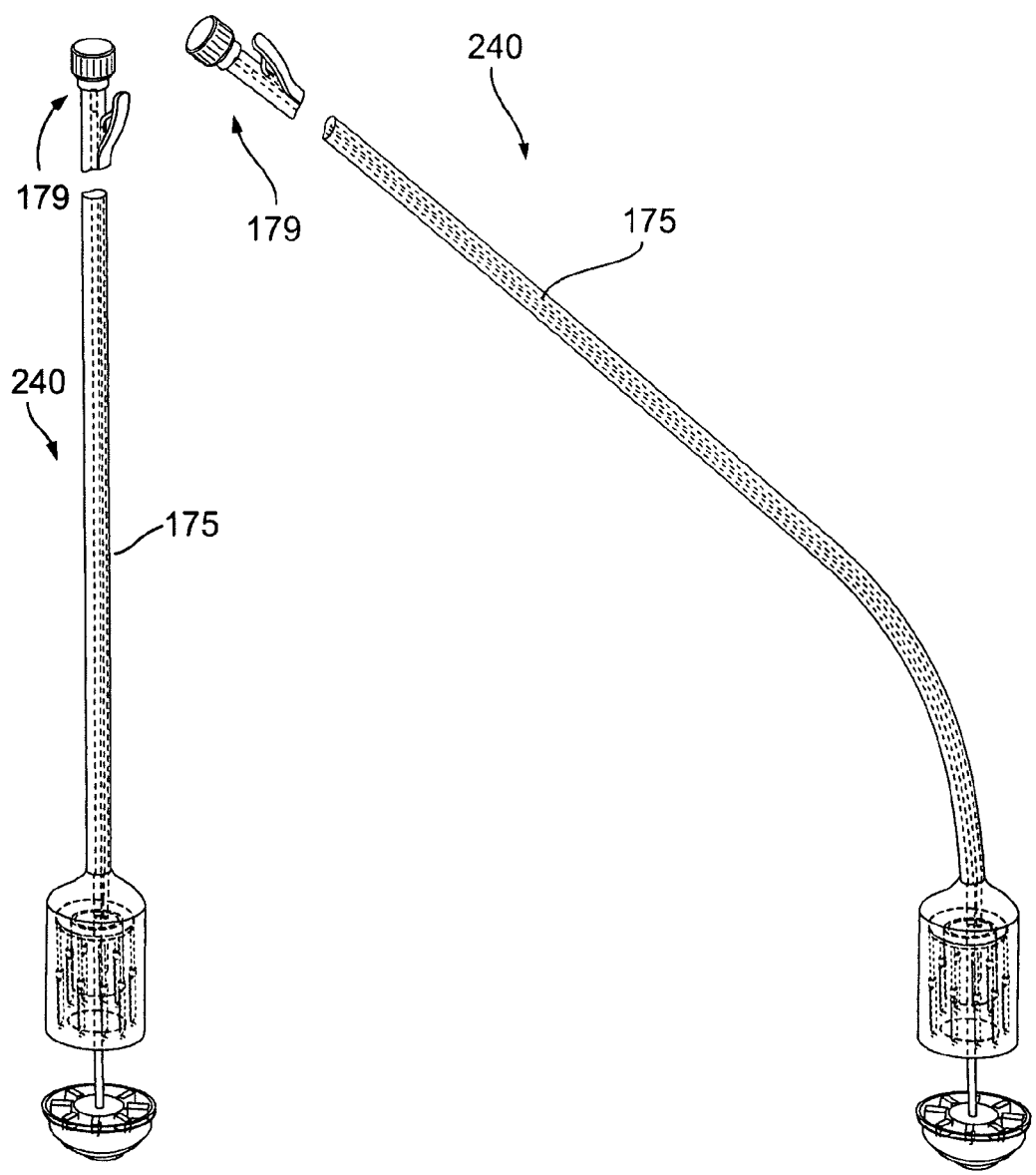
Figure 25F:
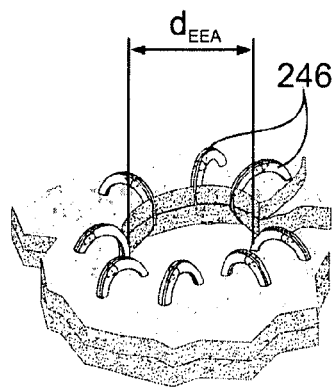

A circular knife 242 (FIG. 25C) may be used for cutting excess tissue within a circular seam 246 that is formed, when desired, as seen in FIG. 25D. Preferably, a diameter $d_{EEA}$ (FIG. 25F) of the cut is between about 18 and about 25 mm. It will be appreciated that other values are similarly possible.

As seen in FIGS. 25D and 25E, shaft 175 of SCS-EEA™ device 240 may be straight, curved, or flexible.

Figure 26:
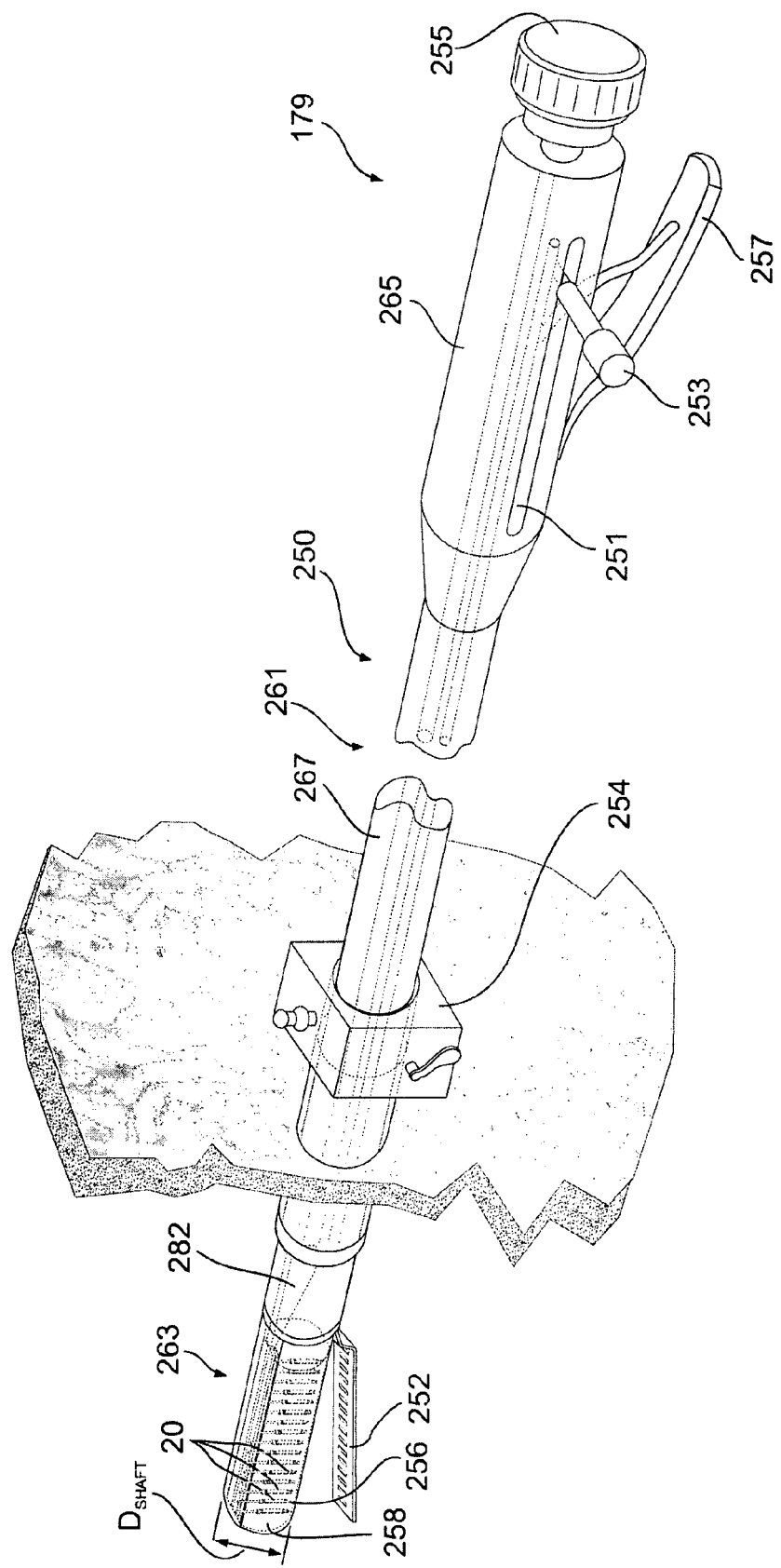
FIG. 26 schematically illustrates a Self-Closing Stapling-Transverse Anastomosis Endoscopy (SCS-TA-ENDO™) device, for using stapling elements, in accordance with an embodiment of the present invention.

Referring further to the drawings, FIG. 26 schematically illustrates a Self-Closing Stapling-Transverse Anastomosis Endoscopy (SCS-TA-ENDO™) device 250, for using stapling elements 20, in accordance with an embodiment of the present invention. SCS-TA-ENDO™ device 250 includes a gripping handle 265, and a shaft 267, preferably, with an overall diameter $D_{SHAFT}$ of between about 12 and about 35 mm, and may generally be 12 mm, or 16 mm or 35 mm, adapted for endoscopy. Shaft 267 has an extracorporeal portion 261 and an intracorporeal portion 263. A TRUCAR endoscopic valve 254 may be provided, between portions 263 and 261, for endoscopic insertion. It will be appreciated that other diameters may similarly be used.

At a proximal end with respect to the tissue, intracorporeal portion 263 includes a cartridge 258, having a single row of stapling elements 20 and a rigid, proximal-end frame 256, orthogonal to the row of stapling elements 20. Additionally, it includes a counter frame 252, parallel to rigid, proximal-end frame 256.

The operation of SCS-TA-ENDO™ device 250 is controlled by a knob 255 a lever 257, and a slide 253, arranged to slide within a channel 251. In essence, knob 255 determines the width of the gap, between proximal-end frame 256 and counter frame 252, and lever 257 brings counter frame 252 towards proximal-end frame 256. Slide 253 then pushes a triangular block 282 that forces stapling elements 20 to issue. Preferably, a knife 288 (FIG. 26), also in mechanical communication with slide 253, follows behind triangular block 283, for slicing the excess of tissue along the edge seam. It will be appreciated that knife 288 may be removed.

It will be appreciated that TRUCAR endoscopic valve 254 may similarly be provided for application shaft 110 of SCS-IF-ENDO™ device 120 (FIGS. 19A-19F), or SCS-EEA™ device 240, or for any other device of the present invention, adapted for endoscopic insertion.

Figure 27:
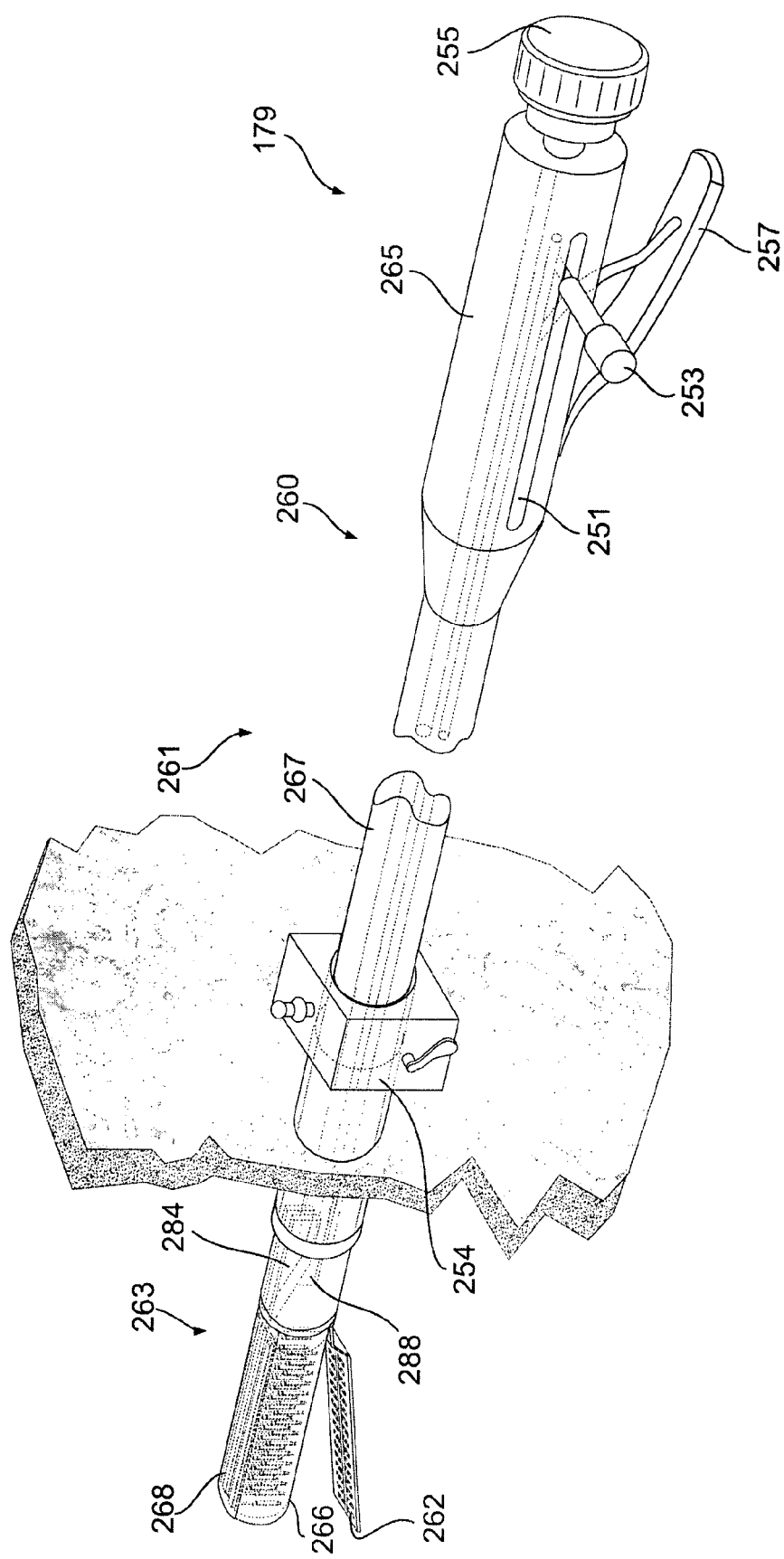
FIG. 27 schematically illustrates a Self-Coiling Staple-Endoscopic, Gastro-Intestinal Anastomosis (SCS-GIA-ENDO™) device, for using stapling elements, in accordance with an embodiment of the present invention.

Referring further to the drawings, FIG. 27 schematically illustrates a Self-Coiling Staple-Endoscopic, Gastro-Intestinal Anastomosis (SCS-GIA-ENDO™) device 260, for using stapling elements 20, in accordance with an embodiment of the present invention.

SCS-GIA-ENDO™ device 260 includes gripping handle 265, and shaft 267, having a shaft diameter preferably of about 12 mm, adapted for endoscopy. Shaft 267 includes extracorporeal portion 261, intracorporeal portion 263, and preferably also TRUCAR endoscopic valve 254 between portions 263 and 261, for endoscopic insertion. It will be appreciated that other shaft diameters may similarly be used.

At a proximal end with respect to the tissue, intracorporeal portion 263 includes a cartridge 268, having two parallel rows of stapling elements 20 and a rigid, proximal-end frame 266, orthogonal to the rows of stapling elements 20. Additionally, it includes a counter frame 262, parallel to rigid, proximal-end frame. The operation of SCS-GIA-ENDO™ device 260 is controlled by knob 255 lever 257, and slide 253.

The operation of SCS-GIA-ENDO™ device 260 is controlled by knob 255 lever 257, and slide 253, arranged to move within channel 251, as in the case of device 250 (FIG. 26). In essence, knob 255 determines the width of the gap, between proximal-end frame 266 and counter frame 262, and lever 257 brings counter frame 262 towards proximal-end frame 266. Slide 253 then pushes a triangular 284 block that forces stapling elements 20 to issue. Preferably, a knife 288, also in mechanical communication with slide 253, follows behind triangular 284, for slicing the tissue, along the edge seam. It will be appreciated that knife 288 may be removed.

Referring further to the drawings, FIGS. 28A-28J schematically illustrate a Self-Closing Stapling, Simultaneous-Firing (SCS-SF™) device 270, using stapling elements 20, in accordance with an embodiment of the present invention.

SCS-SF™ device 270 may be used for open surgery, and as such it may have a straight shaft, as illustrated in FIG. 28A, or a curved shaft, as in FIG. 28C. Additionally, it may be used for endoscopic surgery, operative as a Self-Closing Stapling, Simultaneous-Firing Endoscopy (SCS-SF-ENDO™) device, preferably, with a straight shaft, as illustrated in FIG. 28B.

For endoscopic surgery, SCS-SF™ device 270 includes a gripping handle 278 and a shaft 275, preferably, with an overall diameter of about 12 mm, adapted for endoscopy. Shaft 275 includes extracorporeal portion 261, intracorporeal portion 263, and preferably also TRUCAR endoscopic valve 254 between portions 263 and 261, for endoscopic insertion.

At a proximal end with respect to the tissue, intracorporeal portion 263 includes a cartridge 274, having a row of stapling elements 20 and a rigid, proximal-end frame 276, orthogonal to the row of stapling elements 20. However, a counter frame is not provided. Rather, in some cases, a second tool (not shown) may be used to gently provide a counter force to stapling elements 20.

The operation of SCS-SF™ device 270 is controlled by a spring-operated lever 272, for issuing the row of stapling element 20 simultaneously.

Preferably, lever 272 provides gradual control over the extent of issuing of stapling elements 20.

Figure 28D:
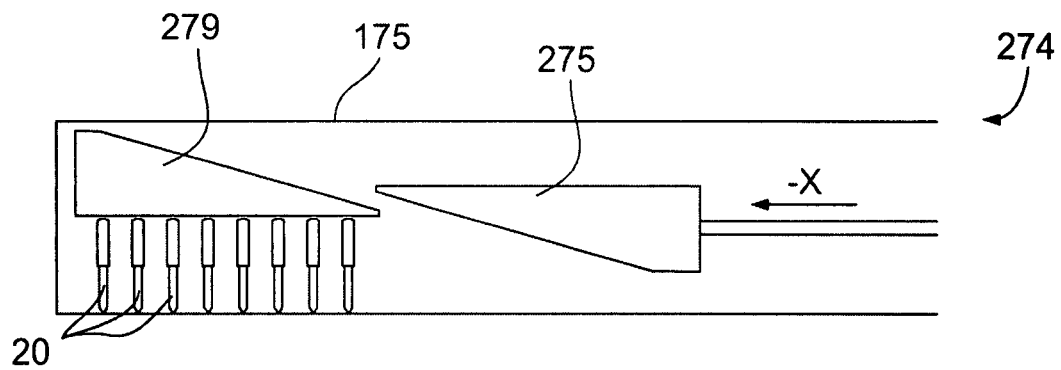
Figure 28E:
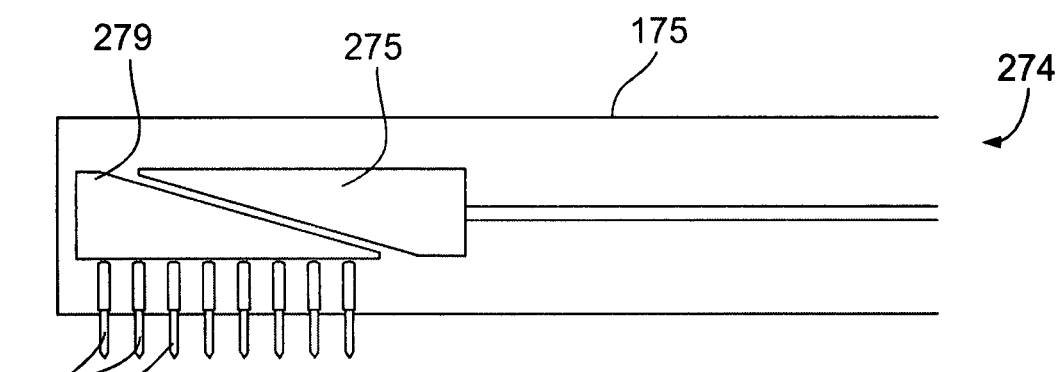

As seen FIGS. 28D-28E, spring-operated lever 272 (FIG. 28A) pushes a triangular block 275 in a −x direction, forcing a second, complimentary block 279 to push stapling elements 20 out.

Figure 28F:
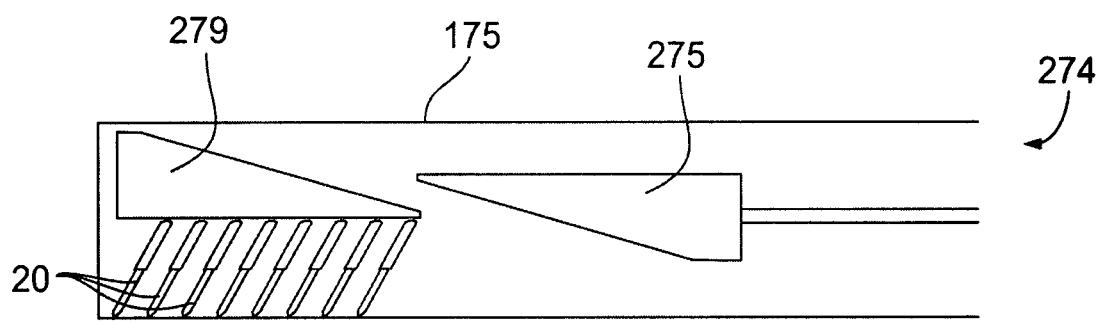

As seen in FIG. 28F, stapling elements may be arranged at an angle to shaft 175, when longer stapling elements are desired.

FIGS. 28I and 28J illustrate a handle with a gradual controlled release mechanism of the staples, as follows:

FIG. 28I illustrates SCS-SF™ device 270, with handle 130, similar to that of FIGS. 19A-19B, but aligned with the application shaft.

FIG. 28J illustrates SCS-SF™ device 270, with handle 130, similar to that of FIGS. 19A-19B, at an angle γ to the application shaft.

As seen in FIGS. 28G and 28H, SCS-SF™ device 270 may be used in a manner similar to SCS-IF™ device 120 of FIGS. 20B and 20C, hereinbelow, while speeding up the operation (over device 120), by applying several staples simultaneously.

FIG. 28G illustrates the stitching of gastric tube 150, using SCS-SF™ device 270 and stapling elements 20, for forming staples 152. The surgery may be an open surgery, or a minimally invasive surgery.

FIG. 28H illustrates the Nissen Fundoplication, wherein proximal stomach 160 is wrapped around the anastomosis, using SCS-SF™ device 270 and stapling elements 20, for forming staples 162. Again, the surgery may be an open surgery, or a minimally invasive surgery.

Figure 29:
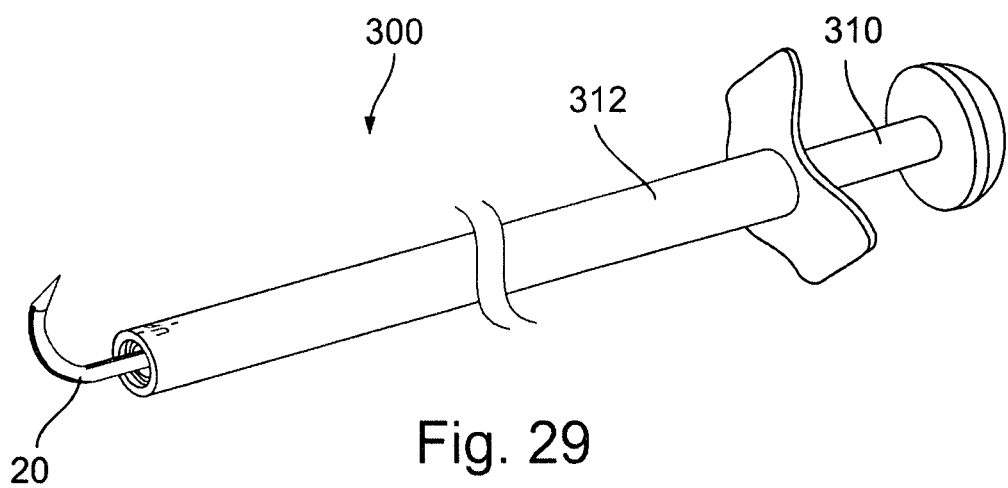
FIG. 29 schematically illustrates a Self-Closing Stapling, Single-Shot (SCS-SS™) device, in accordance with an embodiment of the present invention.

Referring further to the drawings, FIG. 29 schematically illustrates a Self-Closing Stapling, Single-Shot (SCS-SS™) device 300, arranged as a syringe 312, having a piston 310, adapted to apply a single stapling element 20, in accordance with an embodiment of the present invention. Preferably, device 300 is for a single use.

It will be appreciated that device 300 may also be a Self-Closing Stapling, Single-Shot Endoscopy (SCS-SS-ENDO™) device.

Referring further to the drawings, FIGS. 30A-30D schematically illustrate a stapling element, formed as a composite of at least two materials, in accordance with another embodiment of the present invention.

FIGS. 30A-30B, show side and cross-sectional views of a stapling element 410, formed as a composite of materials 412 and 414, bonded side by side. Stapling element 410 is shown in first shape 34, adapted for insertion, and further includes a tapered portion 416 for piercing the tissue. It will be appreciated that stapling element 410 also includes second shape 36 (FIG. 2E), essentially as a closed loop.

FIGS. 30C-30D, show side and cross-sectional views of a stapling element 420, formed as a composite of materials 412 and 414, bonded as a core section formed of material 412, and a cladding section formed of material 414. Stapling element 420 further includes a tapered portion 418 for piercing the tissue. Although shown in first shape 34, it will be appreciated that stapling element 420 also includes second shape 36 (FIG. 2E), essentially as a closed loop.

It will be appreciated that other arrangements of the two materials, 412 and 414, along the length of the stapling elements may be used.

While one of materials 412 and 414 may be a shape memory alloy, having a memorized shape, as a loop, for closing around the tissue, the other may be a metal or a polymer, to provide added strength to the composite, for greater penetration power. The optimal ratio of materials 412 and 414 in the composite is preferably such as to ensure optimal penetration power and optimal memory.

Preferably, stapling elements 410 and 420 include physical features that prevent their rotation within an application shaft.

Preferably, stapling elements 410 and 420 include a cavity at their distal end, to accommodate the tapered portion.

Referring further to the drawings, FIGS. 31A-31C schematically illustrate an application shaft 400 for inserting staples while in a coiled shape, in accordance with still another embodiment of the present invention. A mechanism for insertion may engage, for example, with a feature, such as rim 27, for forcing stapling elements 20 to issue. Alternatively, it may engage with distal portion 24. In accordance with the present embodiment, stapling element 20 is formed of a resilient material, such as alloys, pure metals, polymers and (or) composites, but does not include a clearly defined first shape 34 (FIG. 2A).

Additionally, application shaft 400 may be adapted for inserting one stapling element 20 or a plurality.

For inserting a plurality of stapling elements 20 in series, they may be stored in the application shaft in a snail-like, spiraling tunnel. Alternatively, For inserting a plurality of stapling elements 20 in parallel, they may be stored in the application shaft in individual circular tunnels.

Figure 19E:
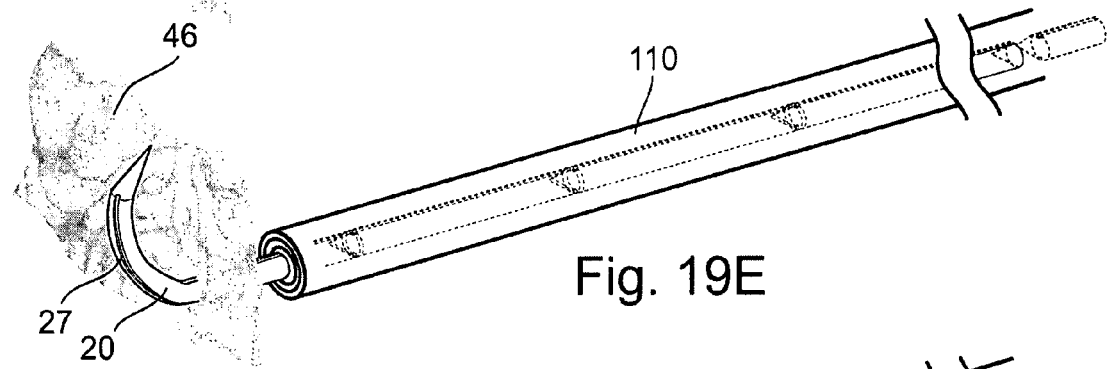
Figure 19F:
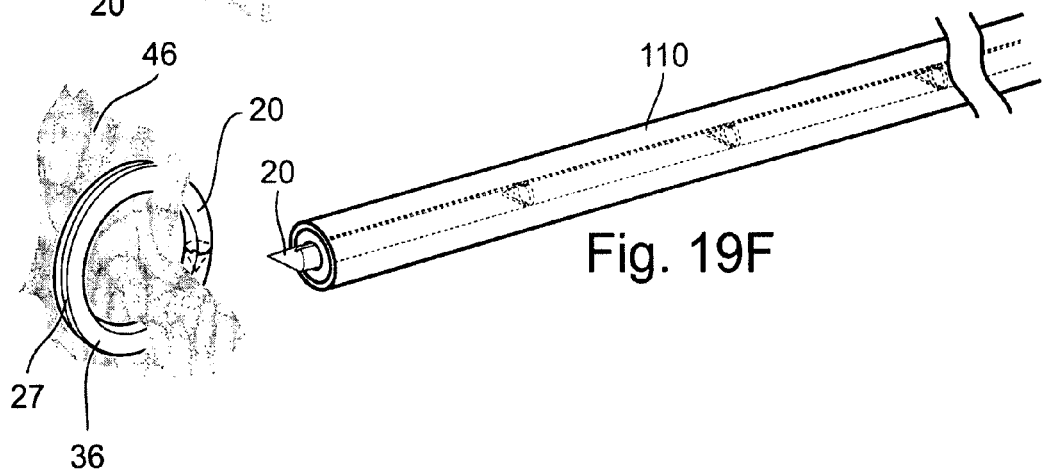

Important advantages of the present invention, when compared to the prior art, for example, as illustrated in FIGS. 1A-1F, are worth noting:

As seen in FIG. 1A of the prior art, maintaining fascia edges 14 and 16 taut and abut against each other requires three tools, such as tools 18A, 18B and 18C of FIG. 1A. However, in accordance with the present invention, the surgeon may catch the first fascia edge, by stapling element 20, operative as a needle, as seen in FIG. 19E and bring it to the second fascia edge, as seen in FIG. 20B. Thus stapling element 20 is operative also as a tool, and the overall number of tools that are needed is reduced.

As seen in FIG. 1A of the prior art, the staple ejection of Auto Staple device 10 may crush tissue, and possibly lead to local necrosis. However, in accordance with the present invention, for example, as taught in conjunction with FIGS. 19A-19F, 28A-28J, and 29, hereinabove, stapling elements 20 issues gradually, possibly against a second tool that provides a gentle counter force, so as to cause little tissue crushing and minimize local necrosis.

As seen in FIG. 1D of the prior art, the figure eight that is formed by staples 12 may further crush the tissue, and may interfere with blood and nutrient flow, possibly leading to local necrosis. However, in accordance with the present invention, for example, as taught in conjunction with FIG. 19F, hereinabove, stapling element 20 closes due to its self-coiling property, to form a loop that does not press on the tissue, to further minimize local necrosis.

The prior art has no staple, which is applicable as an edge seam (similar, for example, to an edge seam of a tablecloth or of a rug.) However, in accordance with the present invention, for example, as taught in conjunction with FIGS. 23A-23D, 24I and 25F, hereinabove, stapling elements 20 may be used for forming an edge seam. By eliminating excess tissue beyond the seam, local necrosis, which may take place in the excess tissue, is prevented, and healing is promoted.

Further with regard to the edge seam of FIGS. 23A-23D, 24I and 25F, stapling element 20 of the present invention is applied perpendicular to the tissue edge, enabling blood and nutrients to pass between staples to the tissue edge, in a manner similar to a suture applied manually, as illustrated in FIG. 1F, to prevent local necrosis.

As seen in FIG. 1A of the prior art, when the Auto-Staple device is held at 90° to the fascia, as recommended, the surgeon's elbow makes an angle α of about 120° with the his arm; the hand is thus near the end of its rotational travel in that orientation, and its maneuverability is limited. However, in accordance with the present invention, for example, as taught in conjunction with FIGS. 19A-19B, hereinabove, an angle γ is designed between length axis D of handle 130 and application shaft 110, so that when application shaft 110 is held at 90° to the tissue, the surgeon's hand is outstretched, with substantially no bending at the elbow. This allows the surgeon maximum maneuverability, since the full range of elbow bending is available to him.

When joining an artificial mesh and a tissue, the prior art generally uses staples at key points such as at the corners and midpoints of the mesh seam, and staples elsewhere along the mesh seam. However, in accordance with the present invention, for example, as taught in conjunction with FIG. 20A, hereinabove, stapling elements 20 may be used for the entire mesh seam. For example, stapling elements 20 of about 22 mm may be used at key locations, to form heavy-duty staples 142, and stapling elements 20 of about 15 mm may be used elsewhere along the mesh seam, to form standard staples 144. Heavy-duty staples 142 may form elliptical closes, as compared to the circular closes of standard staples 144. It will be appreciated that other dimensions and cross sections may similarly be used.

The prior art has no devices operable as SCS-IF™, SCS-IF-ENDO™, SCS-SF™, SCS-SF-ENDO™, SCS-SS™, SCS-SS-ENDO™, SCS-TA-ENDO™, and SCS-GIA-ENDO™. However, in accordance with the present invention, for example, as taught in conjunction with FIGS. 19A-19B, 26-29, and 28A-28J, hereinabove, such devices are provided.

It will be appreciated that any stapling element 20, described in conjunction with FIGS. 2A-11G and 30A-30B, hereinbelow, may be used with any of the application shafts, cartridges, and devices, described in conjunction with FIGS. 12A-31C, hereinbelow.

It will be appreciated that any seam of stapling element 20, described in conjunction with FIGS. 2A-11G hereinbelow, and (or) any seam provided by any of the application shafts, devices, and cartridges, described in conjunction with FIGS. 12A-31C hereinbelow, may be made into an edge seam, by cutting the excess tissue with a knife.

It will be appreciated that TRUCAR endoscopic valve 254 may be provided for any of the devices, adapted for endoscopy. Additionally, entry diameters smaller or greater than 12 mm may be provided with valve 254.

It will be appreciated that the devices described herein may be disposable. Alternatively, the cartridge containing stapling elements 20 may be disposable, but the device may be placed in an autoclave and reused. It will be appreciated that during an operation, cartridges may be replaced in a device in use—an empty cartridge may be removed, and a new one inserted.

It will be appreciated that for each device, different cartridges may be provided, for different applications. The different cartridges may be of different stapling-element materials, cross-sections, lengths, and number. For example, for a given device, there may be cartridges, with stapling elements of a circular cross section, for minimal trauma, or of an elliptical cross section, for maximum strength, or of a triangular cross section, for penetrating hard tissue. Additionally, there may be cartridges, with stapling elements formed of an alloy, for a relatively greater flexibility, or of a composite, for a relatively greater strength. Additionally, other cross sections may be used. Furthermore, for a given device, there may be cartridges of different stapling-element lengths, for example, 4 mm, 7 mm, 9 mm, 15 mm, or of another length, which may be larger or smaller, and may even be as large as 200 mm. Moreover, for a given device, there may be cartridges, with different numbers of stapling elements in each, for example, 10, 15, 30 or another number of stapling elements per cartridge.

Thus, it will be appreciated that the device may be fitted with a cartridge in the factory, or on the site, at the operation room.

It will be appreciated that for invasive surgery, the length of the stapling element may depend on the device. For example, when using device 120 of FIGS. 19A and 19B, device 240 of FIGS. 25A-25E, or device 300 of FIG. 29, hereinabove, the length of stapling element 20 is not limited by the device, and lengths as large as for example, 15 mm, 20 mm, 45 mm or larger may be used. However, when using devices 250 or 260 of FIG. 26 or 27, the size $D_{SHAFT}$ (FIG. 26) is limiting, and is limited by TRUCAR endoscopic valve 254, for example, to about 12 mm, and the maximum lengths of stapling elements 20 may be about 6 mm. Somewhat larger stapling elements 20 may be used in conjunction with device 20 of FIGS. 28A-28J, since stapling elements 20 may be arranged at an angle to the tissue, as seen in FIG. 28F.

It will be appreciated that generally, for blood vessels, stapling elements of 4 mm are used, and they are color coded white. For the gastrointestinal tract, stapling elements of 5 mm are used, and they are color coded blue. For the stomach, stapling elements of 6 mm are used, and they are color coded green. It will be appreciated that the stapling elements of the present invention may follow the color code that is used in the art. Additionally, stapling elements of other sizes may be used, and may be color coded by other colors.

It will be appreciated that various alternative mechanical means are known for producing the motions described in conjunction with the devices of FIGS. 19A-29. The mechanical means described hereinabove, in conjunction with these figures were for the purpose of illustrations. In accordance with the present invention, other mechanical means, as known, which may be manual or motorized, may similarly be used.

It will be further appreciated that any combination of the embodiments of FIGS. 2A-29, hereinabove is within the scope of the present invention.

A summary of the devices in accordance with the present invention is as follows:
i. Self-Closing Stapling, Intermittent Firing (SCS-IF™) device 120;
ii. Self-Closing Stapling, Intermittent Firing Endoscopy (SCS-IF-ENDO™) device 120;
iii. Self-Closing Stapling, Simultaneous Firing (SCS-SF™) device 270;
iv. Self-Closing Stapling, Simultaneous Firing Endoscopy (SCS-SF-ENDO™) device 270;
iii. Self-Closing Stapling, Single Shot (SCS-SS™) device 300;
iv. Self-Closing Stapling, Single Shot Endoscopy (SCS-SS-ENDO™) device 300;
v. Self-Closing Stapling-Transverse Anastomosis (SCS-TA™) device 180;
vi. Self-Closing Stapling-Transverse Anastomosis Endoscopy (SCS-TA-ENDO™) device 250;
vii. Self-Closing Stapling-Gastro-Intestinal Anastomosis (SCS-GIA™) device 210;
viii. Self-Closing Stapling-Gastro-Intestinal Anastomosis Endoscopy (SCS-GIA-ENDO™) device 260; and
ix. Self-Closing Stapling-End-to-End Anastomosis (SCS-EEA™) device 240.

It will be appreciated that while these device have predetermined gripping positions, they may be adapted for changing the predetermined closing direction of stapling element 20 without changing the gripping position. For example, shaft 175 (FIGS. 22H, 22G), attached to gripping handle 179, or shaft 267 (FIGS. 26 and 27) attached to gripping handle 265, or shaft 275 (FIGS. 28A-28C) attached to gripping handle 278 may be attached to their respective gripping handles with dial 106 (FIGS. 18D and 19A), for changing the predetermined closing direction of stapling element 20 without changing the gripping position on the respective gripping handle.

It will be appreciated that shaft 175 (FIGS. 22H, 22G), shaft 267 (FIGS. 26 and 27) and shaft 275 (FIGS. 28A-28C) may be flexible.

It will be appreciated that the devices described herein for minimally invasive procedures, such as endoscopic surgery or laparoscopic repair may also be used via body lumens, by insertion via the rectum, the vagina, the urinary tract, the respiratory tract, or any other body lumen.

It will be appreciated that the staples may be formed of a shape memory alloy. Alternatively, they may be formed of a resilient material, which may be a pure metal, an alloy, or a polymer. Alternatively, they may be formed as a composite of two or more materials. It will be further appreciated that when formed of a resilient material, the staples may be loaded into the application shaft in the operation room, shortly before insertion.

Alternatively, the stapling elements may be formed of a composite of two materials.

It is expected that during the life of this patent many relevant devices and methods for stapling elements and their application will be developed and the scope of the terms stapling elements and staple devices are intended to include all such new technologies a priori.

As used herein the term "about" refers to +30%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for applying staples to a tissue, comprising:
at least one stapling element for piercing through a tissue and forming a closed loop through said tissue;
a cartridge including a rigid frame defining at least one elongated lumen for fully receiving the at least one stapling element within the lumen; and
a driving unit, in mechanical communication with said cartridge, operative to issue said at least one stapling element from said cartridge;
wherein the at least one stapling element forms:
a first shape while maintained within the lumen of the cartridge, the first shape being a straight elongated shaped body with a tapered end, and including a characteristic along a length of the elongated body operative to prevent rotation of the stapling element about its longitudinal axis as it is issued from the cartridge; and
a second shape when issued from the cartridge; the second shape being a closed loop shape, wherein the stapling element self-deforms from the first shape to the second shape as it issues from the cartridge; and
wherein a cross section of the lumen matches the characteristic of the stapling element and engages with it to prevent the stapling element from rotating about its longitudinal axis as it is issued.

2. The system of claim 1, wherein the system is adapted for fastening at least two layers of tissue.

3. The system of claim 1, adapted for forming an edge seam.

4. The system of claim 1, adapted for joining at least two tissue edges, arranged end to end.

5. The system of claim 1, adapted for joining a tissue and an artificial material selected from a mesh and a patch.

6. The system of claim 1, wherein the at least one stapling element has a length between 4 mm and 200 mm.

7. The system of claim 1, wherein said second shape forms a closed loop, with said tapered end, fitting into a cavity formed in an opposite end.

8. The system of claim 1, wherein said second shape is a closed loop, with said tapered end, arranged against an opposite end of said stapling element, while maintaining a same cross sectional diameter of said elongated body.

9. The system of claim 1, wherein said elongated body and said lumen have a matching cross section selected from the group consisting of an elliptical cross section and a polygonal cross section, and wherein said cross section is operative as said characteristic of said elongated body, for preventing said stapling element from rotating, within said cartridge.

10. The system of claim 1, wherein the characteristic of said elongated body is one of a rim and a notch extending along the elongated body and engaging with one of a notch and rim respectively of the cartridge.

11. The system of claim 1, wherein said tapered end is curved in a direction of closing, in said first shape, for piercing the tissue at the angle of closing.

12. The system of claim 1, wherein said tapered end has a triangular cross section, adapted for piercing hard tissue.

13. The system of claim 1, wherein said tapered portion, has a screw thread.

14. The system of claim 1, wherein said second shape is further designed to close around its longitudinal axis, for piercing the tissue, by self-threading into it.

15. The system of claim 1, wherein the stapling element is formed of a shape memory alloy.

16. The system of claim 1, wherein said at least one stapling element is formed as a composite of at least two materials, longitudinally disposed.

17. The system of claim 1, wherein said at least one stapling element is formed of a resilient material, wherein said first shape, adapted for insertion into the tissue, is constrained in said first shape.

18. The system of claim 1, comprising a handle, with a finger lever, for controlling said driving unit, wherein said handle is arranged at an angle to said cartridge, to allow a surgeon maximum maneuverability, with a full range of elbow bending.

19. The system of claim 1, wherein said driving unit is further operative to issue said at least one stapling element gradually.

20. The system of claim 1, wherein said cartridge includes an opening from which said at least one stapling element issues, wherein said opening is at angle, which is smaller than 90° to said at least one stapling element.

21. The system of claim 1, comprising a counter frame, on a side proximal to said tissue for holding the tissue between said cartridge and the counter frame.

22. The system of claim 1, adapted for endoscopy.

23. The system of claim 1, wherein said cartridge, adapted for receiving at least one stapling element, is further adapted for receiving a plurality of stapling elements, arranged in a file, and issued one by one, each forming a staple, so that said device is operative as a Self-Closing Stapling, Intermittent-Firing (SCS-IF™) Device.

24. The system of claim 1, wherein said cartridge, adapted for receiving at least one stapling element, is further adapted for receiving a plurality of stapling elements, arranged parallel to each other, as a row.

25. The system of claim 24, wherein said cartridge is further adapted for issuing said stapling elements simultaneously for forming a single seam of a plurality of staples, so that said device is operative as a Self-Closing Stapling-Transverse Anastomosis (SCS-TA™) device.

26. The system of claim 1, wherein said cartridge, adapted for receiving at least one stapling element, is further adapted for receiving a plurality of stapling elements, arranged parallel to each other, as two rows.

27. The system of claim 26, wherein said cartridge is further adapted for issuing said stapling elements simultaneously for forming two parallel seams, so that said device is operative as a Self-Closing Stapling-Gastro-Intestinal Anastomosis (SCS-GIA™).

28. The system of claim 1, wherein said cartridge, adapted for receiving at least one stapling element, is circular, adapted for receiving a plurality of stapling elements, arranged in a circle, parallel to each other.

29. The system of claim 28, wherein said cartridge is further adapted for issuing said stapling elements simultaneously for forming a circular seam of a plurality of staples, so that said device is operative as a Self-Closing Stapling-End-to-End Anastomosis (SCS-EEA™), further adapted for endoscopy.

30. The system of claim 1, wherein said cartridge, adapted for receiving at least one staple element, comprises a plurality of staples, and said driving unit is adapted to issue said plurality of staples in parallel, for applying a row of staples.

31. The system of claim 30, wherein said cartridge is further adapted for issuing said row of staples simultaneously and gradually, so that said device is operative as a Self-Closing Stapling, Simultaneous-Gradual-Firing (SCS-SGF™) device.

32. The system of claim 1, adapted for the application of a single staple.

33. The system according to claim 1, wherein the cartridge includes an opening through which the at least one stapling element is issued and wherein a shape of the opening defines a closing direction of the stapling element with respect to the opening.

34. The system of claim 33, said cartridge having a gripping handle defining a gripping position of a user's hand, and said system being adapted for changing the closing direction without changing said gripping position.

35. The system according to claim 1, wherein said second shape is a closed loop, with said tapered end being internal to the loop.

36. The system according to claim 1, wherein said second shape is a closed loop, with said tapered end being external to the loop.

37. The system according to claim 1, wherein said characteristic along a length of the elongated body comprises a physical feature extending along a length of the elongated body.

38. The system of claim 1, wherein said cartridge, adapted for receiving at least one stapling element, is further adapted for receiving a plurality of stapling elements and for issuing said plurality of stapling elements sequentially.

39. A method for staple application, the method comprising:
providing at least one stapling element, the stapling element forming:
a first shape while fully maintained within a lumen of a cartridge, the first shape being a straight elongated body with a tapered end, and including a characteristic along a length of the elongated body operative to prevent rotation of the stapling element about its longitudinal axis as it is issued from the cartridge; and
a second shape self-formed when issued from the cartridge; the second shape being a closed loop shape;
issuing the at least one stapling element through the lumen of the cartridge, while engaging the stapling element by a cross-section of lumen to prevent the stapling element from rotating about its longitudinal axis as it issues;
piercing a tissue with the exposed tapered end of the stapling element;

allowing the at least one stapling element to self-close into the closed loop shape through the tissue as it issues from the cartridge.

40. The method of claim 39, wherein said piercing further includes piercing gradually, hence, with minimal tissue crushing.

41. The method of claim 39, wherein said piercing a tissue further includes piercing at an angle, which is smaller than 90° to said stapling element.

42. The method according to claim 39, wherein the cartridge includes an opening through which the at least one stapling element is issued and wherein a shape of the opening defines a closing direction of the stapling element with respect to the opening.

43. The method of claim 42, wherein said piercing further includes piercing while maintaining the closing direction of said at least one stapling element.

44. The method of claim 42, comprising:
inserting said stapling element in said cartridge, said cartridge having a gripping handle defining a gripping position; and
changing said closing direction without changing said gripping position.

45. The method according to claim 39, wherein said characteristic along a length of the elongated body comprises a physical feature extending along a length of the elongated body.

* * * * *